(12) United States Patent
Sakakibara et al.

(10) Patent No.: US 8,185,321 B2
(45) Date of Patent: May 22, 2012

(54) METHOD FOR PREDICTING INTERACTION BETWEEN PROTEIN AND CHEMICAL

(75) Inventors: Yasubumi Sakakibara, Kanagawa (JP); Nobuyoshi Nagamine, Kanagawa (JP)

(73) Assignee: Keio University, Tokyo (JP)

( * ) Notice: Subject to any disclaimer, the term of this patent is extended or adjusted under 35 U.S.C. 154(b) by 413 days.

(21) Appl. No.: 12/447,814

(22) PCT Filed: Oct. 31, 2007

(86) PCT No.: PCT/JP2007/071236
§ 371 (c)(1),
(2), (4) Date: Jun. 2, 2009

(87) PCT Pub. No.: WO2008/053924
PCT Pub. Date: May 8, 2008

(65) Prior Publication Data
US 2010/0070438 A1    Mar. 18, 2010

(30) Foreign Application Priority Data

Oct. 31, 2006  (JP) .................................. 2006-297111

(51) Int. Cl.
*G06F 19/00* (2011.01)
*G01N 33/48* (2006.01)
(52) U.S. Cl. ........................................... 702/19; 702/27
(58) Field of Classification Search .................. None
See application file for complete search history.

(56) References Cited

OTHER PUBLICATIONS

Wikipedia: Support Vector Machine [retrieved on Sep. 22, 2011]. Retrieved from the Internet http://en.wikipedia.org/wiki/Support_vector-machine.*
Bock and Gough, "Predicting Protein-Protein Interactions from Primary Structure," *Bioinformatics* 17(5):455-460 (2001).
West-Nielsen et al., "Sample Handling for Mass Spectrometric Proteomic Investigations of Human Sera," *Anal. Chem.* 77(16):5114-5123 (2005).
Yanover and Hertz, "Predicting Protein-Peptide Binding Affinity by Learning Peptide-Peptide Distance Functions," Research in Computational Molecular Biology 3500:456-471 (2005).
English Language International Search Report for International Application No. PCT/JP2007/071236, mailed Jan. 29, 2008.

* cited by examiner

*Primary Examiner* — John S Brusca
(74) *Attorney, Agent, or Firm* — Clark & Elbing LLP

(57) ABSTRACT

The present invention provides a method for configuring a pattern recognizer using versatile, readily available data, comprehensive protein data, and comprehensive chemical data, as well as a method for predicting an unknown interaction of a pair by using the pattern recognizer-configuring method. An interaction such as the coupling between a protein and a chemical is used as an index; at least one of four parameters is vectorized; a vector containing elements of the vector derived from each protein and elements of the vector derived from each chemical paired with the protein is created; and a support vector machine (SVM) is applied to this vector and trained to learn them, where the pattern recognizer is configured so as to discriminate between a class to which the first pair belong and a class to which the second pair belong.

19 Claims, 52 Drawing Sheets

| Index | Property Name | References |
|---|---|---|
| 1 | Hydrophobicity index | Argos P, Rao JK, Hargrave PA (1982) Eur J Biochem 128:565-575 |
| 2 | Conformational parameter of beta-structure | Beghin F, Dirkx J (1975) Arch Int Physiol Biochim 83:167-168 |
| 3 | Conformational parameter of beta-turn | Beghin F, Dirkx J (1975) Arch Int Physiol Biochim 83:167-168 |
| 4 | Average flexibility indices | Bhaskaran R, Ponnuswamy PK (1988) Int J Peptide Protein Res 32:241-255 |
| 5 | Residue volume | Bigelow CC (1967) J Theor Biol 16:187-211 |
| 6 | Information value for accessibility; average fraction 35% | Biou V, Gibrat JF, Levin JM, Robson B, Garnier J (1988) Protein Eng 2:185-191 |
| 7 | Information value for accessibility; average fraction 23% | Biou V, Gibrat JF, Levin JM, Robson B, Garnier J (1988) Protein Eng 2:185-191 |
| 8 | Retention coefficient in TFA | Browne CA, Bennett HP, Solomon S (1982) Anal Biochem 124:201-208 |
| 9 | Retention coefficient in HFBA | Browne CA, Bennett HP, Solomon S (1982) Anal Biochem 124:201-208 |
| 10 | Transfer free energy to surface | Bull HB, Breese K (1974) Arch Biochem Biophys 161:665-670 |
| 11 | Apparent partial specific volume | Bull HB, Breese K (1974) Arch Biochem Biophys 161:665-670 |
| 12 | Normalized frequency of alpha-helix | Burgess AW, Ponnuswamy PK, Scheraga HA (1974) Isr J Chem 12:239-286 |
| 13 | Normalized frequency of extended structure | Burgess AW, Ponnuswamy PK, Scheraga HA (1974) Isr J Chem 12:239-286 |
| 14 | Steric parameter | Charton M (1981) J Theor Biol 91:115-123 |

FIG. 1A

| Index | Property Name | References |
|---|---|---|
| 15 | Polarizability parameter | Charton M, Charton BI (1982) J Theor Biol 99:629-644 |
| 16 | The Chou-Fasman parameter of the coil conformation | Charton M, Charton BI (1983) J Theor Biol 102:121-134 |
| 17 | Average volume of buried residue | Chothia C (1975) Nature 254:304-308 |
| 18 | Residue accessible surface area in tripeptide | Chothia C (1976) J Mol Biol 105:1-12 |
| 19 | Residue accessible surface area in folded protein | Chothia C (1976) J Mol Biol 105:1-12 |
| 20 | Proportion of residues 95% buried | Chothia C (1976) J Mol Biol 105:1-12 |
| 21 | Proportion of residues 100% buried | Chothia C (1976) J Mol Biol 105:1-12 |
| 22 | Normalized frequency of beta-turn | Chou PY, Fasman GD (1978) Ann Rev Biochem 47:251-276 |
| 23 | Normalized frequency of alpha-helix | Chou PY, Fasman GD (1978) Adv Enzymol 47:45-148 |
| 24 | Normalized frequency of beta-sheet | Chou PY, Fasman GD (1978) Adv Enzymol 47:45-148 |
| 25 | Normalized frequency of beta-turn | Chou PY, Fasman GD (1978) Adv Enzymol 47:45-148 |
| 26 | Normalized average hydrophobicity scales | Cid H, Bunster M, Canales M, Gazitua F(1992) Protein Eng 5:373-375 |
| 27 | Partial specific volume | Cohn EJ, Edsal JT (1943) Protein, Amino Acid, and Peptides, Reinhold, New York |
| 28 | Normalized frequency of beta-sheet | Crawford JL, Lipscomb WN, Schellman CG (1973) Proc Natl Acad Sci USA 70:538-542 |
| 29 | Normalized frequency of turn | Crawford JL, Lipscomb WN, Schellman CG (1973) Proc Natl Acad Sci USA 70:538-542 |
| 30 | Size | Brock DJH, Mayo O (1972) The Biochemical Genetics of Man, Academic Press, New York |
| 31 | Amino acid composition | Dayhoff MO, Hunt, LT, and Hurst-Calderone S (1978) Composition of proteins. In: Dayhoff MO (ed) Atlas of Protein Sequence and Structure, Vol 5 Suppl 3, National Biomedical Research Foundation, Washington DC, pp 363-364 |

FIG. 1B

| Index | Property Name | References |
|---|---|---|
| 32 | Relative mutability | Dayhoff MO, Schwartz RM, Orcutt BC (1978) A model of evolutionary change in proteins. In: Dayhoff MO (ed) Atlas of Protein Sequence and Structure, Vol 5 Suppl 3, National Biomedical Research Foundation, Washington DC, pp 345-352 |
| 33 | Consensus normalized hydrophobicity scale | Eisenberg D (1984) Ann Rev Biochem 53:595-623 |
| 34 | Solvation free energy | Eisenberg D, McLachlan AD (1986) Nature 319:199-203 |
| 35 | Atom-based hydrophobic moment | Eisenberg D, McLachlan AD (1986) Nature 319:199-203 |
| 36 | Molecular weight | Fasman GD (1976) Handbook of Biochemistry and Molecular Biology, 3rd edn. CRC Press, Cleveland |
| 37 | Hydrophobic parameter pi | Fauchere JL, Pliska V (1983) Eur J Med Chem 18:369-375 |
| 38 | Graph shape index | Fauchere JL, Charton M, Kier LB, Verloop A, Pliska V (1988) Int J Pept Protein Res 32:269-278 |
| 39 | Normalized van der Waals volume | Fauchere JL, Charton M, Kier LB, Verloop A, Pliska V (1988) Int J Pept Protein Res 32:269-278 |
| 40 | STERIMOL length of the side chain | Fauchere JL, Charton M, Kier LB, Verloop A, Pliska V (1988) Int J Pept Protein Res 32:269-278 |
| 41 | STERIMOL minimum width of the side chain | Fauchere JL, Charton M, Kier LB, Verloop A, Pliska V (1988) Int J Pept Protein Res 32:269-278 |
| 42 | STERIMOL maximum width of the side chain | Fauchere JL, Charton M, Kier LB, Verloop A, Pliska V (1988) Int J Pept Protein Res 32:269-278 |
| 43 | Number of hydrogen bond donors | Fauchere JL, Charton M, Kier LB, Verloop A, Pliska V (1988) Int J Pept Protein Res 32:269-278 |
| 44 | Positive charge | Fauchere JL, Charton M, Kier LB, Verloop A, Pliska V (1988) Int J Pept Protein Res 32:269-278 |
| 45 | Negative charge | Fauchere JL, Charton M, Kier LB, Verloop A, Pliska V (1988) Int J Pept Protein Res 32:269-278 |
| 46 | Helix-coil equilibrium constant | Finkelstein AV, Ptitsyn OB (1977) Biopolymers 16:497-524 |
| 47 | Partition coefficient | Garel JP, Filliol D, Mandel P (1973) J Chromatogr 78:381-391 |

FIG. 1C

| Index | Property Name | References |
|---|---|---|
| 48 | Alpha-helix indices | Geisow MJ, Roberts RDB (1980) Int J Biol Macromol 2:387-389 |
| 49 | Beta-strand indices | Geisow MJ, Roberts RDB (1980) Int J Biol Macromol 2:387-389 |
| 50 | Hydrophobicity factor | Goldsack DE, Chalifoux RC (1973) J Theor Biol 39:645-651 |
| 51 | Residue volume | Goldsack DE, Chalifoux RC (1973) J Theor Biol 39:645-651 |
| 52 | Composition | Grantham R (1974) Science 185:862-864 |
| 53 | Polarity | Grantham R (1974) Science 185:862-864 |
| 54 | Volume | Grantham R (1974) Science 185:862-864 |
| 55 | Partition energy | Guy HR (1985) Biophys J 47:61-70 |
| 56 | Hydration number | Anthony JH (1977) Intermolecular Interactions and Biomolecular Organizations, Wiley Johns & Sons, New York. |
| 57 | Hydrophilicity value | Hopp TP, Woods KR (1981) Proc Natl Acad Sci USA 78:3824-3828 |
| 58 | Heat capacity | Hutchens JO (1970) Heat capacities, absolute entropies, and entropies of formation of amino acids and related compounds. In: Sober HA (ed) Handbook of Biochemistry, 2nd edn, CRC Press, Cleveland, PP. B60-B61 |
| 59 | Absolute entropy | Hutchens JO (1970) Heat capacities, absolute entropies, and entropies of formation of amino acids and related compounds. In: Sober HA (ed) Handbook of Biochemistry, 2nd edn, CRC Press, Cleveland, PP. B60-B61 |
| 60 | Entropy of formation | Hutchens JO (1970) Heat capacities, absolute entropies, and entropies of formation of amino acids and related compounds. In: Sober HA (ed) Handbook of Biochemistry, 2nd edn, CRC Press, Cleveland, PP. B60-B61 |
| 61 | Normalized relative frequency of alpha-helix | Isogai Y, Nemethy G, Rackovsky S, Leach SJ, Scheraga HA (1980) Biopolymers 19:1183-1210 |
| 62 | Normalized relative frequency of extended structure | Isogai Y, Nemethy G, Rackovsky S, Leach SJ, Scheraga HA (1980) Biopolymers 19:1183-1210 |

FIG. 1D

| Index | Property Name | References |
|---|---|---|
| 63 | Normalized relative frequency of bend | Isogai Y, Nemethy G, Rackovsky S, Leach SJ, Scheraga HA (1980) Biopolymers 19:1183-1210 |
| 64 | Normalized relative frequency of coil | Isogai Y, Nemethy G, Rackovsky S, Leach SJ, Scheraga HA (1980) Biopolymers 19:1183-1210 |
| 65 | Average accessible surface area | Janin J, Wodak SJ (1978) J Mol Biol 125:357-386 |
| 66 | Percentage of buried residues | Janin J, Wodak SJ (1978) J Mol Biol 125:357-386 |
| 67 | Percentage of exposed residues | Janin J, Wodak SJ (1978) J Mol Biol 125:357-386 |
| 68 | Ratio of buried and accessible molar fractions | Janin J (1979) Nature 277:491-492 |
| 69 | Transfer free energy | Janin J (1979) Nature 277:491-492 |
| 70 | Hydrophobicity | Jones DD (1975) J Theor Biol 50:167-183 |
| 71 | Relative frequency of occurrence | Jones DT, Taylor WR, Thornton JM (1992) Comput Appl Biosci 8:275-282 |
| 72 | Relative mutability | Jones DT, Taylor WR, Thornton JM (1992) Comput Appl Biosci 8:275-282 |
| 73 | Amino acid distribution | Jukes TH, Holmquist R, Moise H (1975) Science 189:50-51 |
| 74 | Sequence frequency | Jungck JR (1978) J Mol Evol 11:211-224 |
| 75 | Average relative probability of helix | Kanehisa MI, Tsong TY (1980) Biopolymers 19:1617-1628 |
| 76 | Average relative probability of beta-sheet | Kanehisa MI, Tsong TY (1980) Biopolymers 19:1617-1628 |
| 77 | Flexibility parameter for no rigid neighbors | Karplus PA, Schulz GE (1985) Naturwissenchaften 72:212-213 |
| 78 | Flexibility parameter for one rigid neighbor | Karplus PA, Schulz GE (1985) Naturwissenchaften 72:212-213 |
| 79 | Flexibility parameter for two rigid neighbors | Karplus PA, Schulz GE (1985) Naturwissenchaften 72:212-213 |
| 80 | Net charge | Klein P, Kanehisa M, DeLisi C (1984) Biochim Biophys Acta 787:221-226 |
| 81 | Side chain interaction parameter | Krigbaum WR, Rubin BH (1971) Biochim Biophys Acta 229:368-383 |
| 82 | Side chain interaction parameter | Krigbaum WR, Komoriya A (1979) Biochim Biophys Acta 576:204-248 |
| 83 | Fraction of site occupied by water | Krigbaum WR, Komoriya A (1979) Biochim Biophys Acta 576:204-248 |
| 84 | Side chain volume | Krigbaum WR, Komoriya A (1979) Biochim Biophys Acta 576:204-248 |

FIG. 1E

| Index | Property Name | References |
|---|---|---|
| 85 | Hydropathy index | Kyte J, Doolittle RF (1982) J Mol Biol 157:105-132 |
| 86 | Transfer free energy, CHP/water | Lawson EQ, Sadler AJ, Harmatz D, Brandau DT, Micanovic R, MacElroy RD, Middaugh CR (1984) J Biol Chem 259:2910-2912 |
| 87 | Hydrophobic parameter | Levitt M (1976) J Mol Biol 104:59-107 |
| 88 | Distance between C-alpha and centroid of side chain | Levitt M (1976) J Mol Biol 104:59-107 |
| 89 | Side chain torsion angle phi | Levitt M (1976) J Mol Biol 104:59-107 |
| 90 | Radius of gyration of side chain | Levitt M (1976) J Mol Biol 104:59-107 |
| 91 | van der Waals parameter R0 | Levitt M (1976) J Mol Biol 104:59-107 |
| 92 | van der Waals parameter epsilon | Levitt M (1976) J Mol Biol 104:59-107 |
| 93 | Normalized frequency of alpha-helix, with weights | Levitt M (1978) Biochemistry 17:4277-4285 |
| 94 | Normalized frequency of beta-sheet, with weights | Levitt M (1978) Biochemistry 17:4277-4285 |
| 95 | Normalized frequency of reverse turn, with weights | Levitt M (1978) Biochemistry 17:4277-4285 |
| 96 | Normalized frequency of alpha-helix, unweighted | Levitt M (1978) Biochemistry 17:4277-4285 |
| 97 | Normalized frequency of beta-sheet, unweighted | Levitt M (1978) Biochemistry 17:4277-4285 |
| 98 | Normalized frequency of reverse turn, unweighted | Levitt M (1978) Biochemistry 17:4277-4285 |
| 99 | Conformational preference for all beta-strands | Lifson S, Sander C (1979) Nature 282:109-111 |
| 100 | Conformational preference for parallel beta-strands | Lifson S, Sander C (1979) Nature 282:109-111 |
| 101 | Conformational preference for antiparallel beta-strands | Lifson S, Sander C (1979) Nature 282:109-111 |
| 102 | Average surrounding hydrophobicity | Manavalan P, Ponnuswamy PK (1978) Nature 275:673-674 |
| 103 | Normalized frequency of alpha-helix | Maxfield FR, Scheraga HA (1976) Biochemistry 15:5138-5153 |
| 104 | Normalized frequency of extended structure | Maxfield FR, Scheraga HA (1976) Biochemistry 15:5138-5153 |
| 105 | Normalized frequency of left-handed alpha-helix | Maxfield FR, Scheraga HA (1976) Biochemistry 15:5138-5153 |
| 106 | Refractivity | McMeekin TL, Groves ML, Hipp NJ (1964) Refractivity. In: Stekol JA (ed) Amino Acids and Serum Proteins, American Chemical Society, Washington DC, pp. 54-55 |

FIG. 1F

| Index | Property Name | References |
|---|---|---|
| 107 | Retention coefficient in HPLC, pH7.4 | Meek JL (1980) Proc Natl Acad Sci USA 77:1632-1636 |
| 108 | Retention coefficient in HPLC, pH2.1 | Meek JL (1980) Proc Natl Acad Sci USA 77:1632-1636 |
| 109 | Retention coefficient in NaClO4 | Meek JL, Rossetti ZL (1981) J Chromatogr 211:15-28 |
| 110 | Retention coefficient in NaH2PO4 | Meek JL, Rossetti ZL (1981) J Chromatogr 211:15-28 |
| 111 | Average reduced distance for C-alpha | Meirovitch H, Rcackovsky S, Scheraga HA (1980) Macromolecules 13:1398-1405 |
| 112 | Average reduced distance for side chain | Meirovitch H, Rcackovsky S, Scheraga HA (1980) Macromolecules 13:1398-1405 |
| 113 | Average side chain orientation angle | Meirovitch H, Rcackovsky S, Scheraga HA (1980) Macromolecules 13:1398-1405 |
| 114 | Effective partition energy | Miyazawa S, Jernigan RL (1985) Macromolecules 18:534-552 |
| 115 | Normalized frequency of alpha-helix | Nagano K (1973) J Mol Biol 75:401-420 |
| 116 | Normalized frequency of beta-structure | Nagano K (1973) J Mol Biol 75:401-420 |
| 117 | Normalized frequency of coil | Nagano K (1973) J Mol Biol 75:401-420 |
| 118 | AA composition of total proteins | Nakashima H, Nishikawa K, Ooi T (1990) Proteins 8:173-178 |
| 119 | Sof AA composition of total proteins | Nakashima H, Nishikawa K, Ooi T (1990) Proteins 8:173-178 |
| 120 | AA composition of membrane proteins | Nakashima H, Nishikawa K, Ooi T (1990) Proteins 8:173-178 |
| 121 | Normalized composition of membrane proteins | Nakashima H, Nishikawa K, Ooi T (1990) Proteins 8:173-178 |
| 122 | Ratio of average and computed composition | Nakashima H, Nishikawa K, Ooi T (1990) Proteins 8:173-178 |
| 123 | 8 A contact number | Nishikawa K, Ooi T (1980) Int J Pept Protein Res 16:19-32 |
| 124 | 14 A contact number | Nishikawa K, Ooi T (1986) J Biochem 100:1043-1047 |
| 125 | Average non-bonded energy per atom | Oobatake M, Ooi T (1977) J Theor Biol 67:567-584 |
| 126 | Short and medium range non-bonded energy per atom | Oobatake M, Ooi T (1977) J Theor Biol 67:567-584 |
| 127 | Long range non-bonded energy per atom | Oobatake M, Ooi T (1977) J Theor Biol 67:567-584 |
| 128 | Average non-bonded energy per residue | Oobatake M, Ooi T (1977) J Theor Biol 67:567-584 |

FIG. 1G

| Index | Property Name | References |
|---|---|---|
| 129 | Short and medium range non-bonded energy per residue | Oobatake M, Ooi T (1977) J Theor Biol 67:567-584 |
| 130 | Optimized beta-structure-coil equilibrium constant | Oobatake M, Kubota Y, Ooi T (1985) Bull Inst Chem Res Kyoto Univ 63:82-94 |
| 131 | Optimized propensity to form reverse turn | Oobatake M, Kubota Y, Ooi T (1985) Bull Inst Chem Res Kyoto Univ 63:82-94 |
| 132 | Optimized transfer energy parameter | Oobatake M, Kubota Y, Ooi T (1985) Bull Inst Chem Res Kyoto Univ 63:82-94 |
| 133 | Optimized average non-bonded energy per atom | Oobatake M, Kubota Y, Ooi T (1985) Bull Inst Chem Res Kyoto Univ 63:82-94 |
| 134 | Optimized side chain interaction parameter | Oobatake M, Kubota Y, Ooi T (1985) Bull Inst Chem Res Kyoto Univ 63:82-94 |
| 135 | Normalized frequency of alpha-helix from LG | Palau J, Argos P, Puigdomenech P (1982) Int J Pept Prot Res 19:394-401 |
| 136 | Normalized frequency of alpha-helix from CF | Palau J, Argos P, Puigdomenech P (1982) Int J Pept Prot Res 19:394-401 |
| 137 | Normalized frequency of beta-sheet from LG | Palau J, Argos P, Puigdomenech P (1982) Int J Pept Prot Res 19:394-401 |
| 138 | Normalized frequency of beta-sheet from CF | Palau J, Argos P, Puigdomenech P (1982) Int J Pept Prot Res 19:394-401 |
| 139 | Normalized frequency of turn from LG | Palau J, Argos P, Puigdomenech P (1982) Int J Pept Prot Res 19:394-401 |
| 140 | Normalized frequency of turn from CF | Palau J, Argos P, Puigdomenech P (1982) Int J Pept Prot Res 19:394-401 |
| 141 | HPLC parameter | Parker JM, Guo D, Hodges RS (1986) Biochemistry 25:5425-5432 |
| 142 | Partition coefficient | Pliska V, Schmidt M, Fauchere JL (1981) J Chromatogr 216:79-92 |
| 143 | Surrounding hydrophobicity in folded form | Ponnuswamy PK, Prabhakaran M, Manavalan P (1980) Biochim Biophys Acta 623:301-316 |
| 144 | Average gain in surrounding hydrophobicity | Ponnuswamy PK, Prabhakaran M, Manavalan P (1980) Biochim Biophys Acta 623:301-316 |
| 145 | Average gain ratio in surrounding hydrophobicity | Ponnuswamy PK, Prabhakaran M, Manavalan P (1980) Biochim Biophys Acta 623:301-316 |
| 146 | Surrounding hydrophobicity in alpha-helix | Ponnuswamy PK, Prabhakaran M, Manavalan P (1980) Biochim Biophys Acta 623:301-316 |

FIG. 1H

| Index | Property Name | References |
|---|---|---|
| 147 | Surrounding hydrophobicity in beta-sheet | Ponnuswamy PK, Prabhakaran M, Manavalan P (1980) Biochim Biophys Acta 623:301-316 |
| 148 | Surrounding hydrophobicity in turn | Ponnuswamy PK, Prabhakaran M, Manavalan P (1980) Biochim Biophys Acta 623:301-316 |
| 149 | Accessibility reduction ratio | Ponnuswamy PK, Prabhakaran M, Manavalan P (1980) Biochim Biophys Acta 623:301-316 |
| 150 | Average number of surrounding residues | Ponnuswamy PK, Prabhakaran M, Manavalan P (1980) Biochim Biophys Acta 623:301-316 |
| 151 | Intercept in regression analysis | Prabhakaran M, Ponnuswamy PK (1982) Macromolecules 15:314-320 |
| 152 | Slope in regression analysis x 1.0E1 | Prabhakaran M, Ponnuswamy PK (1982) Macromolecules 15:314-320 |
| 153 | Correlation coefficient in regression analysis | Prabhakaran M, Ponnuswamy PK (1982) Macromolecules 15:314-320 |
| 154 | Hydrophobicity | Prabhakaran M (1990) Biochem. J. 269:691-696 |
| 155 | Relative frequency in alpha-helix | Prabhakaran M (1990) Biochem. J. 269:691-696 |
| 156 | Relative frequency in beta-sheet | Prabhakaran M (1990) Biochem. J. 269:691-696 |
| 157 | Relative frequency in reverse-turn | Prabhakaran M (1990) Biochem. J. 269:691-696 |
| 158 | Helix-coil equilibrium constant | Ptitsyn OB, Finkelstein AV (1983) Biopolymers 22:15-25 |
| 159 | Beta-coil equilibrium constant | Ptitsyn OB, Finkelstein AV (1983) Biopolymers 22:15-25 |
| 160 | Average reduced distance for C-alpha | Rackovsky S, Scheraga HA (1977) Proc Natl Acad Sci USA 74:5248-5251 |
| 161 | Average reduced distance for side chain | Rackovsky S, Scheraga HA (1977) Proc Natl Acad Sci USA 74:5248-5251 |
| 162 | Side chain orientational preference | Rackovsky S, Scheraga HA (1977) Proc Natl Acad Sci USA 74:5248-5251 |
| 163 | Information measure for alpha-helix | Robson B, Suzuki E (1976) J Mol Biol 107:327-356 |
| 164 | Information measure for extended | Robson B, Suzuki E (1976) J Mol Biol 107:327-356 |
| 165 | Information measure for pleated-sheet | Robson B, Suzuki E (1976) J Mol Biol 107:327-356 |
| 166 | Information measure for extended without H-bond | Robson B, Suzuki E (1976) J Mol Biol 107:327-356 |
| 167 | Information measure for turn | Robson B, Suzuki E (1976) J Mol Biol 107:327-356 |

FIG. 1 I

| Index | Property Name | References |
|---|---|---|
| 168 | Information measure for coil | Robson B, Suzuki E (1976) J Mol Biol 107:327-356 |
| 169 | Information measure for loop | Robson B, Suzuki E (1976) J Mol Biol 107:327-356 |
| 170 | Hydration free energy | Robson B, Osguthorpe DJ (1979) J Mol Biol 132:19-51 |
| 171 | Mean area buried on transfer | Rose GD, Geselowitz AR, Lesser GJ, Lee RH, Zehfus MH (1985) Science 229:834-838 |
| 172 | Mean fractional area loss | Rose GD, Geselowitz AR, Lesser GJ, Lee RH, Zehfus MH (1985) Science 229:834-838 |
| 173 | Side chain hydropathy, uncorrected for solvation | Roseman MA (1988) J Mol Biol 200:513-522 |
| 174 | Side chain hydropathy, corrected for solvation | Roseman MA (1988) J Mol Biol 200:513-522 |
| 175 | Loss of Side chain hydropathy by helix formation | Roseman MA (1988) J Mol Biol 200:513-522 |
| 176 | Transfer free energy | Simon Z (1976) Quantum Biochemistry and Specific Interactions, Abacus Press |
| 177 | Principal component I | Sneath PH (1966) J Theor Biol 12:157-195 |
| 178 | Principal component II | Sneath PH (1966) J Theor Biol 12:157-195 |
| 179 | Principal component III | Sneath PH (1966) J Theor Biol 12:157-195 |
| 180 | Principal component IV | Sneath PH (1966) J Theor Biol 12:157-195 |
| 181 | Zimm-Bragg parameter s at 20 C | Sueki M, Lee S, Powers SP, Denton JB, Konishi Y, Scheraga H (1984) Macromolecules 17:148-155 |
| 182 | Zimm-Bragg parameter sigma x 1.0E4 | Sueki M, Lee S, Powers SP, Denton JB, Konishi Y, Scheraga H (1984) Macromolecules 17:148-155 |
| 183 | Optimal matching hydrophobicity | Sweet RM, Eisenberg D (1983) J Mol Biol 171:479-488 |
| 184 | Normalized frequency of alpha-helix | Tanaka S, Scheraga HA (1977) Macromolecules 10:9-20 |
| 185 | Normalized frequency of extended structure | Tanaka S, Scheraga HA (1977) Macromolecules 10:9-20 |
| 186 | Normalized frequency of coil | Tanaka S, Scheraga HA (1977) Macromolecules 10:9-20 |
| 187 | Relative population of conformational state A | Vasquez M, Nemethy G, Scheraga HA (1983) Macromolecules 16:1043-1049 |
| 188 | Relative population of conformational state C | Vasquez M, Nemethy G, Scheraga HA (1983) Macromolecules 16:1043-1049 |

FIG. 1 J

| Index | Property Name | References |
|---|---|---|
| 189 | Relative population of conformational state E | Vasquez M, Nemethy G, Scheraga HA (1983) Macromolecules 16:1043-1049 |
| 190 | Electron-ion interaction potential | Veljkovic V, Cosic I, Dimitrijevic B, Lalovic D (1985) IEEE Trans Biomed Eng 32:337-341 |
| 191 | Transfer free energy to lipophilic phase | von Heijne G, Blomberg C (1979) Eur J Biochem 97:175-181 |
| 192 | Average interactions per side chain atom | Warme PK, Morgan RS (1978) J Mol Biol 118:289-304 |
| 193 | RF value in high salt chromatography | Weber AL, Lacey JC (1978) J Mol Evol 11:199-210 |
| 194 | Propensity to be buried inside | Wertz DH, Scheraga HA (1978) Macromolecules 11:9-15 |
| 195 | Free energy change of epsilon(i) to epsilon(ex) | Wertz DH, Scheraga HA (1978) Macromolecules 11:9-15 |
| 196 | Free energy change of alpha(Ri) to alpha(Rh) | Wertz DH, Scheraga HA (1978) Macromolecules 11:9-15 |
| 197 | Free energy change of epsilon(i) to alpha(Rh) | Wertz DH, Scheraga HA (1978) Macromolecules 11:9-15 |
| 198 | Polar requirement | Woese CR (1973) Naturwissenschaften 60:447-459 |
| 199 | Hydration potential | Wolfenden R, Andersson L, Cullis PM, Southgate CC (1981) Biochemistry 20:849-855 |
| 200 | Hydrophobicity | Zimmerman JM, Eliezer N, Simha R (1968) J Theor Biol 21:170-201 |
| 201 | Bulkiness | Zimmerman JM, Eliezer N, Simha R (1968) J Theor Biol 21:170-201 |
| 202 | Polarity | Zimmerman JM, Eliezer N, Simha R (1968) J Theor Biol 21:170-201 |
| 203 | Isoelectric point | Zimmerman JM, Eliezer N, Simha R (1968) J Theor Biol 21:170-201 |
| 204 | RF rank | Zimmerman JM, Eliezer N, Simha R (1968) J Theor Biol 21:170-201 |
| 205 | Delta G values for the peptides extrapolated to 0 M urea | O'Neil KT, DeGrado WF (1990) Science 250:646-651 |
| 206 | Helix formation parameters (delta delta G) | O'Neil KT, DeGrado WF (1990) Science 250:646-651 |
| 207 | Normalized flexibility parameters (B-values) average | Vihinen M, Torkkila E, Riikonen P (1994) Proteins 19:141-149 |
| 208 | Normalized flexibility parameters (B-values) | Vihinen M, Torkkila E, Riikonen P (1994) Proteins 19:141-149 |
| 209 | Normalized flexibility parameters (B-values) | Vihinen M, Torkkila E, Riikonen P (1994) Proteins 19:141-149 |
| 210 | Normalized flexibility parameters (B-values) | Vihinen M, Torkkila E, Riikonen P (1994) Proteins 19:141-149 |

FIG. 1K

| Index | Property Name | References |
|---|---|---|
| 211 | Free energy in alpha-helical conformation | Munoz V, Serrano L (1994) Proteins 20:301-311 |
| 212 | Free energy in alpha-helical region | Munoz V, Serrano L (1994) Proteins 20:301-311 |
| 213 | Free energy in beta-strand conformation | Munoz V, Serrano L (1994) Proteins 20:301-311 |
| 214 | Free energy in beta-strand region | Munoz V, Serrano L (1994) Proteins 20:301-311 |
| 215 | Free energy in beta-strand region | Munoz V, Serrano L (1994) Proteins 20:301-311 |
| 216 | Free energies of transfer of AcWl-X-LL peptides from bilayer | Wimley WC, White SH (1996) Nature Struct Biol 3:842-848 |
| 217 | Number of codon(s) | Most textbooks |
| 218 | Recognition factors | Fraga S (1982) Can J Chem 60:2606-2610 |
| 219 | Hydrophobicity scale | Eisenberg D, Schwarz E, Komaromy M, Wall R (1984) J Mol Biol 179:125-142 |
| 220 | Hydrophobicity scale | Abraham DJ, Leo AJ (1987) Proteins 2:130-152 |
| 221 | Hydrophobicity scale | Black SD, Mould DR (1991) Anal Biochem 193:72-82 |
| 222 | Hydrophobicity scale | Bull HB, Breese K (1974) Arch Biochem Biophys 161:665-670 |
| 223 | Hydrophobicity scale | Miyazawa S, Jernigan RL (1985) Macromolecules 18:534-552 |
| 224 | Hydrophobicity scale | Roseman MA (1988) J Mol Biol 200:513-522 |
| 225 | Hydrophobicity scale-HPLC | Wilson KJ, Honegger A, Stotzel RP, Hughes GJ (1981) Biochem J 199:31-41 |
| 226 | Normalized frequency of alpha region | Maxfield FR, Scheraga HA (1976) Biochemistry 15:5138-5153 |
| 227 | Hydrophobicity HPLC pH3.4 | Cowan R, Whittaker RG (1990) Peptide Research 3:75-80 |
| 228 | Hydrophobicity HPLC pH7.5 | Cowan R, Whittaker RG (1990) Peptide Research 3:75-80 |
| 229 | Hydrophobicity Rf mobility | Aboderin AA (1971) Int J Biochem 2:537-544 |
| 230 | % buried residues | Janin J (1979) Nature 277:491-492 |
| 231 | % accessible residues | Janin J (1979) Nature 277:491-492 |
| 232 | alpha-helix | Deleage G, Roux B (1987) Protein Eng 1:289-294 |
| 233 | beta-sheet | Deleage G, Roux B (1987) Protein Eng 1:289-294 |
| 234 | beta-turn | Deleage G, Roux B (1987) Protein Eng 1:289-294 |

FIG. 1L

| Index | Property Name | References |
|---|---|---|
| 235 | Coil | Deleage G, Roux B (1987) Protein Eng 1:289-294 |
| 236 | Amino acid composition | McCaldon P, Argos P (1988) Proteins 4:99-122 |
| 237 | Amino acid composition in SWISS-PROT | Release notes for SWISS-PROT release 38 - July 1999 |

FIG. 1M

| amino acids | Eigenvector : $E_i$ (Eigenvalue : $\lambda_i$) | | | | |
|---|---|---|---|---|---|
| | $E_1$(1961.504) | $E_2$(788.2) | $E_3$(539.776) | $E_4$(276.624) | $E_5$(244.106) |
| A | 0.008 | 0.134 | -0.475 | -0.039 | 0.181 |
| R | 0.171 | -0.361 | 0.107 | -0.258 | -0.364 |
| N | 0.255 | 0.038 | 0.117 | 0.118 | -0.055 |
| D | 0.303 | -0.057 | -0.014 | 0.225 | 0.156 |
| C | -0.132 | 0.174 | 0.07 | 0.565 | -0.374 |
| Q | 0.149 | -0.184 | -0.03 | 0.035 | -0.112 |
| E | 0.221 | -0.28 | -0.315 | 0.157 | 0.303 |
| G | 0.218 | 0.562 | -0.024 | 0.018 | 0.106 |
| H | 0.023 | -0.177 | 0.041 | 0.28 | -0.021 |
| I | -0.353 | 0.071 | -0.088 | -0.195 | -0.107 |
| L | -0.267 | 0.018 | -0.265 | -0.274 | 0.206 |
| K | 0.243 | -0.339 | -0.044 | -0.325 | -0.027 |
| M | -0.239 | -0.141 | -0.155 | 0.321 | 0.077 |
| F | -0.329 | -0.023 | 0.072 | -0.002 | 0.208 |
| P | 0.173 | 0.286 | 0.407 | -0.215 | 0.384 |
| S | 0.199 | 0.238 | -0.015 | -0.068 | -0.196 |
| T | 0.068 | 0.147 | -0.015 | -0.132 | -0.274 |
| W | -0.296 | -0.186 | 0.389 | 0.083 | 0.297 |
| Y | -0.141 | -0.057 | 0.425 | -0.096 | -0.091 |
| V | -0.274 | 0.136 | -0.187 | -0.196 | -0.299 |

FIG. 2

| Index | Members in cluster (total number) |
|---|---|
| 1 | GI, GV, IG, VG (4) |
| 2 | IR, KV, RI, RV, VK, VR (6) |
| 3 | LQ, LS, QL, SL (4) |
| 4 | IQ, QI (2) |
| 5 | IS, IT, LT, SI, SV, TI, TL, TV, VS, VT (10) |
| 6 | QV, VQ (2) |
| 7 | IK, KI, LR, RL (4) |
| 8 | DF, DW, FD, WD (4) |
| 9 | NW, WN (2) |
| 10 | RT, TR (2) |
| 11 | SS, ST, TS, TT (4) |
| 12 | CK, HR, KC, QT, RH, TQ (6) |
| 13 | KS, KT, NQ, QN, RS, SK, SR, TK (8) |
| 14 | GR, HS, NN, NS, NT, QS, RG, SH, SN, SQ, TN (11) |
| 15 | DR, HK, KH, KN, KQ, NK, NR, QK, QQ, QR, RD, RN, RQ (13) |
| 16 | KW, WK (2) |
| 17 | KY, RY, YK, YR (4) |
| 18 | RW, WR (2) |
| 19 | FR, RF (2) |
| 20 | FN, FP, GW, GY, HP, MP, NF, NY, PF, PH, PM, PW, PY, SW, TW, WG, WP, WS, WT, YG, YN, YP, YY (23) |
| 21 | IP, LP, PI, PL, PV, VP (6) |
| 22 | AA, AT, TA (3) |
| 23 | AP, PA (2) |
| 24 | AY, DV, FS, FT, IN, LN, NI, NL, NV, SF, TF, VD, VN, YA (14) |
| 25 | QY, SY, TY, YQ, YS, YT (6) |
| 26 | AI, AV, IA, VA (4) |
| 27 | AL, LA (2) |
| 28 | AF, FA (2) |
| 29 | MR, RM (2) |
| 30 | EF, EM, EW, FE, ME, WE (6) |
| 31 | FK, KF, KL, LK (4) |
| 32 | KM, MK, MQ, QM (4) |
| 33 | EI, EL, EV, IE, LE, VE (6) |
| 34 | CD, CN, DC, NC (4) |
| 35 | CE, EC (2) |
| 36 | AG, GA (2) |
| 37 | FM, MF, MW, WM (4) |
| 38 | WY, YW (2) |
| 39 | FW, WF, WW (3) |
| 40 | LW, WL (2) |
| 41 | EE (1) |

FIG. 3A

| Index | Members in cluster (total number) |
|---|---|
| 42 | DE, ED (2) |
| 43 | CI, CV, IC, VC (4) |
| 44 | CF, CL, FC, LC (4) |
| 45 | IY, LY, VY, YI, YL, YV (6) |
| 46 | CM, MC (2) |
| 47 | CC, CH, CW, CY, HC, WC, YC (7) |
| 48 | AS, SA (2) |
| 49 | EH, EK, EQ, ER, HE, KE, QE, RE (8) |
| 50 | AD, AK, AN, DA, ES, ET, KA, NA, SE, TE (10) |
| 51 | EG, GE (2) |
| 52 | AR, RA (2) |
| 53 | KP, PK, PQ, QP (4) |
| 54 | PR, RP (2) |
| 55 | DP, NP, PD, PN (4) |
| 56 | GP, PG, PP (3) |
| 57 | PS, PT, SP, TP (4) |
| 58 | AH, AQ, AW, DI, DL, FF, HA, HL, ID, LD, LH, QA, WA (13) |
| 59 | HI, HT, HV, IH, IM, MI, MT, MV, TH, TM, VH, VM (12) |
| 60 | AE, EA (2) |
| 61 | LM, ML (2) |
| 62 | AM, MA (2) |
| 63 | CP, PC (2) |
| 64 | CQ, CR, QC, RC (4) |
| 65 | MS, SM (2) |
| 66 | CG, GC (2) |
| 67 | AC, CA, CS, CT, GM, MG, SC, TC (8) |
| 68 | GL, LG (2) |
| 69 | FG, GF (2) |
| 70 | IL, LI, LL, LV, VL (5) |
| 71 | II, IV, VI, VV (4) |
| 72 | FI, FL, FV, IF, LF, VF (6) |
| 73 | GT, TG (2) |
| 74 | DS, DT, GK, GQ, KG, QG, SD, TD (8) |
| 75 | DK, KD (2) |
| 76 | GH, HG (2) |
| 77 | DQ, QD (2) |
| 78 | DG, GD, GG, GN, GS, NG, SG (7) |
| 79 | HN, NH (2) |
| 80 | HQ, QH (2) |
| 81 | FH, FQ, HF, HM, HW, MH, MM, MY, QF, QW, WH, WQ, YM (13) |
| 82 | DY, EY, HH, MN, NM, YD, YE (7) |
| 83 | DD, DH, DM, EN, HD, MD, NE (7) |
| 84 | HY, YH (2) |
| 85 | KK, KR, RK, RR (4) |
| 86 | FY, YF (2) |
| 87 | IW, VW, WI, WV (4) |
| 88 | EP, PE (2) |
| 89 | DN, ND (2) |

FIG. 3B

| Index | Members in cluster (total number) |
|---|---|
| 1 | CAA, CAC, CAD, CAE, CAG, CAH, CAK, CAN, CAP, CAQ, CAR, CAS, CAT, CCD, CCE, CCG, CCH, CCK, CCN, CCP, CCQ, CCR, CCS, CCT, CDH, CDL, CDM, CDV, CDY, CEH, CEM, CET, CEY, CGH, CGM, CGY, CHH, CHN, CHP, CHQ, CHS, CHT, CKY, CLN, CMN, CMS, CNN, CNV, CNY, CPQ, CPR, CPT, CPY, CRY, CSY, CTT (56) |
| 2 | CAI, CAL, CAV, CFV, CII, CIL, CIT, CIV, CLS, CLT, CLV, CTV, CVV, CVY (14) |
| 3 | CFG, CFP, CFS, CGI, CGL, CGV, CGW, CIN, CIP, CIS, CLP, CPV, CPW, CSV, CTY (15) |
| 4 | CFF, CFI, CFL, CFM, CFW, CFY, CIM, CIW, CIY, CLL, CLM, CLW, CLY, CMM, CMV, CMW, CVW, CWW, CWY (19) |
| 5 | CDD, CDN (2) |
| 6 | CCC, CCF, CCI, CCL, CCM, CCV, CCW, CCY (8) |
| 7 | CAF, CAM, CAW, CAY, CDF, CDI, CDW, CEF, CEI, CEL, CEV, CEW, CFH, CFK, CFN, CFQ, CFR, CFT, CHI, CHL, CHM, CHV, CHW, CHY, CIQ, CKM, CKW, CLQ, CMP, CMQ, CMR, CMT, CMY, CNW, CQV, CQW, CQY, CRW, CSW, CTW, CYY (41) |
| 8 | CIK, CIR, CKL, CKV, CLR, CRV (6) |
| 9 | GMW, GWW (2) |
| 10 | GCF, GCI, GCL, GCM, GCW, GMM (6) |
| 11 | GAF, GFF, GFI, GFL, GFM, GFV, GFW, GFY, GHI, GIM, GIW, GIY, GLM, GLW, GLY, GMV, GMY, GVW, GVY, GWY, GYY (21) |
| 12 | GAI, GII, GIL, GIV, GLL, GLV, GVV (7) |
| 13 | GAD, GAE, GAG, GAK, GAN, GAQ, GAS, GDE, GEE, GEG, GEH, GEK, GEN, GEQ, GER, GES, GET (17) |
| 14 | GAA, GAL (2) |
| 15 | GAC, GAH, GAR, GAT, GAV, GAY, GCC, GCD, GCE, GCG, GCH, GCK, GCN, GCP, GCQ, GCR, GCS, GCT, GCV, GCY, GDI, GDL, GDM, GDV, GEV, GFG, GFK, GFN, GFQ, GFR, GFS, GFT, GGI, GGL, GGM, GGV, GGW, GHH, GHM, GHT, GHV, GHY, GIK, GIN, GIP, GIQ, GIR, GIS, GIT, GKL, GKM, GKV, GLN, GLP, GLQ, GLR, GLS, GLT, GMN, GMP, GMQ, GMR, GMS, GMT, GNV, GPV, GQV, GQY, GRV, GRW, GSV, GSW, GSY, GTT, GTV, GTW, GTY (77) |
| 16 | GDP, GDY, GFP, GGP, GGY, GHP, GKP, GKW, GKY, GNP, GNY, GPP, GPQ, GPR, GPS, GPT, GPW, GPY, GRY, SGP, SPP (21) |
| 17 | GAM, GAW, GDF, GDW, GEF, GEI, GEL, GEM, GEW, GEY, GFH, GHL, GHW, GNW, GQW (15) |
| 18 | GAP, GDD, GDG, GDH, GDK, GDN, GDQ, GDR, GDS, GDT, GEP, GGG, GGH, GGK, GGN, GGQ, GGR, GGS, GGT, GHK, GHN, GHQ, GHR, GHS, GKK, GKN, GKQ, GKR, GKS, GKT, GNN, GNQ, GNR, GNS, GNT, GQQ, GQR, GQS, GQT, GRS, GRT, GSS, GST, SGG (44) |
| 19 | WKR, WNR, WQR, WRR, WRS, WRT (6) |
| 20 | WFR, WKK (2) |
| 21 | WDK, WDQ, WDR, WDS, WDT, WGG, WGK, WGN, WGQ, WGR, WGS, WGT, WHK, WKN, WKQ, WKS, WKT, WNQ, WNS, WNT, WQQ, WQS, WSS, WST (24) |

FIG. 4A

| Index | Members in cluster (total number) |
|---|---|
| 22 | VCC, VCD, VCG, VCH, VCI, VCN, VCQ, VCR, VCS, VCT, VCV (11) |
| 23 | VCE, VDD, VDH, VDM, VDN, VEH, VEM, VFH, VFM, VHH, VHM, VHN, VHQ, VMM, VMN, VMQ (16) |
| 24 | ICC, ICT, ICV, ISV, ITV, IVV, VCF, VCM, VCW, VCY, VFI, VFV, VIM, VIY, VLL, VLY, VMV, VVW, VVY (19) |
| 25 | ICG, ICS, ISS, IST, TII, TIL, TIV, VCP, VDP, VDY, VGP, VGW, VGY, VHP, VIP, VKP, VNN, VNP, VPQ, VPR, VPS, VPT (22) |
| 26 | VIK, VIR, VKL, VKV, VLR, VRV (6) |
| 27 | VAD, VAE, VAG, VAN, VDE, VDG, VEE, VEG, VEK, VEN, VEQ, VES (12) |
| 28 | ITT, VAA, VAC, VAF, VAH, VAI, VAK, VAL, VAM, VAP, VAQ, VAR, VAS, VAT, VAV, VAW, VAY, VCK, VCL, VDF, VDI, VDL, VDV, VEF, VEI, VEL, VET, VEV, VEY, VFG, VFK, VFN, VFQ, VFR, VFS, VFT, VGH, VGI, VGL, VGM, VGV, VHI, VHL, VHR, VHS, VHT, VHV, VHY, VIN, VIQ, VIS, VIT, VKM, VKY, VLM, VLN, VLP, VLQ, VLS, VLT, VMP, VMR, VMS, VMT, VMY, VNV, VNY, VPV, VQT, VQV, VQY, VRT, VRW, VRY, VSV, VSW, VSY, VTT, VTV, VTW, VTY, VYY (82) |
| 29 | VDK, VDQ, VDR, VDS, VDT, VER, VGG, VGK, VGN, VGQ, VGR, VGS, VGT, VHK, VKN, VKQ, VKS, VKT, VNQ, VNR, VNS, VNT, VQQ, VQR, VQS, VRS, VSS, VST (28) |
| 30 | VKK, VKR, VRR (3) |
| 31 | ECF, ECI, ECL, ECM, ECV, ECW, ECY, EIY, EMV, EVY (10) |
| 32 | EDD, EDG, EDK, EDN, EGK, ENN, ENR (7) |
| 33 | EFI, EFL, EFV, EII, EIL, EIV, ELL, ELV, EVV (9) |
| 34 | EAD, EAE, EAG, EAK, EAN, EAS, EDE, EEE, EEG, EEH, EEK, EEN, EEQ, EER, EES, EET (16) |
| 35 | EDP, EEP, EGP, EKP, ENP, EPP, EPQ, EPR, EPS, EPT (10) |
| 36 | ECE, EDM, EHM, EMM (4) |
| 37 | EFF, EFM, EFW, EFY, EIM, EIW, ELM, ELW, EMW, EVW, EWW, EWY (12) |
| 38 | EIK, EIR, EKV, ELR, ERV (5) |
| 39 | EAA, EAC, EAF, EAH, EAI, EAL, EAM, EAP, EAQ, EAR, EAT, EAV, EAW, EAY, ECP, EDF, EDI, EDL, EDV, EDW, EDY, EEF, EEI, EEL, EEM, EEV, EEW, EEY, EFG, EFH, EFK, EFN, EFP, EFQ, EFR, EFS, EFT, EGI, EGL, EGM, EGV, EGW, EGY, EHI, EHL, EHP, EHV, EHW, EHY, EIN, EIP, EIQ, EIS, EIT, EKL, EKM, EKW, EKY, ELN, ELP, ELQ, ELS, ELT, ELY, EMN, EMP, EMQ, EMS, EMT, EMY, ENV, ENW, ENY, EPV, EPW, EPY, EQV, EQW, EQY, ERW, ERY, ESV, ESW, ESY, ETV, ETW, ETY, EYY (88) |
| 40 | FIR, FRV (2) |
| 41 | FHR, FKR, FNR, FQR, FRR, FRS, FRT (7) |
| 42 | FCC, FCI, FCM, FCV (4) |
| 43 | FCD, FCG, FCK, FDH, FDN, FDQ, FDR, FDS, FDT, FGG, FGH, FGN, FGQ, FGR, FGS, FGT, FHH, FHK, FHN, FHQ, FHS, FHT, FIS, FKK, FKN, FKQ, FKS, FKT, FMN, FMR, FNQ, FNS, FNT, FNV, FQQ, FQS, FQT, FSS, FST, FTT, MPP, MPW, MPY (43) |
| 44 | FCH, FCN, FCQ, FCR, FCS, FCT (6) |
| 45 | CDE, CDG, CEE, CEG, CEK, CEN, CEQ, CES, CGG, CGN, HCC (11) |
| 46 | CDP, CEP, CGP, CKP, CNP, CPP, CPS (7) |

FIG. 4B

| Index | Members in cluster (total number) |
|---|---|
| 47 | MDF, MDW, MEF, MEW, MMP, MNW (6) |
| 48 | MAA, MAD, MAE, MAF, MAL, MAM, MAW, MDL, MEL, MLM (10) |
| 49 | MFF, MFL, MFM, MFW, MLW (5) |
| 50 | MHW, MMW, MWW, MWY (4) |
| 51 | MDE, MEE, MEM (3) |
| 52 | IKK, IKR, IRR (3) |
| 53 | ICD, ICH, ICK, ICN, ICQ, ICR, IDH, IDN, IDR, IGH, IGN, IGR, IHH, IHK, IHN, IHQ, IHR, IHS, IHT, IKN, INN, INQ, INR, INS, INT, IQR, IRS, IRT, VDW, VFP, VHW, VNW, VQW (33) |
| 54 | IAD, IAG, IAH, IAK, IAN, IAQ, IAR, IAS, ICE, IDE, IDM, IEG, IEH, IEK, IEM, IEN, IEQ, IER, IES, IET, LCC, VEP, VEW (23) |
| 55 | IAF, IAI, IAL, IAV, IFT, IFV, III, IIL, IIT, IIV, ILL, ILT, ILV, VFF, VFL, VIW, VLW (17) |
| 56 | IAP, IDD, IDG, IDK, IDQ, IDS, IDT, IGG, IGK, IGQ, IGS, IGT, IKQ, IKS, IKT, IQQ, IQS, IQT, VKW (19) |
| 57 | FVV, IAM, IAW, ICF, ICI, ICL, ICM, ICW, ICY, IFF, IFH, IFI, IFL, IFM, IFW, IFY, IHI, IHL, IHM, IHV, IHW, IIM, IIW, IIY, ILM, ILW, ILY, IMM, IMV, IMW, IMY, ITW, IVW, IVY, IWW, IWY, IYY, VFW, VMW, VWW (40) |
| 58 | FTV, IAA, IAC, IAT, IAY, ICP, IDF, IDI, IDL, IDV, IDW, IDY, IEF, IEI, IEL, IEV, IEW, IEY, IFG, IFK, IFN, IFP, IFQ, IFR, IFS, IGI, IGL, IGM, IGV, IGW, IGY, IHY, IIK, IIN, IIP, IIQ, IIR, IIS, IKL, IKM, IKV, IKW, IKY, ILN, ILP, ILQ, ILR, ILS, IMN, IMP, IMQ, IMR, IMS, IMT, INV, INW, INY, IPV, IPW, IPY, IQV, IQW, IQY, IRV, IRW, IRY, ISW, ISY, ITY, LCY, VFY, VWY (72) |
| 59 | IDP, IEP, IGP, IHP, IKP, INP, IPP, IPQ, IPR, IPS, IPT, VPP, VPW, VPY (14) |
| 60 | PKK, PKR, PRR (3) |
| 61 | PRS, PRT (2) |
| 62 | PDK, PDQ, PDR, PDS, PDT, PER, PGG, PGK, PGN, PGQ, PGR, PGS, PGT, PHK, PKN, PKQ, PKS, PKT, PNQ, PNR, PNS, PNT, PQQ, PQR, PQS, PSS, PST (27) |
| 63 | HIK, HIR, HKV, HLR, HRV (5) |
| 64 | HDG, HGN, NMM (3) |
| 65 | HII, HIL, HIV, HLV, HVV, MRR (6) |
| 66 | HDK, HDQ, HDR, HDS, HDT, HER, HGK, HGQ, HGR, HGT, HHK, HHR, HKN, HKQ, HKS, HKT, HNQ, HNR, HNS, HNT, HQQ, HQR, HQS, HQT, HRS, HRT, HSS, HST, QCH (29) |
| 67 | HAC, HAF, HAH, HAI, HAK, HAM, HAN, HAP, HAQ, HAR, HAS, HAT, HAV, HAW, HAY, HCD, HCE, HCF, HCG, HCH, HCI, HCK, HCL, HCM, HCN, HCP, HCQ, HCR, HCS, HCT, HCV, HCW, HCY, HDD, HDF, HDH, HDI, HDL, HDM, HDN, HDP, HDV, HDW, HDY, HEI, HEP, HET, HEV, HEY, HFG, HFH, HFN, HFP, HFQ, HFR, HFS, HFT, HFV, HGH, HGM, HGW, HGY, HHH, HHI, HHL, HHM, HHN, HHP, HHQ, HHS, HHT, HHV, HHW, HHY, HIN, HIP, HIQ, HIT, HIY, HKP, HKY, HLN, HLP, HLQ, HLT, HLY, HMM, HMN, HMP, HMR, HMS, HMT, HMV, HMY, HNN, HNP, HNV, HNW, HNY, HPQ, HPR, HPT, HPV, HPW, HPY, HQY, HRY, HSW, HSY, HTT, HTW, HTY, HVY, HYY, QCC, QCF, QCM, QCW, QHW, QMM (120) |

FIG. 4C

| Index | Members in cluster (total number) |
|---|---|
| 68 | HFF, HFI, HFL, HFM, HFW, HFY, HIM, HIW, HLW, HMW, HVW, HWW, HWY (13) |
| 69 | HGI, HGL, HGV, HIS, HLS, HQV, HSV, HTV (8) |
| 70 | HEF, HEL, HEM, HEW, HFK, HKL, HKM, HKW, HMQ, HQW, HRW, QFW, QMW, QWW (14) |
| 71 | HAD, HAE, HAG, HDE, HEE, HEG, HEH, HEK, HEN, HEQ, HES (11) |
| 72 | WAD, WAE, WAG, WDD, WDE, WDG, WEE, WEG, WEH, WEK, WEN, WEQ, WES (13) |
| 73 | FWW, WFI, WFL, WFV, WII, WIL, WIV, WLL, WLV (9) |
| 74 | WIK, WIR, WKL, WKV, WLR, WRV (6) |
| 75 | WAP, WGI, WGL, WGV, WIS, WIT, WLS, WSV, WTT, WTV (10) |
| 76 | WCC, WCD, WCF, WCG, WCH, WCI, WCM, WCN, WCQ, WCR, WCS, WCT, WCV (13) |
| 77 | WDP, WEP, WGP, WKP, WNP, WPP, WPQ, WPR, WPS, WPT (10) |
| 78 | WAC, WAF, WAH, WAI, WAK, WAL, WAM, WAN, WAQ, WAR, WAS, WAT, WAW, WAY, WCE, WCK, WCL, WCP, WCW, WCY, WDF, WDH, WDI, WDL, WDM, WDN, WDV, WDW, WDY, WEF, WEI, WEL, WEM, WET, WEV, WEW, WEY, WFF, WFH, WFK, WFM, WFN, WFQ, WFR, WFS, WFT, WFW, WFY, WGH, WGM, WGY, WHH, WHI, WHL, WHM, WHN, WHP, WHQ, WHR, WHS, WHT, WHV, WHW, WHY, WIM, WIN, WIQ, WIW, WIY, WKM, WKW, WKY, WLM, WLN, WLQ, WLT, WLW, WLY, WMM, WMN, WMP, WMQ, WMR, WMS, WMT, WMV, WMW, WMY, WNN, WNV, WNW, WNY, WPY, WQT, WQV, WQW, WQY, WRW, WRY, WSW, WSY, WTW, WTY, WVW, WVY, WWW, WWY, WYY (108) |
| 79 | WFG, WFP, WGW, WIP, WLP, WPV, WPW (7) |
| 80 | ACC, ACI, ACM, ACV (4) |
| 81 | ACD, ACG, ACH, ACN, ACQ, ACS, ACT (7) |
| 82 | CHR, CKR, CNR, CQR, CRR, CRS, CRT (7) |
| 83 | CDK, CDQ, CDR, CDS, CDT, CER, CGK, CGQ, CGR, CGS, CGT, CHK, CKK, CKN, CKQ, CKS, CKT, CNQ, CNS, CNT, CQQ, CQS, CQT, CSS, CST (25) |
| 84 | RFF, RFM, RFW, RFY, RIM, RIW, RIY, RLM, RLW, RMV, RVW, RWW, RWY (13) |
| 85 | RFI, RFL, RFV, RII, RIL, RIV, RLL, RLV (8) |
| 86 | TWW, YAA, YAC, YAE, YAF, YAH, YAI, YAK, YAL, YAM, YAN, YAP, YAQ, YAR, YAS, YAT, YAV, YAW, YAY, YCE, YCF, YCI, YCK, YCL, YCM, YCP, YCV, YCW, YCY, YDF, YDI, YDL, YDM, YDV, YDW, YDY, YEF, YEI, YEL, YEM, YET, YEV, YEW, YEY, YFG, YFH, YFK, YFN, YFP, YFQ, YFR, YFS, YFT, YGH, YGI, YGL, YGM, YGV, YGW, YGY, YHH, YHI, YHL, YHM, YHN, YHP, YHQ, YHT, YHV, YHW, YHY, YIN, YIP, YIQ, YIS, YIY, YKL, YKM, YKW, YKY, YLN, YLP, YLQ, YLY, YMM, YMN, YMP, YMQ, YMR, YMS, YMT, YMV, YMY, YNV, YNW, YNY, YPT, YPV, YPW, YPY, YQV, YQW, YQY, YRW, YRY, YSV, YSW, YSY, YTT, YTW, YTY, YVY, YWY, YYY (114) |

FIG. 4D

| Index | Members in cluster (total number) |
|---|---|
| 87 | YII, YIL, YIT, YIV, YLS, YLT, YLV, YTV, YVV (9) |
| 88 | YDP, YEP, YGP, YKP, YNP, YPP, YPQ, YPR, YPS (9) |
| 89 | YCC, YCD, YCG, YCH, YCN, YCQ, YCR, YCS, YCT (9) |
| 90 | YDK, YDR, YDS, YDT, YER, YGK, YGN, YGQ, YGR, YGS, YGT, YHK, YHR, YHS, YKK, YKN, YKQ, YKR, YKS, YKT, YNN, YNQ, YNR, YNS, YNT, YQQ, YQR, YQS, YQT, YRR, YRS, YRT, YSS, YST (34) |
| 91 | YAD, YAG, YDD, YDE, YDG, YDH, YDN, YDQ, YEE, YEG, YEH, YEK, YEN, YEQ, YES, YGG (16) |
| 92 | YFF, YFI, YFL, YFM, YFV, YFW, YFY, YIM, YIW, YLL, YLM, YLW, YMW, YVW, YWW (15) |
| 93 | YIK, YIR, YKV, YLR, YRV (5) |
| 94 | NII, NIV, NVV, SHW, SMW (5) |
| 95 | GRR, SDD, SDE, SDG, SDK, SDN, SDP, SDQ, SEG, SEK, SEN, SEP, SEQ, SER, SES, SGK, SGN, SKP, SNN, SNP, SPS (21) |
| 96 | THR, TKR, TNR, TQR, TRR, TRS, TRT (7) |
| 97 | SII, SIL, SIV, SLL, SLV, SVV, TAI, TAL, TAT, TAV, TGI, TGL, TGV, TIS, TIT, TLS, TSV, TTT, TTV, TVV (20) |
| 98 | QGV, TEH, TEM (3) |
| 99 | SDH, SDR, SDS, SDT, SGH, SGQ, SGR, SGS, SGT, SHK, SHQ, SHS, SKK, SKN, SKQ, SKS, SKT, SNQ, SNS, SNT, SQQ, SQS, SQT, SSS, SST, STT (26) |
| 100 | NLV, NTV, SAA, SAC, SAD, SAE, SAF, SAG, SAH, SAI, SAK, SAL, SAM, SAN, SAP, SAQ, SAR, SAS, SAT, SAV, SAW, SAY, SCE, SCL, SCP, SCW, SCY, SDF, SDI, SDL, SDM, SDV, SDY, SEF, SEH, SEI, SEL, SEM, SET, SEV, SEY, SFG, SFH, SFK, SFN, SFP, SFQ, SFR, SFS, SFT, SGI, SGL, SGM, SGV, SGW, SGY, SHH, SHI, SHL, SHM, SHN, SHP, SHR, SHT, SHV, SHY, SIN, SIP, SKL, SKM, SKW, SKY, SLM, SLN, SLP, SLQ, SLS, SLT, SLY, SMM, SMN, SMP, SMQ, SMS, SMT, SMY, SNW, SNY, SPQ, SPR, SPT, SPV, SPW, SPY, SQW, SQY, SRW, SRY, SSW, SSY, STW, STY, SWY, SYY, TAD, TAE, TAG, TAK, TAN, TAP, TAS, TDD, TDE, TDG, TDH, TDN, TDP, TEE, TEG, TEK, TEN, TEP, TEQ, TES, TET, TGG, TGH, TGN, TGP, THN, THP, TKP, TNN, TNP, TPP, TPQ, TPR, TPS, TPT (139) |
| 101 | SCC, SCD, SCF, SCG, SCH, SCI, SCK, SCM, SCN, SCQ, SCR, SCS, SCT, SCV, TCC, TCD, TCF, TCG, TCH, TCI, TCM, TCN, TCQ, TCS, TCT, TCV (26) |
| 102 | SKR, SNR, SQR, SRR, SRS, SRT (6) |
| 103 | SFF, SFI, SFL, SFM, SFV, SFW, SFY, SIM, SIW, SIY, SLW, SMV, SVW, SVY, TAA, TAC, TAF, TAH, TAM, TAQ, TAR, TAW, TAY, TCE, TCK, TCL, TCP, TCR, TCY, TDF, TDI, TDL, TDM, TDV, TDW, TDY, TEF, TEI, TEL, TEV, TEW, TEY, TFG, TFH, TFK, TFN, TFP, TFQ, TFR, TFS, TFT, TGM, TGW, TGY, THH, THI, THL, THM, THQ, THT, THV, THW, THY, TIK, TIN, TIP, TIQ, TIR, TKL, TKM, TKV, TKW, TKY, TLN, TLP, TLQ, TLR, TLT, TMN, TMP, TMQ, TMR, TMS, TMT, TNV, TNW, TNY, TPV, TPW, TPY, TQV, TQW, TQY, TRV, TRW, TRY, TSW, TSY, TTW, TTY, TYY (101) |

FIG. 4E

| Index | Members in cluster (total number) |
|---|---|
| 104 | SIK, SIQ, SIR, SIS, SIT, SKV, SLR, SMR, SNV, SQV, SRV, SSV, STV, TDK, TDQ, TDR, TDS, TDT, TER, TGK, TGQ, TGR, TGS, TGT, THK, THS, TKK, TKN, TKQ, TKS, TKT, TNQ, TNS, TNT, TQQ, TQS, TQT, TSS, TST (39) |
| 105 | TCW, TFF, TFI, TFL, TFM, TFV, TFW, TFY, TIM, TIW, TIY, TLL, TLM, TLV, TLW, TLY, TMM, TMV, TMW, TMY, TVW, TVY, TWY (23) |
| 106 | PCC, PCD, PCF, PCG, PCH, PCI, PCM, PCN, PCQ, PCS, PCT, PCV (12) |
| 107 | PAD, PAE, PAG, PAN, PDD, PDE, PDG, PDN, PEE, PEG, PEH, PEK, PEN, PEQ, PES (15) |
| 108 | PAA, PAI, PAL, PAP, PAS, PAT, PAV, PGI, PGL, PGV, PGY, PIP, PIS, PIT, PLS, PPT, PPV, PPY, PSV, PTT, PTV (21) |
| 109 | PFF, PFI, PFM, PFW, PFY, PIM, PIW, PLM, PLW, PMW, PVW, PWW, PWY (13) |
| 110 | PDP, PEP, PGP, PKP, PNP, PPP, PPQ, PPR, PPS (9) |
| 111 | PAC, PAF, PAH, PAK, PAM, PAQ, PAR, PAW, PAY, PCE, PCK, PCL, PCP, PCR, PCW, PCY, PDF, PDH, PDI, PDL, PDM, PDV, PDW, PDY, PEF, PEI, PEL, PEM, PET, PEV, PEW, PEY, PFG, PFH, PFK, PFN, PFQ, PFR, PFS, PFT, PGH, PGM, PGW, PHH, PHI, PHL, PHM, PHN, PHP, PHQ, PHR, PHS, PHT, PHV, PHW, PHY, PIK, PIN, PIQ, PIR, PIY, PKL, PKM, PKV, PKW, PKY, PLN, PLQ, PLR, PLT, PLY, PMM, PMN, PMP, PMQ, PMR, PMS, PMT, PMV, PMY, PNN, PNV, PNW, PNY, PQT, PQV, PQW, PQY, PRV, PRW, PRY, PSW, PSY, PTW, PTY, PVY, PYY (97) |
| 112 | PFP, PLP, PPW (3) |
| 113 | PFL, PFV, PII, PIL, PIV, PLL, PLV, PVV (8) |
| 114 | AIK, AIR, AKL, AKV, ALR, ARV (6) |
| 115 | AFV, AII, AIL, AIV, ALV (5) |
| 116 | ACP, ADW, ADY, AGW, AHP, AHW, AHY, AKW, AKY, ANW, ANY, AQW, AQY, ARW, ARY, ASW, ASY, ATW, ATY (19) |
| 117 | AAC, AAD, AAE, AAF, AAH, AAK, AAM, AAN, AAQ, AAR, AAS, AAW, AAY, ACE, ACK, ACL, ACR, ADD, ADE, ADF, ADH, ADI, ADL, ADM, ADN, ADV, AEE, AEF, AEG, AEH, AEI, AEK, AEL, AEM, AEN, AEP, AEQ, AES, AET, AEV, AEW, AEY, AFH, AFK, AFN, AFQ, AFR, AFS, AFT, AGH, AGM, AHH, AHI, AHL, AHM, AHN, AHQ, AHR, AHS, AHT, AHV, AIN, AIQ, AKM, ALN, ALP, ALQ, AMM, AMN, AMP, AMQ, AMR, AMS, AMT, AMV, AMY, ANN, ANV, AQV (79) |
| 118 | AAI, AAL, AAT, AAV, AIS, AIT, ALS, ALT, ASV, ATT, ATV, AVV (12) |
| 119 | AFF, AFI, AFL, AFM, AFW, AFY, AIM, AIW, ALL, ALM, ALW, ALY, AMW, AVW, AWW, AWY (16) |
| 120 | ADP, AKP, APQ, APR (4) |
| 121 | ACF, ACW, ACY, AIY, AVY, AYY (6) |
| 122 | RAA, RAY, RDI, RDL, REI, REL, REV, REW, RFG, RFK, RFN, RFP, RFS, RGI, RGL, RGM, RGV, RGW, RIP, RKL, RKM, RKW, RLN, RLP, RLQ, RLS, RMP, RNW, RPV, RPW, RPY, RQW, RRW, RSW (34) |
| 123 | RAC, RAR, RAT, RCD, RCE, RCF, RCG, RCH, RCK, RCL, RCM, RCN, RCP, RCQ, RCR, RCW, RCY, RDV, RDY, RFQ, RFR, RFT, RGY, RHH, RHI, RHN, RHQ, RHT, RHV, RHY, RIK, RIN, RIQ, RIR, RIS, RIT, RKV, RKY, RLR, RLT, RLY, RMN, RMQ, RMR, RMS, RMT, RMY, RNV, RNY, RQV, RQY, RRV, RRY, RSY, RTW, RTY, RVY, RYY (58) |

FIG. 4F

| Index | Members in cluster (total number) |
|---|---|
| 124 | RAI, RAL, RAV (3) |
| 125 | RCC, RCI, RCS, RCT, RCV, RSV, RTT, RTV, RVV (9) |
| 126 | RAE, RAF, RAH, RAM, RAW, RDD, RDE, RDF, RDH, RDM, RDN, RDW, REF, REH, REM, REN, REY, RFH, RHL, RHM, RHW, RMM, RMW (23) |
| 127 | RAP, RDP, REP, RGP, RHP, RKP, RNP, RPP, RPQ, RPR, RPS, RPT (12) |
| 128 | KCR, QKR, QRR, RAD, RAG, RAK, RAN, RAQ, RAS, REE, REG, REK, REQ, RES, RET (15) |
| 129 | RDG, RDK, RDQ, RDR, RDS, RDT, RER, RGG, RGH, RGK, RGN, RGQ, RGR, RGS, RGT, RHK, RHR, RHS, RKK, RKN, RKQ, RKR, RKS, RKT, RNN, RNQ, RNR, RNS, RNT, RQQ, RQR, RQS, RQT, RRR, RRS, RRT, RSS, RST (38) |
| 130 | LCI, LCL, LCV, LIT, LIV, LTV, LVV (7) |
| 131 | IAE, IEE, LCD, LCG, LCH, LCK, LCN, LCQ, LCR, LCS, LCT, LHH (12) |
| 132 | LFF, LFI, LFL, LFV, LFY, LII, LIL, LIM, LIW, LIY, LLL, LLM, LLV, LLW, LLY, LMV, LVW, LVY (18) |
| 133 | LDW, LFH, LFM, LFW, LHW, LMW, LMY, LNW, LQW, LWW, LWY (11) |
| 134 | LCF, LCM, LCW (3) |
| 135 | LDG, LDK, LDN, LDQ, LDR, LDS, LDT, LER, LGG, LGH, LGK, LGN, LGQ, LGR, LGS, LGT, LHK, LHN, LHQ, LHR, LHS, LKK, LKN, LKQ, LKR, LKS, LKT, LNN, LNQ, LNR, LNS, LNT, LQQ, LQR, LQS, LQT, LRR, LRS, LRT, LSS, LST (41) |
| 136 | LAA, LAC, LAF, LAG, LAI, LAL, LAP, LAR, LAS, LAT, LAV, LAW, LAY, LCP, LDF, LDI, LDL, LDV, LDY, LEI, LEL, LEV, LEW, LEY, LFG, LFK, LFN, LFP, LFQ, LFR, LFS, LFT, LGI, LGL, LGM, LGV, LGW, LGY, LHI, LHL, LHP, LHT, LHV, LHY, LIK, LIN, LIP, LIQ, LIR, LIS, LKL, LKM, LKV, LKW, LKY, LLN, LLP, LLQ, LLR, LLS, LLT, LMP, LMR, LMS, LMT, LNV, LNY, LPV, LPW, LPY, LQV, LQY, LRV, LRW, LRY, LSV, LSW, LSY, LTT, LTW, LTY, LYY (82) |
| 137 | LDP, LEP, LGP, LKP, LNP, LPP, LPQ, LPR, LPS, LPT (10) |
| 138 | LAD, LAE, LAH, LAK, LAM, LAN, LAQ, LCE, LDD, LDE, LDH, LDM, LEE, LEF, LEG, LEH, LEK, LEM, LEN, LEQ, LES, LET, LHM, LMM, LMN, LMQ (26) |
| 139 | DRY, NDG, NDK, NDN, NDP, NDQ, NDR, NDS, NDT, NEG, NEK, NEN, NEP, NEQ, NER, NES, NGG, NGH, NGK, NGN, NGP, NGQ, NGR, NGS, NGT, NHK, NHR, NKN, NKQ, NKS, NNN, NNP, NNQ, NNR, NNS, NNT, NPQ, NQQ, NQR, NQS, NRS, NSS, NST (43) |
| 140 | NCC, NCV (2) |
| 141 | NIK, NIR, NKK, NKL, NKR, NKT, NKV, NKY, NLR, NRR, NRT, NRV, NRY, QDP, QGY, QNP, QPP, QPS, QPT, QPW, QPY (21) |
| 142 | NAA, NAG, NAL, NAP, NAS, NAT, NAV, NFG, NFP, NGI, NGL, NGV, NGY, NIP, NIS, NLP, NLS, NPP, NPS, NPT, NPV, NPW, NPY, NSV, NSY, NTT, QGG, SDW, SEE (29) |
| 143 | DYY, HPP, NFW, NHW, NMW, NWW (6) |
| 144 | DRV, QDG (2) |
| 145 | DTV, DVV, DVY, HGG, HGP, HGS, HPS, NAC, NAD, NAF, NAH, NAI, NAK, NAM, NAN, NAQ, NAR, NAW, NAY, NCE, NCF, NCI, NCL, NCM, NCP, NCW, NCY, NDD, NDF, NDH, NDI, NDL, NDM, NDV, NDW, NDY, NEI, NET, NEV, NEY, NFF, NFH, NFI, NFK, NFL, NFM, NFN, NFQ, NFR, NFS, NFT, NFV, NFY, NGM, NGW, NHI, NHL, NHM, NHN, NHP, NHQ, NHS, NHT, NHV, NHY, NIL, NIM, NIN, NIQ, NIT, NIW, NIY, NKM, NKP, NKW, NLL, NLM, NLN, NLQ, NLT, NLW, NLY, NMN, NMP, NMQ, NMR, NMS, NMT, NMV, NMY, NNV, NNW, NNY, NPR, NQT, NQV, NQW, NQY, NRW, NSW, NTW, NTY, NVW, NVY, NWY, NYY, QCG, QCP, QGN, QGP, QGS, QGT, QGW, SEW, SWW (115) |

FIG. 4G

| Index | Members in cluster (total number) |
|---|---|
| 146 | NCD, NCG, NCH, NCK, NCN, NCQ, NCR, NCS, NCT, NHH (10) |
| 147 | DAA, DDF, DDW, DEF, DEL, DEM, DEW, DFG, DFP, DGL, DGW, DKW, DLP, DMP, DNW, DPW, DPY (17) |
| 148 | DAC, DAD, DAF, DAG, DAH, DAK, DAM, DAN, DAP, DAQ, DAR, DAS, DAT, DAW, DAY, DCE, DCG, DCK, DCL, DCP, DCR, DCY, DDD, DDG, DDH, DDI, DDK, DDL, DDM, DDN, DDQ, DDR, DDS, DDT, DDV, DDY, DEG, DEH, DEI, DEK, DEN, DEQ, DER, DES, DET, DEV, DEY, DFH, DFK, DFN, DFQ, DFR, DFS, DFT, DGH, DGI, DGK, DGM, DGN, DGQ, DGR, DGT, DGV, DGY, DHH, DHI, DHK, DHL, DHM, DHN, DHP, DHQ, DHR, DHS, DHT, DHV, DHW, DHY, DIK, DIN, DIP, DIQ, DIR, DIS, DKK, DKL, DKM, DKN, DKQ, DKR, DKS, DKT, DKV, DKY, DLN, DLQ, DLR, DLS, DMN, DMQ, DMR, DMS, DMT, DMV, DMY, DNN, DNQ, DNR, DNS, DNT, DNV, DNY, DPQ, DPR, DPT, DPV, DQQ, DQR, DQS, DQT, DQV, DQW, DQY, DRS, DRT, DRW, DSS, DST, DSV, DSW, DSY, DTT, DTW, DTY, NAE, NDE, NEE, NEF, NEH, NEM, NEW (141) |
| 149 | DAE, DDE, DEE (3) |
| 150 | DCC, DCD, DCF, DCH, DCI, DCM, DCN, DCQ, DCS, DCT, DCV (11) |
| 151 | DDP, DEP, DGG, DGP, DGS, DKP, DNP, DPP, DPS (9) |
| 152 | DAI, DAL, DAV, DFI, DFV, DII, DIL, DIT, DIV, DLL, DLT, DLV, NEL (13) |
| 153 | DCW, DFF, DFL, DFM, DFW, DFY, DIM, DIW, DIY, DLM, DLW, DLY, DMM, DMW, DVW, DWW, DWY (17) |
| 154 | VII, VIL, VIV, VLV, VVV (5) |
| 155 | HLL, MDD, MDG, MDH, MDK, MDN, MDQ, MDR, MDS, MDT, MEP, MER, MGG, MGH, MGK, MGN, MGQ, MGR, MGS, MGT, MHK, MHN, MHR, MHS, MKK, MKN, MKQ, MKR, MKS, MKT, MNN, MNQ, MNR, MNS, MNT, MQQ, MQR, MQS, MQT, MRS, MRT, MSS, MST (43) |
| 156 | MAG, MAH, MAK, MAN, MAQ, MAS, MEG, MEH, MEK, MEN, MEQ, MES, MET (13) |
| 157 | MFI, MFV, MFY, MIL, MIM, MIW, MIY, MLL, MLY, MMV, MVW, MVY, MYY (13) |
| 158 | MCC, MCF, MCI, MCL, MCM, MCV, MCW, MCY (8) |
| 159 | HLM, MCP, MDP, MDY, MFP, MGP, MGW, MGY, MHP, MHY, MIP, MKP, MKW, MKY, MNP, MNY, MPQ, MPR, MPS, MPT, MQW, MQY, MRW, MRY, MSW, MSY, MTW, MTY (28) |
| 160 | MAI, MAV, MII, MIT, MIV, MLS, MLT, MLV, MTV, MVV (10) |
| 161 | MAC, MAP, MAR, MAT, MAY, MCD, MCE, MCG, MCH, MCK, MCN, MCQ, MCR, MCS, MCT, MDI, MDM, MDV, MEI, MEV, MEY, MFG, MFH, MFK, MFN, MFQ, MFR, MFS, MFT, MGI, MGL, MGM, MGV, MHH, MHI, MHL, MHM, MHQ, MHT, MHV, MIK, MIN, MIQ, MIR, MIS, MKL, MKM, MKV, MLN, MLP, MLQ, MLR, MMM, MMN, MMQ, MMR, MMS, MMT, MMY, MNV, MPV, MQV, MRV, MSV, MTT (65) |
| 162 | HAA, HAL (2) |
| 163 | AKT, ANR, ANT, AQR, AQT, ARS, ART, AST (8) |
| 164 | AKK, AKR, ARR (3) |
| 165 | ADG, ADK, ADQ, ADR, ADS, ADT, AER, AGG, AGK, AGN, AGQ, AGR, AGS, AGT, AHK, AKN, AKQ, AKS, ANQ, ANS, AQQ, AQS, ASS (23) |

FIG. 4H

| Index | Members in cluster (total number) |
|---|---|
| 166 | AGI, AGL, AGV (3) |
| 167 | AAA, AAG, AFG (3) |
| 168 | AAP, AFP, AGP, AGY, AIP, ANP, APP, APS, APT, APV, APW, APY (12) |
| 169 | QFG, QFP, QGI, QGL, QIP, QLP, QPV (7) |
| 170 | KCC, KCG, KCH, QDH, QDQ, QDR, QDS, QDT, QGH, QGK, QGQ, QGR, QHK, QHN, QHQ, QHR, QHS, QKN, QKQ, QKS, QKT, QNN, QNQ, QNR, QNS, QNT, QQQ, QQR, QQS, QQT, QRS, QRT, QSS, QST, QTT (35) |
| 171 | HKK, HKR, HRR, KCM, QDW, QEW, QFK, QFR, QHH, QHY, QIK, QIR, QKL, QKM, QKV, QKW, QKY, QLR, QMQ, QMR, QQW, QQY, QRV, QRW, QRY (25) |
| 172 | QKP, QPR (2) |
| 173 | DRR, QAA, QAD, QAE, QAF, QAG, QAH, QAK, QAM, QAN, QAP, QAQ, QAS, QDD, QDE, QDK, QDL, QDM, QDN, QEE, QEF, QEG, QEH, QEI, QEK, QEL, QEM, QEN, QEP, QEQ, QER, QES, QET, QEY, QGM, QHP, QPQ (37) |
| 174 | QAC, QAR, QAW, QAY, QCD, QCE, QCI, QCK, QCL, QCN, QCQ, QCR, QCS, QCT, QCV, QCY, QDF, QDI, QDV, QDY, QEV, QFH, QFN, QFQ, QFS, QFT, QHI, QHL, QHM, QHT, QHV, QIN, QIQ, QLN, QLQ, QMN, QMP, QMS, QMT, QMY, QNV, QNW, QNY, QQV, QSW, QSY, QTW, QTY, QVY, QYY (50) |
| 175 | QAI, QAL, QAT, QAV, QII, QIS, QIT, QIV, QLS, QLT, QLV, QSV, QTV, QVV (14) |
| 176 | QFF, QFI, QFL, QFM, QFV, QFY, QIL, QIM, QIW, QIY, QLL, QLM, QLW, QLY, QMV, QVW, QWY (17) |
| 177 | KII, KIL, KIV, KLV, KVV (5) |
| 178 | KAC, KAF, KAH, KAK, KAM, KAQ, KAR, KAW, KAY, KCD, KCE, KCF, KCK, KCL, KCN, KCP, KCQ, KCW, KCY, KDF, KDH, KDI, KDL, KDM, KDV, KDW, KDY, KEF, KEI, KEL, KEM, KET, KEV, KEW, KEY, KFH, KFK, KFN, KFQ, KFR, KFS, KFT, KGM, KHH, KHI, KHL, KHM, KHN, KHP, KHQ, KHS, KHT, KHV, KHW, KHY, KIN, KIQ, KKM, KLN, KLQ, KLT, KLY, KMM, KMN, KMP, KMQ, KMR, KMS, KMT, KMV, KMY, KNV, KNW, KNY, KQV, KQW, KQY, KSW, KSY, KTW, KTY, KVY, KYY, QKK (84) |
| 179 | KAD, KAE, KAG, KAN, KDD, KDE, KDG, KEE, KEG, KEH, KEK, KEN, KEQ, KES (14) |
| 180 | KAI, KAL, KAV (3) |
| 181 | KDK, KDN, KDQ, KDR, KDS, KDT, KER, KGG, KGH, KGK, KGN, KGQ, KGR, KGS, KGT, KHK, KHR, KKK, KKN, KKQ, KKR, KKS, KKT, KNN, KNQ, KNR, KNS, KNT, KQQ, KQR, KQS, KQT, KRR, KRS, KRT, KSS, KST (37) |
| 182 | KCI, KCS, KCT, KCV, KIS, KIT, KSV, KTT, KTV (9) |
| 183 | KDP, KEP, KGP, KKP, KNP, KPP, KPQ, KPR, KPS (9) |
| 184 | KKW, KKY, KRW, KRY (4) |
| 185 | KFF, KFI, KFL, KFM, KFV, KFW, KFY, KIM, KIW, KIY, KLL, KLM, KLW, KMW, KVW, KWW, KWY (17) |
| 186 | KAA, KAP, KAS, KAT, KFG, KFP, KGI, KGL, KGV, KGW, KGY, KIP, KLP, KLS, KPT, KPV, KPW, KPY (18) |
| 187 | KIK, KIR, KKL, KKV, KLR, KRV (6) |
| 188 | FDP, FEP, FGP, FKP, FNP, FPP, FPQ, FPR, FPS, FPT (10) |
| 189 | FFR, FKW, FKY, FRW, FRY (5) |
| 190 | FDW, FEW, FEY, FHW, FQW, WAA, WAV (7) |

FIG. 4 I

| Index | Members in cluster (total number) |
|---|---|
| 191 | FAD, FAE, FAG, FAK, FAN, FAP, FAQ, FAS, FDD, FDE, FDG, FDK, FEE, FEG, FEH, FEK, FEN, FEQ, FER, FES, FET, FGK, FNN (23) |
| 192 | FAI, FAL, FAV, FFV, FII, FIL, FIT, FIV, FLL, FLT, FLV (11) |
| 193 | FAA, FFG, FFP, FFS, FGI, FGL, FGV, FGW, FIP, FLP, FLS, FMP, FPV, FPW, FPY, FSV (16) |
| 194 | FCP, FDY, FGY, FHP, FHY, FNW, FNY, FQY, FSW, FSY, FTY (11) |
| 195 | FAC, FAH, FAR, FAT, FAY, FCE, FDF, FDI, FDL, FDM, FDV, FEF, FEI, FEL, FEM, FEV, FFK, FFN, FFQ, FGM, FHM, FIK, FIN, FIQ, FKL, FKM, FKV, FLN, FLQ, FLR, FMQ, FMS, FMT, FQV (34) |
| 196 | FAF, FAM, FAW, FCF, FCL, FCW, FCY, FFF, FFH, FFI, FFL, FFM, FFT, FFW, FFY, FHI, FHL, FHV, FIM, FIW, FIY, FLM, FLW, FLY, FMM, FMV, FMW, FMY, FTW, FVW, FVY, FWY, FYY, WVV (34) |
| 197 | ECC, ECD, ECG, ECH, ECN, ECQ, ECR, ECS, ECT, EHH (10) |
| 198 | ECK, EDH, EDQ, EDR, EDS, EDT, EGG, EGH, EGN, EGQ, EGR, EGS, EGT, EHK, EHN, EHQ, EHR, EHS, EHT, EKN, EKQ, EKS, EKT, EMR, ENQ, ENS, ENT, EQQ, EQR, EQS, EQT, ERS, ERT, ESS, EST, ETT (36) |
| 199 | EKK, EKR, ERR (3) |

FIG. 4J

| | $\alpha_{1A}$ | $\alpha_{1B}$ | $\alpha_{1D}$ | $\alpha_{2A}$ | $\alpha_{2B}$ | $\alpha_{2C}$ | $\beta_1$ | $\beta_2$ | $\beta_3$ |
|---|---|---|---|---|---|---|---|---|---|
| $\alpha_{1A}$ (466 aa) | 100 | | | | | | | | |
| $\alpha_{1B}$ (519 aa) | 47.2 | 100 | | | | | | | |
| $\alpha_{1D}$ (572 aa) | 45.5 | 46.2 | 100 | | | | | | |
| $\alpha_{2A}$ (450 aa) | 24.2 | 20.7 | 24.9 | 100 | | | | | |
| $\alpha_{2B}$ (450 aa) | 22.9 | 22.7 | 24.9 | 46.7 | 100 | | | | |
| $\alpha_{2C}$ (462 aa) | 22.1 | 22.5 | 26.8 | 49.1 | 48.2 | 100 | | | |
| $\beta_1$ (477 aa) | 21.0 | 22.4 | 28.5 | 25.8 | 23.6 | 24.0 | 100 | | |
| $\beta_2$ (413 aa) | 25.7 | 26.6 | 25.9 | 22.5 | 19.1 | 18.6 | 48.4 | 100 | |
| $\beta_3$ (408 aa) | 28.2 | 29.7 | 28.2 | 25.5 | 20.6 | 23.5 | 47.8 | 39.2 | 100 |

|  | AR α generic | AR α selective | AR β generic | AR β selective | AR α & AR β | Σ |
|---|---|---|---|---|---|---|
| antagonist | 4 | 4 | 11 | 6 | 1 | 26 |
| agonist | 1 | 6 | 1 | 9 | 5 | 22 |
| Σ | 15 | | 27 | | 6 | 48 |

(B)

| (A) adrenergic receptor antagonist | |
|---|---|
| drug | target |
| ergotamine | $\alpha_1, \alpha_2$ |
| metazocine | $\alpha_1$ |
| dibenzyline | $\alpha_1, \alpha_2$ |
| regitine | $\alpha_1, \alpha_2$ |
| prazosin | $\alpha_1$ |
| terazosin | $\alpha_1$ |
| tolazoline | $\alpha_1, \alpha_2$ |
| yohimbine | $\alpha_2$ |
| acebutolol | $\beta_1$ |
| alprenolol | $\beta_1, \beta_2$ |
| atenolol | $\beta_1$ |
| betaxolol | $\beta_1$ |
| bisoprolol | $\beta_1$ |
| bupranolol | $\beta_1$ |
| carteolol | $\beta_1, \beta_2$ |
| levobunolol | $\beta_1, \beta_2$ |
| metoprolol | $\beta_1, \beta_2$ |
| nadolol | $\beta_1, \beta_2$ |
| oxprenolol | $\beta_1, \beta_2$ |
| pindolol | $\beta_1, \beta_2$ |
| practolol | $\beta_1$ |
| propranolol | $\beta_1, \beta_2$ |
| sotalol | $\beta_1, \beta_2$ |
| timolol | $\beta_1, \beta_2$ |
| toliprolol | $\beta_1, \beta_2$ |
| labetalol | $\alpha_2, \beta_1, \beta_2$ |

| (B) adrenergic receptor agonist | |
|---|---|
| drug | target |
| clonidine | $\alpha_2$ |
| guanabenz | $\alpha_2$ |
| metaraminol | $\alpha_1, \alpha_2$ |
| methoxamine | $\alpha_1$ |
| oxymetazoline | $\alpha_2$ |
| phenylephrine | $\alpha_1$ |
| tizanidine | $\alpha_2$ |
| albuterol | $\beta_2$ |
| bitolterol | $\beta_2$ |
| clenbuterol | $\beta_2$ |
| clorprenaline | $\beta_2$ |
| dobutamine | $\beta_1$ |
| isoetharine | $\beta_2$ |
| isoprenaline | $\beta_1, \beta_2$ |
| metaproterenol | $\beta_2$ |
| ritodrine | $\beta_2$ |
| terbutaline | $\beta_2$ |
| dopamine | $\alpha_1, \alpha_2, \beta_1, \beta_2$ |
| ephedrine | $\alpha_1, \alpha_2, \beta_1, \beta_2$ |
| epinephrine | $\alpha_1, \alpha_2, \beta_1, \beta_2$ |
| levarterenol | $\alpha_1, \alpha_2, \beta_1$ |
| mephentermine | $\alpha_1, \alpha_2, \beta_1$ |

FIG. 6

| kernel | TP | FN | TN | FP | prec.(%) | sens.(%) | acc.(%) | hyperparameters |
|---|---|---|---|---|---|---|---|---|
| linear | 73 | 69 | 263 | 27 | 73.00 | 51.41 | 77.78 | $C = 16$ |
| polynomial | 112 | 30 | 274 | 16 | 87.50 | 78.87 | 89.35 | $C = 16, \gamma = 2^{-9.125}, d = 5, r = 1$ |
| RBF | 113 | 29 | 275 | 15 | 88.28 | 79.58 | 89.81 | $C = 16, \gamma = 2^{-7.25}$ |
| sigmoid | 111 | 31 | 262 | 28 | 81.16 | 78.87 | 87.04 | $C = 16, \gamma = 2^{-8.25}, r = -3$ |

FIG. 7

| protein | TP | FN | TN | FP | prec.(%) | sens.(%) | acc.(%) | hyperparameters |
|---|---|---|---|---|---|---|---|---|
| $(Co_d)$ | 107 | 35 | 272 | 18 | 85.60 | 75.35 | 87.73 | $C = 16, \gamma = 2^{-8.25}$ |
| $(Co_t)$ | 112 | 30 | 261 | 29 | 79.43 | 78.87 | 86.34 | $C = 16, \gamma = 2^{-10.875}$ |
| $(Cl_d)$ | 105 | 37 | 258 | 32 | 76.64 | 73.94 | 84.03 | $C = 24, \gamma = 2^{-8.875}$ |
| $(Cl_t)$ | 113 | 29 | 275 | 15 | 88.28 | 79.58 | 89.81 | $C = 16, \gamma = 2^{-7.25}$ |

Here, chemicals are encoded by $(F, G_{15}^{12})$, and binding is expressed by concatenation.

FIG. 8

| MS | TP | FN | TN | FP | prec.(%) | sens.(%) | acc.(%) | hyperparameters |
|---|---|---|---|---|---|---|---|---|
| $(F, G_{15}^{12})$ | 113 | 29 | 275 | 15 | 88.28 | 79.58 | 89.81 | $C = 16, \gamma = 2^{-7.25}$ |
| $(F)$ | 119 | 23 | 257 | 33 | 78.29 | 83.80 | 87.04 | $C = 16, \gamma = 2^{-9.125}$ |
| $(G_{15}^{12})$ | 100 | 42 | 267 | 23 | 81.30 | 70.42 | 84.95 | $C = 32, \gamma = 2^{-8}$ |
| $(F', G_{15}^{12'})$ | 105 | 37 | 267 | 23 | 82.03 | 73.94 | 86.11 | $C = 16, \gamma = 2^{-9.875}$ |
| $(F', G_{15}^{12})$ | 102 | 40 | 269 | 21 | 82.93 | 71.83 | 85.88 | $C = 16, \gamma = 2^{-8.125}$ |
| $(F, G_{15}^{12'})$ | 109 | 33 | 268 | 22 | 83.21 | 76.76 | 87.27 | $C = 16, \gamma = 2^{-9.125}$ |
| $(F')$ | 105 | 37 | 266 | 24 | 81.40 | 73.94 | 85.88 | $C = 16, \gamma = 2^{-8.25}$ |
| $(G_{15}^{12'})$ | 101 | 41 | 266 | 24 | 80.80 | 71.13 | 84.95 | $C = 32, \gamma = 2^{-9.625}$ |

Here, proteins are encoded by $(Cl_t)$ and binding is expressed by concatenation.

FIG. 9

| type | vector | TP | FN | TN | FP | prec.(%) | sens.(%) | acc.(%) | parameters |
|---|---|---|---|---|---|---|---|---|---|
| conc. | $(F, G_{15}^{12}, Cl_t)$ | 113 | 29 | 275 | 15 | 88.28 | 79.58 | 89.81 | $C = 16, \gamma = 2^{-7.25}$ |
| (RBF) | $(D_4^{10}, Cl_t)$ | 120 | 22 | 274 | 16 | 88.24 | 84.51 | 91.20 | $C = 128, \gamma = 2^{-11}$ |
|  | $(F, G_{15}^{12}, D_4^6, Cl_t)$ | 120 | 22 | 274 | 16 | 88.24 | 84.51 | 91.20 | $C = 16, \gamma = 2^{-9}$ |
| combi. | $(F, G_{15}^{12}, Cl_t)$ | 122 | 20 | 276 | 14 | 89.71 | 85.92 | 92.13 | Table D.7 |
|  | $(F, Cl_t)$ | 119 | 23 | 274 | 16 | 88.15 | 83.80 | 90.97 | Table D.7 |
|  | $(G_{7.5}^{12}, Cl_t)$ | 109 | 33 | 268 | 22 | 83.21 | 76.76 | 87.27 | Table D.7 |
|  | $(D_0^8, Cl_t)$ | 132 | 10 | 276 | 14 | 90.41 | 92.96 | 94.44 | Table D.7 |
|  | $(F, G_{7.5}^{12}, D_2^8, Cl_t)$ | 130 | 12 | 281 | 9 | 93.53 | 91.55 | 95.14 | Table D.7 |
|  | $(F, D_0^8, Cl_t)$ | 131 | 11 | 278 | 12 | 91.61 | 92.25 | 94.68 | Table D.7 |
|  | $(G_{15}^{12}, D_0^8, Cl_t)$ | 132 | 10 | 276 | 14 | 90.41 | 92.96 | 94.44 | Table D.7 |

FIG. 10

(A) Classification of antagonist-receptor pairs and agonist-receptor pairs

| type | vector | TP | FN | TN | FP | prec.(%) | sens.(%) | acc.(%) | parameters |
|---|---|---|---|---|---|---|---|---|---|
| conc. | $(F, G^{12}_{25}, Cl_t)$ | 69 | 0 | 71 | 2 | 97.18 | 100 | 98.59 | $C = 8, \gamma = 2^{-9}$ |
| (RBF) | $(F, Cl_t)$ | 68 | 1 | 71 | 2 | 97.14 | 98.55 | 97.89 | $C = 8, \gamma = 2^{-7.75}$ |
|  | $(G^{12}_{7.5}, Cl_t)$ | 69 | 0 | 71 | 2 | 97.18 | 100 | 98.59 | $C = 16, \gamma = 2^{8.625}$ |
|  | $(D^{10}_{4}, Cl_t)$ | 69 | 0 | 73 | 0 | 100 | 100 | 100 | $C = 128, \gamma = 2^{-15}$ |
| combi. | $(F, G^{12}_{7.5}, Cl_t)$ | 69 | 0 | 72 | 1 | 98.57 | 100 | 99.30 | Table D.8 |

(B) Classification of antagonsits and agonists

| type | vector | TP | FN | TN | FP | prec.(%) | sens.(%) | acc.(%) | parameters |
|---|---|---|---|---|---|---|---|---|---|
| conc. | $(F, G^{12}_{25})$ | 22 | 4 | 19 | 3 | 88.00 | 84.62 | 85.42 | $C = 4, \gamma = 2^{-8.375}$ |
| (RBF) | $(F)$ | 23 | 3 | 19 | 3 | 88.46 | 88.46 | 87.50 | $C = 16, \gamma = 2^{-8.25}$ |
|  | $G^{12}_{15}$ | 22 | 4 | 17 | 5 | 81.48 | 84.62 | 81.25 | $C = 32, \gamma = 2^{-8.625}$ |
|  | $(D^{10}_{4})$ | 22 | 4 | 22 | 0 | 100 | 84.62 | 91.67 | $C = 128, \gamma = 2^{-14.5}$ |
| combi. | $(F, G^{12}_{15})$ | 24 | 2 | 19 | 3 | 88.89 | 92.31 | 89.58 | Table D.8 |

FIG. 11

| type | # of drugs | # of proteins | # of protein-drug pairs |
|---|---|---|---|
| all | 519 | 291 | 980 |
| receptor related | 275 | 85 | 495 |

FIG. 12A

| Index | Drug names (NIST ID) | UniProt ID of target proteins | Is receptor? |
|---|---|---|---|
| 1 | Acebutolol (120460) | P08588 | Y |
| 2 | Acetaminophen (229798) | P23319 | |
| 3 | Acetaminophen (229798) | P35354 | |
| 4 | Acetazolamide (239163) | P00915 | |
| 5 | Acetohexamide (247668) | P48048 | |
| 6 | Acetohydroxamic Acid (231100) | P18314 | |
| 7 | Acetophenazine (247953) | P14416 | Y |
| 8 | Acetophenazine (247953) | P21728 | Y |
| 9 | Acitretin (141590) | P10276 | Y |
| 10 | Acitretin (141590) | P10826 | Y |
| 11 | Acitretin (141590) | P13631 | Y |
| 12 | Acitretin (141590) | P19793 | Y |
| 13 | Acitretin (141590) | P22932 | Y |
| 14 | Acitretin (141590) | P28702 | Y |
| 15 | Acitretin (141590) | P48443 | Y |
| 16 | Acyclovir (248607) | P04293 | |
| 17 | Acyclovir (248607) | P09252 | |
| 18 | Adenosine (227956) | Q08828 | |
| 19 | Albendazole (256773) | P50719 | |
| 20 | Albuterol (298757) | P07550 | Y |
| 21 | Alclometasone (235695) | P04083 | |
| 22 | Alclometasone (235695) | P08185 | Y |
| 23 | Alfentanil (248171) | P35372 | Y |
| 24 | Allopurinol (230398) | P47989 | |
| 25 | Alprazolam (250574) | P14867 | Y |
| 26 | Alprazolam (250574) | P30536 | Y |
| 27 | Alprazolam (250574) | P31644 | Y |
| 28 | Alprazolam (250574) | P34903 | Y |
| 29 | Alprazolam (250574) | P47869 | Y |
| 30 | Alprazolam (250574) | P48169 | Y |
| 31 | Alprazolam (250574) | Q16445 | Y |
| 32 | Alprenolol (42318) | P07550 | Y |
| 33 | Alprenolol (42318) | P08588 | Y |
| 34 | Amantadine (232354) | P10920 | |
| 35 | Amantadine (232354) | P14416 | Y |
| 36 | Amantadine (232354) | P21728 | Y |
| 37 | Amcinonide (248609) | P04083 | |
| 38 | Amcinonide (248609) | P04150 | Y |
| 39 | Amiloride (254340) | P19634 | |
| 40 | Amiloride (254340) | P19801 | |
| 41 | Amiloride (254340) | P37088 | |

FIG. 12B

| Index | Drug names (NIST ID) | UniProt ID | receptor |
|---|---|---|---|
| 42 | Amiloride (254340) | P51168 | |
| 43 | Amiloride (254340) | P51170 | |
| 44 | Amiloride (254340) | P51172 | |
| 45 | Amiloride (254340) | P78348 | |
| 46 | Amiloride (254340) | Q16515 | |
| 47 | Aminocaproic Acid (298481) | P00747 | |
| 48 | Aminoglutethimide (247719) | P11511 | |
| 49 | Aminophylline (257605) | P33765 | Y |
| 50 | Aminophylline (257605) | Q14432 | |
| 51 | Aminosalicylic Acid (228370) | P64143 | |
| 52 | Amiodarone (120482) | P08588 | Y |
| 53 | Amiodarone (120482) | P35348 | Y |
| 54 | Amitriptyline (42327) | P23975 | |
| 55 | Amitriptyline (42327) | P31645 | |
| 56 | Amlodipine (247418) | P00915 | |
| 57 | Amlodipine (247418) | Q06432 | |
| 58 | Amodiaquine (298615) | P69905 | |
| 59 | Amoxapine (247984) | P23975 | |
| 60 | Amoxapine (247984) | P31645 | |
| 61 | Amphetamine (235438) | P08913 | Y |
| 62 | Amphetamine (235438) | P35348 | Y |
| 63 | Amsacrine (131642) | P11388 | |
| 64 | Anisindione (120491) | P38435 | |
| 65 | Apomorphine (248048) | P14416 | Y |
| 66 | Apomorphine (248048) | P21728 | Y |
| 67 | Apomorphine (248048) | P21917 | Y |
| 68 | Aspirin (221215) | P23319 | |
| 69 | Aspirin (221215) | P35354 | |
| 70 | Astemizole (292149) | P35367 | Y |
| 71 | Atenolol (107108) | P08588 | Y |
| 72 | Atovaquone (247458) | P43264 | |
| 73 | Atropine (221030) | P08172 | Y |
| 74 | Atropine (221030) | P08173 | Y |
| 75 | Atropine (221030) | P08912 | Y |
| 76 | Atropine (221030) | P11229 | Y |
| 77 | Atropine (221030) | P20309 | Y |
| 78 | Azatadine (248317) | P35367 | Y |
| 79 | Azelaic Acid (113078) | P00440 | |
| 80 | Azelaic Acid (113078) | P00582 | |
| 81 | Azelaic Acid (113078) | P31213 | |
| 82 | Azelaic Acid (113078) | P66011 | |
| 83 | Baclofen (290937) | Q9UBS5 | Y |
| 84 | Beclomethasone (247723) | P04083 | |
| 85 | Beclomethasone (247723) | P08185 | Y |
| 86 | Bendroflumethiazide (247724) | P00915 | |
| 87 | Bendroflumethiazide (247724) | P00918 | |

FIG. 12C

| Index | Drug names (NIST ID) | UniProt ID | receptor |
|---|---|---|---|
| 88 | Bendroflumethiazide (247724) | P22748 | |
| 89 | Bendroflumethiazide (247724) | P55017 | |
| 90 | Bendroflumethiazide (247724) | Q12791 | |
| 91 | Bentiromide (248616) | P04746 | |
| 92 | Bentiromide (248616) | P16233 | |
| 93 | Benzocaine (250591) | Q9Y5Y9 | |
| 94 | Benzonatate (247726) | Q14524 | |
| 95 | Benzphetamine (250592) | P08913 | Y |
| 96 | Benzphetamine (250592) | P35348 | Y |
| 97 | Benzquinamide (247108) | P08172 | Y |
| 98 | Benzquinamide (247108) | P08173 | Y |
| 99 | Benzquinamide (247108) | P08912 | Y |
| 100 | Benzquinamide (247108) | P11229 | Y |
| 101 | Benzquinamide (247108) | P20309 | Y |
| 102 | Benzquinamide (247108) | P35367 | Y |
| 103 | Benzthiazide (247728) | P00915 | |
| 104 | Benzthiazide (247728) | P00918 | |
| 105 | Benzthiazide (247728) | P22748 | |
| 106 | Benzthiazide (247728) | P55017 | |
| 107 | Benzthiazide (247728) | Q12791 | |
| 108 | Benztropine (246818) | P11229 | Y |
| 109 | Betamethasone (74535) | P04083 | |
| 110 | Betamethasone (74535) | P04150 | Y |
| 111 | Betaxolol (121082) | P08588 | Y |
| 112 | Betazole (298618) | P25021 | Y |
| 113 | Biperiden (247729) | P11229 | Y |
| 114 | Biperiden (247729) | Q15822 | Y |
| 115 | Bisoprolol (159236) | P07550 | Y |
| 116 | Bisoprolol (159236) | P08588 | Y |
| 117 | Bitolterol Mesylate (248773) | P07550 | Y |
| 118 | Bromocriptine (248047) | P14416 | Y |
| 119 | Bromodiphenhydramine (247732) | P35367 | Y |
| 120 | Brompheniramine (250546) | P35367 | Y |
| 121 | Buclizine (248626) | P11229 | Y |
| 122 | Buclizine (248626) | P35367 | Y |
| 123 | Budesonide (248257) | P04150 | Y |
| 124 | Bumetanide (248772) | P05023 | |
| 125 | Bumetanide (248772) | Q13621 | |
| 126 | Bupivacaine (159229) | P34995 | Y |
| 127 | Bupivacaine (159229) | Q9Y5Y9 | |
| 128 | Buprenorphine (248591) | P35372 | Y |
| 129 | Buprenorphine (248591) | P41145 | Y |
| 130 | Bupropion (248891) | P23975 | |
| 131 | Bupropion (248891) | Q01959 | |
| 132 | Buspirone (248867) | P08908 | Y |

FIG. 12D

| Index | Drug names (NIST ID) | UniProt ID | receptor |
|---|---|---|---|
| 133 | Buspirone (248867) | P14416 | Y |
| 134 | Butabarbital (250699) | P14867 | Y |
| 135 | Butalbital (10652) | P14867 | Y |
| 136 | Butoconazole (248868) | P50859 | |
| 137 | Butorphanol Tartrate (247735) | P35372 | Y |
| 138 | Butorphanol Tartrate (247735) | P41145 | Y |
| 139 | Caffeine (290714) | P30542 | Y |
| 140 | Caffeine (290714) | Q07343 | |
| 141 | Calcitriol (248752) | O15528 | |
| 142 | Calcitriol (248752) | P11473 | Y |
| 143 | Captopril (250717) | P22966 | |
| 144 | Carbachol (230651) | P08172 | Y |
| 145 | Carbachol (230651) | P11229 | Y |
| 146 | Carbachol (230651) | Q15822 | Y |
| 147 | Carbamazepine (236284) | Q14524 | |
| 148 | Carbidopa (298626) | P20711 | |
| 149 | Carbimazole (107111) | P07202 | |
| 150 | Carbinoxamine (58729) | P11229 | Y |
| 151 | Carbinoxamine (58729) | P35367 | Y |
| 152 | Carmustine (248168) | P00390 | |
| 153 | Carteolol (159278) | P07550 | Y |
| 154 | Carteolol (159278) | P08588 | Y |
| 155 | Cefaclor (235663) | Q8XJ01 | |
| 156 | Cephalexin (235673) | Q8XJ01 | |
| 157 | Chloramphenicol (52747) | P0A7J3 | |
| 158 | Chlordiazepoxide (23260) | P14867 | Y |
| 159 | Chlormezanone (233880) | P30536 | Y |
| 160 | Chloroprocaine (137198) | P46098 | Y |
| 161 | Chloroprocaine (137198) | Q01959 | |
| 162 | Chloroprocaine (137198) | Q8TCU5 | Y |
| 163 | Chloroprocaine (137198) | Q9GZZ6 | Y |
| 164 | Chloroprocaine (137198) | Q9Y5Y9 | |
| 165 | Chloroquine (42361) | P69905 | |
| 166 | Chlorothiazide (244641) | P00915 | |
| 167 | Chlorothiazide (244641) | P00918 | |
| 168 | Chlorothiazide (244641) | P22748 | |
| 169 | Chlorothiazide (244641) | P55017 | |
| 170 | Chlorothiazide (244641) | Q12791 | |
| 171 | Chlorotrianisene (248055) | P03372 | Y |
| 172 | Chlorpheniramine (250548) | P35367 | Y |
| 173 | Chlorpromazine (250594) | P14416 | Y |
| 174 | Chlorpromazine (250594) | P28223 | Y |
| 175 | Chlorpropamide (233879) | P48048 | |
| 176 | Chlorprothixene (247780) | P14416 | Y |
| 177 | Chlorprothixene (247780) | P21728 | Y |
| 178 | Chlorthalidone (246980) | Q13621 | |

FIG. 12 E

| Index | Drug names (NIST ID) | UniProt ID | receptor |
|---|---|---|---|
| 179 | Chlorzoxazone (239377) | Q12791 | |
| 180 | Cholecalciferol (248815) | P11473 | Y |
| 181 | Cholecalciferol (248815) | Q02318 | |
| 182 | Cholecalciferol (248815) | Q6VVX0 | |
| 183 | Ciclopirox (248393) | P16050 | |
| 184 | Ciclopirox (248393) | P23319 | |
| 185 | Ciclopirox (248393) | P35354 | |
| 186 | Cimetidine (237089) | P25021 | Y |
| 187 | Cinnarizine (158442) | O00555 | |
| 188 | Cinnarizine (158442) | P14416 | Y |
| 189 | Cinnarizine (158442) | P35367 | Y |
| 190 | Ciprofloxacin (121210) | P11388 | |
| 191 | Cisapride (121231) | Q13639 | Y |
| 192 | Clemastine (247788) | P35367 | Y |
| 193 | Clindamycin (247789) | P0A7J3 | |
| 194 | Clobazam (107121) | P14867 | Y |
| 195 | Clocortolone (248665) | P04083 | |
| 196 | Clofazimine (298622) | Q5L2G3 | |
| 197 | Clofibrate (245138) | P06858 | |
| 198 | Clomifene (248400) | P03372 | Y |
| 199 | Clomipramine (246870) | P09211 | |
| 200 | Clomipramine (246870) | P23975 | |
| 201 | Clomipramine (246870) | P31645 | |
| 202 | Clonazepam (250715) | P14867 | Y |
| 203 | Clonidine (233859) | P08913 | Y |
| 204 | Clotrimazole (191548) | P10614 | |
| 205 | Clozapine (247212) | P14416 | Y |
| 206 | Clozapine (247212) | P21917 | Y |
| 207 | Clozapine (247212) | P28223 | Y |
| 208 | Clozapine (247212) | P35367 | Y |
| 209 | Clozapine (247212) | Q9H3N8 | Y |
| 210 | Clozapine (247212) | Q9NYX4 | Y |
| 211 | Cocaine (113834) | P21728 | Y |
| 212 | Cocaine (113834) | P23975 | |
| 213 | Cocaine (113834) | P30531 | |
| 214 | Cocaine (113834) | P31645 | |
| 215 | Cocaine (113834) | P35462 | Y |
| 216 | Cocaine (113834) | P41145 | Y |
| 217 | Cocaine (113834) | Q01959 | |
| 218 | Cocaine (113834) | Q14524 | |
| 219 | Cocaine (113834) | Q9UI33 | |
| 220 | Cocaine (113834) | Q9Y5Y9 | |
| 221 | Codeine (313075) | P35372 | Y |
| 222 | Codeine (313075) | P41143 | Y |
| 223 | Codeine (313075) | P41145 | Y |
| 224 | Cyclizine (250597) | P08172 | Y |

FIG. 12F

| Index | Drug names (NIST ID) | UniProt ID | receptor |
|---|---|---|---|
| 225 | Cyclizine (250597) | P11229 | Y |
| 226 | Cyclizine (250597) | P20309 | Y |
| 227 | Cyclizine (250597) | P35367 | Y |
| 228 | Cyclobenzaprine (246605) | P28223 | Y |
| 229 | Cyclopentolate (292189) | P11229 | Y |
| 230 | Cycloserine (237050) | P0A6BA | |
| 231 | Cycloserine (237050) | P0A6JB | |
| 232 | Cyclothiazide (298640) | P00915 | |
| 233 | Cyclothiazide (298640) | P00918 | |
| 234 | Cyclothiazide (298640) | P22748 | |
| 235 | Cyclothiazide (298640) | P54710 | |
| 236 | Cyclothiazide (298640) | Q12791 | |
| 237 | Cycrimine (248053) | P11229 | Y |
| 238 | Cyproheptadine (250706) | P28223 | Y |
| 239 | Cytarabine (254325) | P06746 | |
| 240 | Dantrolene (247798) | P21827 | Y |
| 241 | Dapsone (51808) | P29251 | |
| 242 | Demeclocycline (17858) | P0A7V8 | |
| 243 | Demeclocycline (17858) | P0A7X3 | |
| 244 | Deserpidine (247162) | P12821 | |
| 245 | Desflurane (308772) | P03886 | |
| 246 | Desflurane (308772) | P14867 | Y |
| 247 | Desflurane (308772) | P23415 | Y |
| 248 | Desflurane (308772) | P30049 | |
| 249 | Desflurane (308772) | P42261 | Y |
| 250 | Desflurane (308772) | P98194 | |
| 251 | Desflurane (308772) | Q09470 | |
| 252 | Desipramine (250707) | P07550 | Y |
| 253 | Desipramine (250707) | P08172 | Y |
| 254 | Desipramine (250707) | P08588 | Y |
| 255 | Desipramine (250707) | P11229 | Y |
| 256 | Desipramine (250707) | P23975 | |
| 257 | Desipramine (250707) | P31645 | |
| 258 | Desipramine (250707) | P35367 | Y |
| 259 | Desoximetasone (121216) | P04083 | |
| 260 | Dexamethasone (235905) | P04083 | |
| 261 | Dexamethasone (235905) | P04150 | Y |
| 262 | Dexbrompheniramine (15054) | P35367 | Y |
| 263 | Dexrazoxane (131624) | P11388 | |
| 264 | Dextromethorphan (235679) | P31645 | |
| 265 | Dextromethorphan (235679) | Q15822 | Y |
| 266 | Dextromethorphan (235679) | Q5T1J1 | Y |
| 267 | Dextromethorphan (235679) | Q8TCU5 | Y |
| 268 | Dextromethorphan (235679) | Q99720 | Y |
| 269 | Diazepam (113837) | P14867 | Y |
| 270 | Diazepam (113837) | P30536 | Y |

FIG. 12G

| Index | Drug names (NIST ID) | UniProt ID | receptor |
|---|---|---|---|
| 271 | Diazoxide (292038) | P00915 | |
| 272 | Diazoxide (292038) | P00918 | |
| 273 | Diazoxide (292038) | P22748 | |
| 274 | Diazoxide (292038) | P55017 | |
| 275 | Diazoxide (292038) | Q12791 | |
| 276 | Dichlorphenamide (247909) | P00915 | |
| 277 | Diclofenac (158432) | P23319 | |
| 278 | Diclofenac (158432) | P35354 | |
| 279 | Dicloxacillin (247910) | Q8XJ01 | |
| 280 | Dicumarol (246974) | Q9BQB6 | |
| 281 | Dicyclomine (250600) | P11229 | Y |
| 282 | Didanosine (122987) | P03369 | |
| 283 | Dienestrol (248819) | P03372 | Y |
| 284 | Diethylcarbamazine (135586) | P00395 | |
| 285 | Diethylcarbamazine (135586) | P16050 | |
| 286 | Diethylpropion (246177) | P23975 | |
| 287 | Diethylpropion (246177) | Q01959 | |
| 288 | Diethylstilbestrol (234131) | P03372 | Y |
| 289 | Diflorasone (248673) | P04083 | |
| 290 | Diflunisal (248674) | P23319 | |
| 291 | Diflunisal (248674) | P35354 | |
| 292 | Digoxin (120638) | P05023 | |
| 293 | Dihydroergotamine (248068) | P28221 | Y |
| 294 | Dihydroergotamine (248068) | P28222 | Y |
| 295 | Dihydrotachysterol (33089) | P11473 | Y |
| 296 | Diltiazem (247122) | Q06432 | |
| 297 | Diphenhydramine (250549) | P35367 | Y |
| 298 | Diphenidol (247917) | P08172 | Y |
| 299 | Diphenidol (247917) | P11229 | Y |
| 300 | Diphenidol (247917) | P20309 | Y |
| 301 | Diphenoxylate (125715) | P35372 | Y |
| 302 | Diphenylpyraline (250708) | P35367 | Y |
| 303 | Dipyridamole (237441) | Q9Y233 | |
| 304 | Disopyramide (159197) | Q14524 | |
| 305 | Disulfiram (228650) | P05091 | |
| 306 | Disulfiram (228650) | P30536 | Y |
| 307 | Dobutamine (235669) | P08588 | Y |
| 308 | Dopamine (228609) | P08588 | Y |
| 309 | Dopamine (228609) | P09172 | |
| 310 | Dopamine (228609) | P21728 | Y |
| 311 | Doxepin (292030) | P23975 | |
| 312 | Doxepin (292030) | P31645 | |
| 313 | Doxepin (292030) | P35367 | Y |
| 314 | Doxorubicin (131605) | P11388 | |
| 315 | Doxylamine (250552) | P11229 | Y |
| 316 | Doxylamine (250552) | P35367 | Y |

FIG. 12 H

| Index | Drug names (NIST ID) | UniProt ID | receptor |
|---|---|---|---|
| 317 | Dromostanolone (313018) | P03372 | Y |
| 318 | Dromostanolone (313018) | P04278 | |
| 319 | Dromostanolone (313018) | P10275 | Y |
| 320 | Dromostanolone (313018) | P16471 | Y |
| 321 | Droperidol (247071) | P14416 | Y |
| 322 | Dyclonine (65070) | Q9Y5Y9 | |
| 323 | Dyphylline (239172) | Q07343 | |
| 324 | Econazole (193280) | P10614 | |
| 325 | Encainide (121124) | Q14524 | |
| 326 | Enflurane (187240) | P03886 | |
| 327 | Enflurane (187240) | P14867 | Y |
| 328 | Enflurane (187240) | P23415 | Y |
| 329 | Enflurane (187240) | P30049 | |
| 330 | Enflurane (187240) | P42261 | Y |
| 331 | Enflurane (187240) | P98194 | |
| 332 | Enflurane (187240) | Q09470 | |
| 333 | Epinephrine (24257) | P07550 | Y |
| 334 | Epinephrine (24257) | P08588 | Y |
| 335 | Epinephrine (24257) | P35348 | Y |
| 336 | Ergocalciferol (248164) | O15528 | |
| 337 | Ergocalciferol (248164) | P11473 | Y |
| 338 | Ergocalciferol (248164) | Q6VVX0 | |
| 339 | Ergoloid Mesylate (226969) | P08908 | Y |
| 340 | Ergotamine (248677) | P28222 | Y |
| 341 | Ergotamine (248677) | P35348 | Y |
| 342 | Estradiol (13192) | P03372 | Y |
| 343 | Estramustine (248681) | P03372 | Y |
| 344 | Estrone (42853) | P03372 | Y |
| 345 | Ethacrynic acid (159259) | Q13621 | |
| 346 | Ethanol (118507) | P14867 | Y |
| 347 | Ethanol (118507) | P23415 | Y |
| 348 | Ethanol (118507) | P23416 | Y |
| 349 | Ethanol (118507) | Q8TCU5 | Y |
| 350 | Ethinyl Estradiol (234172) | P03372 | Y |
| 351 | Ethopropazine (246857) | P11229 | Y |
| 352 | Ethopropazine (246857) | Q8TCU5 | Y |
| 353 | Ethosuximide (250694) | O43497 | |
| 354 | Ethoxzolamide (292040) | P00915 | |
| 355 | Ethynodiol Diacetate (292151) | P03372 | Y |
| 356 | Ethynodiol Diacetate (292151) | P06401 | Y |
| 357 | Etoposide (131616) | P11388 | |
| 358 | Felbamate (247587) | Q8TCU5 | Y |
| 359 | Felodipine (247476) | P54289 | Y |
| 360 | Fenfluramine (250583) | P28335 | Y |
| 361 | Fentanyl (250541) | P35372 | Y |
| 362 | Flecainide (248228) | Q14524 | |

FIG. 12 I

| Index | Drug names (NIST ID) | UniProt ID | receptor |
|---|---|---|---|
| 363 | Floxuridine (237402) | P04818 | |
| 364 | Flucytosine (238324) | P04818 | |
| 365 | Fludarabine (131665) | P09884 | |
| 366 | Fludarabine (131665) | P23921 | |
| 367 | Fludrocortisone (247932) | P08235 | Y |
| 368 | Flunisolide (120228) | P08185 | Y |
| 369 | Flunisolide (120228) | P47712 | |
| 370 | Fluocinolone Acetonide (247934) | P08185 | Y |
| 371 | Fluocinolone Acetonide (247934) | P47712 | |
| 372 | Fluocinonide (292183) | P08185 | Y |
| 373 | Fluocinonide (292183) | P47712 | |
| 374 | Fluorescein (231984) | P02768 | |
| 375 | Fluorometholone (248151) | P08185 | Y |
| 376 | Fluorometholone (248151) | P47712 | |
| 377 | Fluorouracil (230123) | P04818 | |
| 378 | Fluoxetine (250697) | P31645 | |
| 379 | Fluoxymesterone (247938) | P03372 | Y |
| 380 | Fluoxymesterone (247938) | P04278 | |
| 381 | Fluoxymesterone (247938) | P10275 | Y |
| 382 | Fluoxymesterone (247938) | P16471 | Y |
| 383 | Flupenthixol (247134) | P14416 | Y |
| 384 | Flupenthixol (247134) | P21728 | Y |
| 385 | Flupenthixol (247134) | P35348 | Y |
| 386 | Fluphenazine (120153) | P14416 | Y |
| 387 | Flurandrenolide (248069) | P08185 | Y |
| 388 | Flurandrenolide (248069) | P47712 | |
| 389 | Flurazepam (159279) | P14867 | Y |
| 390 | Flurbiprofen (248229) | P23219 | |
| 391 | Flurbiprofen (248229) | P35354 | |
| 392 | Flutamide (248839) | P10275 | Y |
| 393 | Fluvoxamine (250692) | P31645 | |
| 394 | Fomepizole (272994) | P00325 | |
| 395 | Fomepizole (272994) | P00326 | |
| 396 | Fomepizole (272994) | P07327 | |
| 397 | Furosemide (232586) | P00915 | |
| 398 | Furosemide (232586) | P00918 | |
| 399 | Furosemide (232586) | P05023 | |
| 400 | Furosemide (232586) | P22748 | |
| 401 | Furosemide (232586) | Q12791 | |
| 402 | Furosemide (232586) | Q13621 | |
| 403 | Galantamine (111316) | P22303 | |
| 404 | Gemfibrozil (248360) | P06858 | |
| 405 | Glipizide (248683) | P48048 | |
| 406 | Glyburide (247159) | P48048 | |
| 407 | Glycopyrrolate (226952) | P11229 | Y |
| 408 | Griseofulvin (238364) | P10875 | |

FIG. 12 J

| Index | Drug names (NIST ID) | UniProt ID | receptor |
|---|---|---|---|
| 409 | Griseofulvin (238364) | P50719 | |
| 410 | Guanabenz (248361) | P08913 | Y |
| 411 | Guanethidine (232402) | P08913 | Y |
| 412 | Guanethidine (232402) | P18089 | Y |
| 413 | Guanethidine (232402) | P18825 | Y |
| 414 | Guanethidine (232402) | P23975 | |
| 415 | Guanethidine (232402) | P25100 | Y |
| 416 | Guanethidine (232402) | P35348 | Y |
| 417 | Guanethidine (232402) | P35368 | Y |
| 418 | Guanfacine (226992) | P08913 | Y |
| 419 | Halazepam (247942) | P14867 | Y |
| 420 | Halazepam (247942) | P30536 | Y |
| 421 | Halofantrine (247531) | Q76NM6 | |
| 422 | Haloperidol (197517) | P14416 | Y |
| 423 | Halothane (238098) | O15554 | |
| 424 | Halothane (238098) | P03886 | |
| 425 | Halothane (238098) | P14867 | Y |
| 426 | Halothane (238098) | P23415 | Y |
| 427 | Halothane (238098) | P30049 | |
| 428 | Halothane (238098) | P42261 | Y |
| 429 | Halothane (238098) | P98194 | |
| 430 | Halothane (238098) | Q5SQR9 | |
| 431 | Hesperetin (237072) | O75908 | |
| 432 | Hesperetin (237072) | P35610 | |
| 433 | Hesperetin (237072) | P55157 | |
| 434 | Hexachlorophene (232074) | P06149 | |
| 435 | Hexylcaine (122651) | Q14524 | |
| 436 | Hexylcaine (122651) | Q9Y5Y9 | |
| 437 | Hydrochlorothiazide (74591) | P00915 | |
| 438 | Hydrochlorothiazide (74591) | P00918 | |
| 439 | Hydrochlorothiazide (74591) | P22748 | |
| 440 | Hydrochlorothiazide (74591) | P55017 | |
| 441 | Hydrochlorothiazide (74591) | Q12791 | |
| 442 | Hydrocodone (250556) | P35372 | Y |
| 443 | Hydrocodone (250556) | P41143 | Y |
| 444 | Hydrocodone (250556) | P41145 | Y |
| 445 | Hydrocortisone (16228) | P04083 | |
| 446 | Hydrocortisone (16228) | P04150 | Y |
| 447 | Hydromorphone (250603) | P35372 | Y |
| 448 | Hydromorphone (250603) | P41143 | Y |
| 449 | Hydromorphone (250603) | P41145 | Y |
| 450 | Hydroxyurea (247947) | P23921 | |
| 451 | Hydroxyzine (250626) | P35367 | Y |
| 452 | Hyoscyamine (233146) | P08172 | Y |
| 453 | Hyoscyamine (233146) | P11229 | Y |
| 454 | Ibuprofen (233882) | P23319 | |

FIG. 12K

| Index | Drug names (NIST ID) | UniProt ID | receptor |
|---|---|---|---|
| 455 | Ibuprofen (233882) | P35354 | |
| 456 | Idoxuridine (230829) | P04293 | |
| 457 | Imipramine (250696) | P23975 | |
| 458 | Imipramine (250696) | P30542 | Y |
| 459 | Imipramine (250696) | P31645 | |
| 460 | Indapamide (248685) | P15382 | |
| 461 | Indapamide (248685) | P51787 | |
| 462 | Indomethacin (107188) | P23319 | |
| 463 | Indomethacin (107188) | P35354 | |
| 464 | Ipratropium (121219) | P08172 | Y |
| 465 | Ipratropium (121219) | P11229 | Y |
| 466 | Isocarboxazid (250701) | P21397 | |
| 467 | Isocarboxazid (250701) | P27338 | |
| 468 | Isoetharine (247952) | P08588 | Y |
| 469 | Isoflurane (163170) | P03886 | |
| 470 | Isoflurane (163170) | P14867 | Y |
| 471 | Isoflurane (163170) | P23415 | Y |
| 472 | Isoflurane (163170) | P30049 | |
| 473 | Isoflurane (163170) | P42261 | Y |
| 474 | Isoflurane (163170) | P98194 | |
| 475 | Isoflurane (163170) | Q09470 | |
| 476 | Isoflurophate (226257) | P06276 | |
| 477 | Isoniazid (228778) | P0A5Y6 | |
| 478 | Isoniazid (228778) | Q08129 | |
| 479 | Isoproterenol (246203) | P07550 | Y |
| 480 | Isoproterenol (246203) | P08588 | Y |
| 481 | Isosorbide Dinitrate (298706) | P16066 | Y |
| 482 | Isradipine (121153) | P54289 | Y |
| 483 | Ketamine (157938) | Q8TCU5 | Y |
| 484 | Ketoprofen (248419) | P23319 | |
| 485 | Ketoprofen (248419) | P35354 | |
| 486 | Ketorolac (247570) | P23319 | |
| 487 | Ketorolac (247570) | P35354 | |
| 488 | Ketotifen Fumarate (247227) | P35367 | Y |
| 489 | Ketotifen Fumarate (247227) | Q13946 | |
| 490 | Ketotifen Fumarate (247227) | Q9NP56 | |
| 491 | Labetalol (248725) | P07550 | Y |
| 492 | Labetalol (248725) | P08588 | Y |
| 493 | Labetalol (248725) | P35348 | Y |
| 494 | Labetalol (248725) | P35368 | Y |
| 495 | Levallorphan (246652) | P35372 | Y |
| 496 | Levallorphan (246652) | Q15822 | Y |
| 497 | Levobunolol (121213) | P07550 | Y |
| 498 | Levobunolol (121213) | P08588 | Y |
| 499 | Levodopa (229075) | P14416 | Y |
| 500 | Levodopa (229075) | P21728 | Y |

FIG. 12L

| Index | Drug names (NIST ID) | UniProt ID | receptor |
|---|---|---|---|
| 501 | Levomethadyl Acetate (58788) | P35372 | Y |
| 502 | Levorphanol (246478) | P35372 | Y |
| 503 | Lidocaine (113841) | Q14524 | |
| 504 | Lidocaine (113841) | Q9Y5Y9 | |
| 505 | Lindane (122234) | Q75NA5 | |
| 506 | Loperamide (247826) | O00555 | |
| 507 | Loperamide (247826) | O15399 | Y |
| 508 | Loperamide (247826) | P35372 | Y |
| 509 | Loperamide (247826) | P62158 | |
| 510 | Loperamide (247826) | Q12879 | Y |
| 511 | Loperamide (247826) | Q13224 | Y |
| 512 | Loperamide (247826) | Q14957 | Y |
| 513 | Loratadine (247301) | P35367 | Y |
| 514 | Lorazepam (250605) | P30536 | Y |
| 515 | Lovastatin (121161) | P04035 | |
| 516 | Loxapine (246942) | P14416 | Y |
| 517 | Loxapine (246942) | P28223 | Y |
| 518 | Malathion (118987) | P07140 | |
| 519 | Maprotiline (246615) | P23975 | |
| 520 | Maprotiline (246615) | P35348 | Y |
| 521 | Maprotiline (246615) | P35367 | Y |
| 522 | Marinol (313141) | P21554 | Y |
| 523 | Mazindol (247692) | P23975 | |
| 524 | Mazindol (247692) | Q01959 | |
| 525 | Mebendazole (120797) | P50719 | |
| 526 | Mecamylamine (248629) | Q15822 | Y |
| 527 | Meclizine (247693) | P35367 | Y |
| 528 | Medroxyprogesterone (248042) | P03372 | Y |
| 529 | Medroxyprogesterone (248042) | P06401 | Y |
| 530 | Mefenamic acid (298720) | P23219 | |
| 531 | Mefenamic acid (298720) | P35354 | |
| 532 | Mefloquine (247457) | P69905 | |
| 533 | Megestrol (291988) | P03372 | Y |
| 534 | Megestrol (291988) | P06401 | Y |
| 535 | Melatonin (235344) | P48039 | Y |
| 536 | Meperidine (250571) | P41145 | Y |
| 537 | Meperidine (250571) | Q8TCU5 | Y |
| 538 | Mephenytoin (113831) | Q14524 | |
| 539 | Mepivacaine (113842) | Q9Y5Y9 | |
| 540 | Mequitazine (120802) | P35367 | Y |
| 541 | Mercaptopurine (230460) | P00491 | |
| 542 | Mercaptopurine (230460) | P00492 | |
| 543 | Mesalamine (229892) | P23319 | |
| 544 | Mesalamine (229892) | P35354 | |
| 545 | Mesoridazine (247076) | P14416 | Y |
| 546 | Mesoridazine (247076) | P28223 | Y |

FIG. 12 M

| Index | Drug names (NIST ID) | UniProt ID | receptor |
|---|---|---|---|
| 547 | Metaproterenol (248040) | P07550 | Y |
| 548 | Metaraminol (248431) | P35348 | Y |
| 549 | Metformin (238414) | Q9Y478 | |
| 550 | Methacycline (248038) | P0A7J3 | |
| 551 | Methadone (195723) | P35372 | Y |
| 552 | Methadone (195723) | Q8TCU5 | Y |
| 553 | Methadone (195723) | Q9GZZ6 | Y |
| 554 | Methantheline (193105) | P11229 | Y |
| 555 | Metharbital (42422) | P14867 | Y |
| 556 | Methazolamide (248035) | P00915 | |
| 557 | Methdilazine (290506) | P35367 | Y |
| 558 | Methimazole (236047) | P07202 | |
| 559 | Methohexital (247803) | P14867 | Y |
| 560 | Methohexital (247803) | P17787 | Y |
| 561 | Methohexital (247803) | P23415 | Y |
| 562 | Methohexital (247803) | Q15822 | Y |
| 563 | Methotrexate (75950) | P00374 | |
| 564 | Methoxamine (246208) | P35348 | Y |
| 565 | Methoxyflurane (248779) | P03886 | |
| 566 | Methoxyflurane (248779) | P14867 | Y |
| 567 | Methoxyflurane (248779) | P23415 | Y |
| 568 | Methoxyflurane (248779) | P30049 | |
| 569 | Methoxyflurane (248779) | P42261 | Y |
| 570 | Methoxyflurane (248779) | P98194 | |
| 571 | Methoxyflurane (248779) | Q09470 | |
| 572 | Methyclothiazide (16156) | P00915 | |
| 573 | Methyclothiazide (16156) | P00918 | |
| 574 | Methyclothiazide (16156) | P05023 | |
| 575 | Methyclothiazide (16156) | P22748 | |
| 576 | Methyclothiazide (16156) | Q12791 | |
| 577 | Methyclothiazide (16156) | Q13621 | |
| 578 | Methyldopa (246206) | P08913 | Y |
| 579 | Methylergonovine (248696) | P21728 | Y |
| 580 | Methylphenidate (113829) | P23975 | |
| 581 | Methylphenidate (113829) | Q01959 | |
| 582 | Methylprednisolone (247062) | P04083 | |
| 583 | Methylprednisolone (247062) | P04150 | Y |
| 584 | Methyprylon (107182) | P14867 | Y |
| 585 | Methysergide (248028) | P28223 | Y |
| 586 | Metoclopramide (160689) | P11229 | Y |
| 587 | Metoclopramide (160689) | P14416 | Y |
| 588 | Metolazone (248026) | Q13621 | |
| 589 | Metoprolol (246551) | P08588 | Y |
| 590 | Metronidazole (236890) | O30585 | |
| 591 | Metronidazole (236890) | P29166 | |
| 592 | Metyrosine (248728) | P07101 | |

FIG. 12 N

| Index | Drug names (NIST ID) | UniProt ID | receptor |
|---|---|---|---|
| 593 | Mexiletine (248218) | Q14524 | |
| 594 | Miconazole (107110) | P50859 | |
| 595 | Midazolam (248238) | P14867 | Y |
| 596 | Milrinone (120312) | Q07343 | |
| 597 | Minaprine (248239) | P14416 | Y |
| 598 | Minaprine (248239) | P21728 | Y |
| 599 | Minaprine (248239) | P28223 | Y |
| 600 | Minaprine (248239) | P28335 | Y |
| 601 | Minaprine (248239) | P31645 | |
| 602 | Minaprine (248239) | P41595 | Y |
| 603 | Minocycline (248023) | P0A7V8 | |
| 604 | Minocycline (248023) | P0A7X3 | |
| 605 | Minoxidil (248022) | P48048 | |
| 606 | Mirtazapine (247432) | P08913 | Y |
| 607 | Mirtazapine (247432) | P28223 | Y |
| 608 | Mirtazapine (247432) | P28335 | Y |
| 609 | Mirtazapine (247432) | P46098 | Y |
| 610 | Mitotane (119004) | P10109 | |
| 611 | Mitotane (119004) | P15538 | |
| 612 | Mitoxantrone (131658) | P11388 | |
| 613 | Moclobemide (247280) | P21397 | |
| 614 | Morphine (42472) | P35372 | Y |
| 615 | Nabilone (248241) | P21554 | Y |
| 616 | Nabilone (248241) | P34972 | Y |
| 617 | Nabumetone (292131) | P23319 | |
| 618 | Nabumetone (292131) | P35354 | |
| 619 | Nadolol (75219) | P07550 | Y |
| 620 | Nadolol (75219) | P08588 | Y |
| 621 | Nafcillin (248018) | Q8XJ01 | |
| 622 | Nalbuphine (248211) | P35372 | Y |
| 623 | Nalbuphine (248211) | P41143 | Y |
| 624 | Nalbuphine (248211) | P41145 | Y |
| 625 | Naloxone (246940) | P35372 | Y |
| 626 | Naltrexone (247882) | P35372 | Y |
| 627 | Nandrolone Phenpropionate (248687) | P10275 | Y |
| 628 | Naproxen (237147) | P23319 | |
| 629 | Naproxen (237147) | P35354 | |
| 630 | Nefazodone (247544) | P23975 | |
| 631 | Nefazodone (247544) | P28223 | Y |
| 632 | Nefazodone (247544) | P31645 | |
| 633 | Nefazodone (247544) | P35348 | Y |
| 634 | Niacin (233225) | P40261 | |
| 635 | Niacin (233225) | Q15274 | |
| 636 | Niacin (233225) | Q8TDS4 | Y |
| 637 | Nicardipine (247266) | Q13936 | |

FIG. 12O

| Index | Drug names (NIST ID) | UniProt ID | receptor |
|---|---|---|---|
| 638 | Nicotine (281629) | Q15822 | Y |
| 639 | Nifedipine (158530) | P54289 | Y |
| 640 | Nimodipine (247285) | Q06432 | |
| 641 | Nisoldipine (248260) | O00555 | |
| 642 | Nitrendipine (120451) | Q06432 | |
| 643 | Nitric Oxide (31) | P16066 | Y |
| 644 | Nitrofurantoin (290698) | P0A7R5 | |
| 645 | Nitrofurantoin (290698) | P17117 | |
| 646 | Nitrofurazone (75963) | P06715 | |
| 647 | Nitrofurazone (75963) | P07003 | |
| 648 | Nitrofurazone (75963) | P61889 | |
| 649 | Nitrofurazone (75963) | P77390 | |
| 650 | Nitroglycerin (246295) | P16066 | Y |
| 651 | Norethindrone (234126) | P06401 | Y |
| 652 | Norfloxacin (148019) | P0AES6 | |
| 653 | Norfloxacin (148019) | P72525 | |
| 654 | Norgestrel (246859) | P03372 | Y |
| 655 | Norgestrel (246859) | P06401 | Y |
| 656 | Norgestrel (246859) | P35348 | Y |
| 657 | Nortriptyline (247889) | P23975 | |
| 658 | Nortriptyline (247889) | P31645 | |
| 659 | Olanzapine (281161) | P08172 | Y |
| 660 | Olanzapine (281161) | P08173 | Y |
| 661 | Olanzapine (281161) | P08912 | Y |
| 662 | Olanzapine (281161) | P11229 | Y |
| 663 | Olanzapine (281161) | P14416 | Y |
| 664 | Olanzapine (281161) | P20309 | Y |
| 665 | Olanzapine (281161) | P21728 | Y |
| 666 | Olanzapine (281161) | P21917 | Y |
| 667 | Olanzapine (281161) | P28223 | Y |
| 668 | Olanzapine (281161) | P28335 | Y |
| 669 | Olanzapine (281161) | P35367 | Y |
| 670 | Orphenadrine (290525) | P35367 | Y |
| 671 | Orphenadrine (290525) | Q8TCU5 | Y |
| 672 | Ouabain (128089) | P05023 | |
| 673 | Oxandrolone (313196) | P10275 | Y |
| 674 | Oxaprozin (72485) | P35354 | |
| 675 | Oxazepam (250610) | P14867 | Y |
| 676 | Oxybuprocaine (133995) | Q9Y5Y9 | |
| 677 | Oxybutynin (248178) | P11229 | Y |
| 678 | Oxycodone (250611) | P35372 | Y |
| 679 | Oxycodone (250611) | P41143 | Y |
| 680 | Oxycodone (250611) | P41145 | Y |
| 681 | Oxymetazoline (113855) | P08913 | Y |
| 682 | Oxymetazoline (113855) | P35348 | Y |
| 683 | Oxymorphone (250612) | P35372 | Y |

FIG. 12 P

| Index | Drug names (NIST ID) | UniProt ID | receptor |
|---|---|---|---|
| 684 | Oxyphencyclimine (248139) | P08172 | Y |
| 685 | Oxyphencyclimine (248139) | P11229 | Y |
| 686 | Oxyphencyclimine (248139) | P20309 | Y |
| 687 | Oxytetracycline (248113) | P0A7V8 | |
| 688 | Oxytetracycline (248113) | P0A7X3 | |
| 689 | Paclitaxel (131606) | P10415 | |
| 690 | Paclitaxel (131606) | Q9H4B7 | |
| 691 | Papaverine (291096) | Q07343 | |
| 692 | Paramethadione (247999) | Q9P0X4 | |
| 693 | Paroxetine (247287) | P31645 | |
| 694 | Penicillamine (231231) | P04206 | |
| 695 | Penicillamine (231231) | P29466 | |
| 696 | Penicillin V (256457) | Q8XJ01 | |
| 697 | Pentazocine (125798) | P35372 | Y |
| 698 | Pentobarbital (244543) | P14867 | Y |
| 699 | Pentostatin (131639) | P00813 | |
| 700 | Pentoxifylline (248838) | Q07343 | |
| 701 | Pergolide (247504) | P14416 | Y |
| 702 | Pergolide (247504) | P21728 | Y |
| 703 | Perhexiline (120895) | P23786 | |
| 704 | Perhexiline (120895) | P50416 | |
| 705 | Perphenazine (241782) | P14416 | Y |
| 706 | Perphenazine (241782) | P21728 | Y |
| 707 | Perphenazine (241782) | P35348 | Y |
| 708 | Phenacemide (52708) | P35498 | |
| 709 | Phenelzine (121438) | P21397 | |
| 710 | Phenformin (256456) | Q9Y478 | |
| 711 | Phenindione (236131) | P00734 | |
| 712 | Phenmetrazine (113870) | P21397 | |
| 713 | Phenmetrazine (113870) | P23975 | |
| 714 | Phenmetrazine (113870) | Q01959 | |
| 715 | Phenobarbitone (250543) | P14867 | Y |
| 716 | Phenoxybenzamine (290787) | P35348 | Y |
| 717 | Phenprocoumon (286539) | Q9BQB6 | |
| 718 | Phentermine (250588) | P23975 | |
| 719 | Phentermine (250588) | Q01959 | |
| 720 | Phentolamine (248099) | P08913 | Y |
| 721 | Phenylbutazone (14618) | P35354 | |
| 722 | Phenylbutazone (14618) | Q16647 | |
| 723 | Phenylephrine (232105) | P35348 | Y |
| 724 | Phenylpropanolamine (250631) | P08913 | Y |
| 725 | Phenylpropanolamine (250631) | P35348 | Y |
| 726 | Phenytoin (232857) | Q14524 | |
| 727 | Physostigmine (221137) | P06276 | |
| 728 | Phytonadione (233846) | P38435 | |
| 729 | Picrotoxin (298767) | P14867 | Y |

FIG. 12 Q

| Index | Drug names (NIST ID) | UniProt ID | receptor |
|---|---|---|---|
| 730 | Picrotoxin (298767) | P24046 | Y |
| 731 | Pilocarpine (248003) | P11229 | Y |
| 732 | Pimozide (248701) | O43497 | |
| 733 | Pimozide (248701) | P14416 | Y |
| 734 | Pimozide (248701) | P41143 | Y |
| 735 | Pindolol (235693) | P07550 | Y |
| 736 | Pindolol (235693) | P08588 | Y |
| 737 | Piperazine (229316) | Q8ITG2 | Y |
| 738 | Pirenzepine (247006) | P11229 | Y |
| 739 | Piroxicam (298765) | P23219 | |
| 740 | Praziquantel (292191) | P08515 | |
| 741 | Prazosin (107105) | P35348 | Y |
| 742 | Prednisolone (234176) | P08185 | Y |
| 743 | Prednisone (236144) | P04083 | |
| 744 | Prednisone (236144) | P04150 | Y |
| 745 | Prilocaine (113845) | Q14524 | |
| 746 | Primaquine (92433) | P69905 | |
| 747 | Primidone (244337) | P14867 | Y |
| 748 | Probenecid (246675) | O95820 | |
| 749 | Procainamide (125801) | Q14524 | |
| 750 | Procaine (238047) | P46098 | Y |
| 751 | Procaine (238047) | Q01959 | |
| 752 | Procaine (238047) | Q8TCU5 | Y |
| 753 | Procaine (238047) | Q9GZZ6 | Y |
| 754 | Procaine (238047) | Q9Y5Y9 | |
| 755 | Prochlorperazine (250629) | P14416 | Y |
| 756 | Prochlorperazine (250629) | P28223 | Y |
| 757 | Prochlorperazine (250629) | P35367 | Y |
| 758 | Procyclidine (246695) | P08172 | Y |
| 759 | Procyclidine (246695) | P08173 | Y |
| 760 | Procyclidine (246695) | P11229 | Y |
| 761 | Progesterone (62036) | P03372 | Y |
| 762 | Progesterone (62036) | P06401 | Y |
| 763 | Proguanil (298762) | P13922 | |
| 764 | Promazine (292167) | P08172 | Y |
| 765 | Promazine (292167) | P08173 | Y |
| 766 | Promazine (292167) | P08912 | Y |
| 767 | Promazine (292167) | P11229 | Y |
| 768 | Promazine (292167) | P14416 | Y |
| 769 | Promazine (292167) | P20309 | Y |
| 770 | Promazine (292167) | P21728 | Y |
| 771 | Promazine (292167) | P21917 | Y |
| 772 | Promazine (292167) | P25100 | Y |
| 773 | Promazine (292167) | P28223 | Y |
| 774 | Promazine (292167) | P28335 | Y |
| 775 | Promazine (292167) | P35348 | Y |

FIG. 12 R

| Index | Drug names (NIST ID) | UniProt ID | receptor |
|---|---|---|---|
| 776 | Promazine (292167) | P35367 | Y |
| 777 | Promazine (292167) | P35368 | Y |
| 778 | Promethazine (291997) | P08172 | Y |
| 779 | Promethazine (291997) | P08173 | Y |
| 780 | Promethazine (291997) | P08912 | Y |
| 781 | Promethazine (291997) | P11229 | Y |
| 782 | Promethazine (291997) | P14416 | Y |
| 783 | Promethazine (291997) | P20309 | Y |
| 784 | Promethazine (291997) | P28223 | Y |
| 785 | Promethazine (291997) | P35348 | Y |
| 786 | Promethazine (291997) | P35367 | Y |
| 787 | Propafenone (246996) | Q12809 | |
| 788 | Propafenone (246996) | Q14524 | |
| 789 | Proparacaine (248009) | Q9Y5Y9 | |
| 790 | Propiomazine (246995) | P14416 | Y |
| 791 | Propiomazine (246995) | P28223 | Y |
| 792 | Propofol (227977) | P14867 | Y |
| 793 | Propoxyphene (312352) | P35372 | Y |
| 794 | Propoxyphene (312352) | P41143 | Y |
| 795 | Propoxyphene (312352) | P41145 | Y |
| 796 | Propranolol (158021) | P07550 | Y |
| 797 | Propranolol (158021) | P08588 | Y |
| 798 | Propylthiouracil (290664) | P07202 | |
| 799 | Protriptyline (292033) | P23975 | |
| 800 | Protriptyline (292033) | P31645 | |
| 801 | Pseudoephedrine (246007) | P07550 | Y |
| 802 | Pseudoephedrine (246007) | P08913 | Y |
| 803 | Pseudoephedrine (246007) | P35348 | Y |
| 804 | Pyrazinamide (118636) | Q11195 | |
| 805 | Pyridostigmine (226928) | P22303 | |
| 806 | Pyridoxine (228913) | O00764 | |
| 807 | Pyridoxine (228913) | P34896 | |
| 808 | Pyridoxine (228913) | P35520 | |
| 809 | Pyridoxine (228913) | Q96GD0 | |
| 810 | Pyridoxine (228913) | Q9NVS9 | |
| 811 | Pyridoxine (228913) | Q9Y617 | |
| 812 | Pyrimethamine (246424) | P13922 | |
| 813 | Quinidine (125804) | Q14524 | |
| 814 | Quinine (107180) | P69905 | |
| 815 | Ranitidine (120443) | P25021 | Y |
| 816 | Remoxipride (247514) | P14416 | Y |
| 817 | Rescinnamine (247167) | P12821 | |
| 818 | Reserpine (248144) | Q05940 | |
| 819 | Ribavirin (213081) | P16502 | |
| 820 | Ribavirin (213081) | P20839 | |
| 821 | Ribavirin (213081) | P22413 | |

FIG. 12 S

| Index | Drug names (NIST ID) | UniProt ID | receptor |
|---|---|---|---|
| 822 | Ribavirin (213081) | P26676 | |
| 823 | Ribavirin (213081) | P49902 | |
| 824 | Ribavirin (213081) | P55263 | |
| 825 | Riboflavin (120239) | P30043 | |
| 826 | Riboflavin (120239) | Q969G6 | |
| 827 | Rimantadine (273008) | P10920 | |
| 828 | Ritodrine (248145) | P07550 | Y |
| 829 | Scopolamine (234229) | P11229 | Y |
| 830 | Secobarbital (232637) | P14867 | Y |
| 831 | Selegiline (247283) | P27338 | |
| 832 | Sertraline (247231) | P31645 | |
| 833 | Sevoflurane (308798) | P03886 | |
| 834 | Sevoflurane (308798) | P14867 | Y |
| 835 | Sevoflurane (308798) | P23415 | Y |
| 836 | Sevoflurane (308798) | P30049 | |
| 837 | Sevoflurane (308798) | P42261 | Y |
| 838 | Sevoflurane (308798) | P98194 | |
| 839 | Sevoflurane (308798) | Q09470 | |
| 840 | Sirolimus (131640) | P41145 | Y |
| 841 | Sirolimus (131640) | P62942 | |
| 842 | Spectinomycin (248735) | P0A7S3 | |
| 843 | Spironolactone (153009) | P30556 | Y |
| 844 | Sufentanil (248535) | P35372 | Y |
| 845 | Sulfacetamide (242149) | P05041 | |
| 846 | Sulfadiazine (248149) | Q08210 | |
| 847 | Sulfamethizole (236955) | P0AC13 | |
| 848 | Sulfamethoxazole (236956) | P08192 | |
| 849 | Sulfametopyrazine (120977) | Q08210 | |
| 850 | Sulfanilamide (228509) | P37254 | |
| 851 | Sulfapyridine (232444) | P0C002 | |
| 852 | Sulfasalazine (248712) | P24752 | |
| 853 | Sulfasalazine (248712) | Q9UPY5 | |
| 854 | Sulfinpyrazone (107193) | P33527 | |
| 855 | Sulfisoxazole (242145) | Q08210 | |
| 856 | Sulindac (215720) | P35354 | |
| 857 | Sulpiride (248255) | P14416 | Y |
| 858 | Sumatriptan (247581) | P28221 | Y |
| 859 | Sumatriptan (247581) | P28222 | Y |
| 860 | Suprofen (159496) | P23319 | |
| 861 | Suprofen (159496) | P35354 | |
| 862 | Tacrine (291000) | P22303 | |
| 863 | Tamoxifen (248059) | P03372 | Y |
| 864 | Temazepam (248966) | P30536 | Y |
| 865 | Teniposide (131633) | P11388 | |
| 866 | Terazosin (121255) | P35348 | Y |
| 867 | Terazosin (121255) | P35368 | Y |

FIG. 12 T

| Index | Drug names (NIST ID) | UniProt ID | receptor |
|---|---|---|---|
| 868 | Terbutaline (298780) | P07550 | Y |
| 869 | Terfenadine (248740) | P35367 | Y |
| 870 | Testolactone (247866) | P11511 | |
| 871 | Testosterone (62026) | P10275 | Y |
| 872 | Tetracycline (153011) | P0A7V8 | |
| 873 | Tetracycline (153011) | P0A7X3 | |
| 874 | Thalidomide (291688) | P01375 | |
| 875 | Theophylline (118946) | P29275 | Y |
| 876 | Theophylline (118946) | Q07343 | |
| 877 | Theophylline (118946) | Q14432 | |
| 878 | Thiabendazole (118975) | P00363 | |
| 879 | Thiamine (228577) | O60779 | |
| 880 | Thiamine (228577) | P29401 | |
| 881 | Thiamine (228577) | P51854 | |
| 882 | Thiamine (228577) | Q9BU02 | |
| 883 | Thiamine (228577) | Q9H3S4 | |
| 884 | Thiamylal (246459) | P14867 | Y |
| 885 | Thiethylperazine (298783) | P14416 | Y |
| 886 | Thiethylperazine (298783) | P28223 | Y |
| 887 | Thiethylperazine (298783) | P35348 | Y |
| 888 | Thioguanine (226995) | P00492 | |
| 889 | Thioguanine (226995) | P20839 | |
| 890 | Thioguanine (226995) | Q06203 | |
| 891 | Thiopental (42425) | Q693P7 | Y |
| 892 | Thioridazine (248121) | P14416 | Y |
| 893 | Thioridazine (248121) | P21728 | Y |
| 894 | Thioridazine (248121) | P28223 | Y |
| 895 | Thioridazine (248121) | P35348 | Y |
| 896 | Ticlopidine (247263) | Q9H244 | Y |
| 897 | Timolol (246889) | P07550 | Y |
| 898 | Timolol (246889) | P08588 | Y |
| 899 | Tioconazole (121260) | P10614 | |
| 900 | Tizanidine (162088) | P08913 | Y |
| 901 | Tobramycin (235674) | P0A7S3 | |
| 902 | Tocainide (246120) | Q14524 | |
| 903 | Tolazamide (248643) | P48048 | |
| 904 | Tolazoline (245997) | P35348 | Y |
| 905 | Tolbutamide (190858) | P48048 | |
| 906 | Tolbutamide (190858) | Q09428 | Y |
| 907 | Tolmetin (80024) | P23319 | |
| 908 | Tolmetin (80024) | P35354 | |
| 909 | Topotecan (131707) | Q969P6 | |
| 910 | Tramadol (158431) | P23975 | |
| 911 | Tramadol (158431) | P35372 | Y |
| 912 | Tranexamic Acid (229986) | P00747 | |
| 913 | Tranylcypromine (3091) | P21397 | |

FIG. 12U

| Index | Drug names (NIST ID) | UniProt ID | receptor |
|---|---|---|---|
| 914 | Trazodone (248796) | P08913 | Y |
| 915 | Trazodone (248796) | P23975 | |
| 916 | Trazodone (248796) | P28223 | Y |
| 917 | Trazodone (248796) | P31645 | |
| 918 | Trazodone (248796) | P35348 | Y |
| 919 | Trazodone (248796) | P35367 | Y |
| 920 | Tretinoin (51834) | P10276 | Y |
| 921 | Tretinoin (51834) | P10826 | Y |
| 922 | Tretinoin (51834) | P13631 | Y |
| 923 | Triamcinolone (291995) | P04083 | |
| 924 | Triamcinolone (291995) | P08185 | Y |
| 925 | Triamterene (241809) | Q13621 | |
| 926 | Triazolam (79742) | P30536 | Y |
| 927 | Trichlormethiazide (234355) | P00915 | |
| 928 | Trichlormethiazide (234355) | P00918 | |
| 929 | Trichlormethiazide (234355) | P05023 | |
| 930 | Trichlormethiazide (234355) | P22748 | |
| 931 | Trichlormethiazide (234355) | Q12791 | |
| 932 | Trichlormethiazide (234355) | Q13621 | |
| 933 | Trifluoperazine (17112) | P14416 | Y |
| 934 | Trifluoperazine (17112) | P35348 | Y |
| 935 | Triflupromazine (113868) | P08172 | Y |
| 936 | Triflupromazine (113868) | P11229 | Y |
| 937 | Triflupromazine (113868) | P14416 | Y |
| 938 | Triflupromazine (113868) | P21728 | Y |
| 939 | Triflupromazine (113868) | P41595 | Y |
| 940 | Trihexyphenidyl (244993) | P11229 | Y |
| 941 | Trilostane (298789) | P14060 | |
| 942 | Trimeprazine (42348) | P35367 | Y |
| 943 | Trimethadione (113821) | O43497 | |
| 944 | Trimethoprim (247707) | P08192 | |
| 945 | Trimethoprim (247707) | Q27713 | |
| 946 | Trimipramine (235686) | P23975 | |
| 947 | Trimipramine (235686) | P31645 | |
| 948 | Tripelennamine (250622) | P35367 | Y |
| 949 | Triprolidine (291072) | P35367 | Y |
| 950 | Tropicamide (248908) | P08173 | Y |
| 951 | Tubocurarine (234187) | Q15822 | Y |
| 952 | Valproic Acid (191428) | P80404 | |
| 953 | Venlafaxine (247381) | P23975 | |
| 954 | Venlafaxine (247381) | P31645 | |
| 955 | Verapamil (247152) | P00915 | |
| 956 | Verapamil (247152) | Q14524 | |
| 957 | Vitamin A (238604) | O94788 | |
| 958 | Vitamin A (238604) | P00352 | |
| 959 | Vitamin A (238604) | P02753 | |

FIG. 12 V

| Index | Drug names (NIST ID) | UniProt ID | receptor |
|---|---|---|---|
| 960 | Vitamin A (238604) | P09455 | |
| 961 | Vitamin A (238604) | P10745 | |
| 962 | Vitamin A (238604) | P12271 | |
| 963 | Vitamin A (238604) | P50120 | |
| 964 | Vitamin A (238604) | P82980 | |
| 965 | Vitamin A (238604) | Q8NBN7 | |
| 966 | Vitamin A (238604) | Q92781 | |
| 967 | Vitamin A (238604) | Q96NR8 | |
| 968 | Vitamin A (238604) | Q96R05 | |
| 969 | Vitamin C (228563) | P13674 | |
| 970 | Vitamin C (228563) | Q02809 | |
| 971 | Vitamin C (228563) | Q9UGH3 | |
| 972 | Vitamin C (228563) | Q9UHI7 | |
| 973 | Warfarin (191650) | Q9BQB6 | |
| 974 | Zidovudine (248197) | P03369 | |
| 975 | Zolpidem (247600) | P14867 | Y |
| 976 | Zolpidem (247600) | P30536 | Y |
| 977 | Zonisamide (247580) | O43497 | |
| 978 | Zonisamide (247580) | P00915 | |
| 979 | Zonisamide (247580) | Q14524 | |
| 980 | Zopiclone (247516) | P30536 | Y |

FIG. 12 W

| type | vector | prec.(%) | sens.(%) | acc.(%) | parameters |
|---|---|---|---|---|---|
| linear | $(F, G_0^{12}, Cl_t)$ | 54.09 ± 0.24 | 53.25 ± 0.29 | 69.76 ± 0.15 | — |
| conc. (RBF) | $(F, G_0^{12}, Cl_t)$ | 74.93 ± 0.26 | 54.55 ± 0.20 | 79.05 ± 0.11 | $\gamma = 2^{-4.375}$ |
| | $(F, G_0^{12}, Cl_d)$ | 68.23 ± 0.29 | 54.97 ± 0.23 | 76.77 ± 0.14 | $\gamma = 2^{-4}$ |
| | $(F, G_0^{12}, Co_d)$ | 75.55 ± 0.25 | 57.50 ± 0.20 | 79.90 ± 0.11 | $\gamma = 2^{-5}$ |
| | $(F, G_0^{12}, Co_t)$ | 72.15 ± 0.25 | 58.40 ± 0.21 | 78.90 ± 0.12 | $\gamma = 2^{-6}$ |
| | $(F, Cl_t)$ | 74.19 ± 0.23 | 58.69 ± 0.19 | 79.70 ± 0.11 | $\gamma = 2^{-4.125}$ |
| | $(G_0^{12}, Cl_t)$ | 72.56 ± 0.25 | 51.36 ± 0.22 | 77.61 ± 0.11 | $\gamma = 2^{-4.625}$ |
| | $(F, Co_d)$ | 73.99 ± 0.24 | 59.18 ± 0.21 | 79.73 ± 0.12 | $\gamma = 2^{-4.625}$ |
| combi. | $(F, G_0^{12}, Cl_t)$ | 75.91 ± 0.21 | 60.71 ± 0.20 | 80.74 ± 0.10 | Table D.9 |

FIG. 13

| gap intensity type | prec.(%) | sens.(%) | acc.(%) | parameters |
|---|---|---|---|---|
| 1 | 75.01 ± 0.28 | 52.83 ± 0.18 | 78.70 ± 0.11 | $C = 16, \gamma = 2^{-4}$ |
| 2 | 74.33 ± 0.23 | 53.24 ± 0.19 | 78.57 ± 0.10 | $C = 16, \gamma = 2^{-4.25}$ |
| 3 | 73.92 ± 0.25 | 55.92 ± 0.21 | 79.01 ± 0.11 | $C = 16, \gamma = 2^{-4.5}$ |
| 4 | 75.71 ± 0.25 | 51.61 ± 0.19 | 78.64 ± 0.10 | $C = 16, \gamma = 2^{-4.125}$ |
| 5 | 74.93 ± 0.26 | 54.55 ± 0.20 | 79.05 ± 0.11 | $C = 16, \gamma = 2^{-4.375}$ |
| 6 | 76.04 ± 0.25 | 51.61 ± 0.18 | 78.73 ± 0.10 | $C = 16, \gamma = 2^{-4.125}$ |

FIG. 14

| # of random pairs | prec.(%) | sens.(%) | acc.(%) |
|---|---|---|---|
| 1000 | 76.20 ± 0.22 | 71.57 ± 0.17 | 74.86 ± 0.17 |
| 2000 | 75.91 ± 0.21 | 60.71 ± 0.20 | 80.74 ± 0.10 |
| 3000 | 75.15 ± 0.23 | 53.97 ± 0.18 | 84.27 ± 0.07 |
| 5000 | 74.63 ± 0.24 | 45.51 ± 0.19 | 88.53 ± 0.05 |
| 8000 | 73.94 ± 0.42 | 37.55 ± 0.19 | 91.74 ± 0.03 |

FIG. 15

| type | vector | prec.(%) | sens.(%) | acc.(%) | parameters |
|---|---|---|---|---|---|
| conc. (RBF) | $(F, G_{15}^{12}, Cl_t)$ | 77.09 ± 0.30 | 57.70 ± 0.27 | 80.31 ± 0.14 | $C = 16, \gamma = 2^{-5}$ |
|  | $(F, G_{15}^{12}, Co_d)$ | 76.41 ± 0.25 | 64.61 ± 0.29 | 81.68 ± 0.14 | $C = 16, \gamma = 2^{-5.75}$ |
| combi | $(F, G_{15}^{12}, Cl_t)$ | 75.49 ± 0.26 | 69.04 ± 0.24 | 82.32 ± 0.13 | Table D.10 |

FIG. 16

(A) Applied to AR drugs dataset

| # of features | TP | FN | TN | FP | prec.(%) | sens.(%) | acc.(%) | parameters |
|---|---|---|---|---|---|---|---|---|
| 5 | 122 | 20 | 274 | 16 | 88.41 | 85.92 | 91.67 | Table D.11 |
| 8 | 126 | 16 | 270 | 20 | 86.30 | 88.73 | 91.67 | Table D.11 |

$(F^n, G_{15}^{12^n}, Cl_t^n)$ in combination expression is used.

(B) Applied to DrugBank dataset

| seq. type | # of features | prec.(%) | sens.(%) | acc.(%) | parameters |
|---|---|---|---|---|---|
| triclust | 5 | 64.75 ± 0.26 | 55.83 ± 0.22 | 75.47 ± 0.14 | Table D.12 |
|  | 50 | 71.40 ± 0.25 | 57.50 ± 0.15 | 78.44 ± 0.11 | Table D.12 |
|  | 198 | 74.48 ± 0.24 | 52.84 ± 0.20 | 78.53 ± 0.10 | Table D.12 |
| dicount | 5 | 64.18 ± 0.26 | 50.10 ± 0.24 | 74.39 ± 0.12 | Table D.12 |
|  | 50 | 70.47 ± 0.23 | 59.42 ± 0.19 | 78.46 ± 0.11 | Table D.12 |
|  | 198 | 74.78 ± 0.23 | 51.39 ± 0.18 | 78.31 ± 0.09 | Table D.12 |

$(F^n, G_0^{12^n}, Cl_t^n (\text{or } Co_d^n))$ in combination expression is used.

FIG. 17

METHOD FOR PREDICTING INTERACTION BETWEEN PROTEIN AND CHEMICAL

This application is the U.S. National Stage of International Application PCT/JP2007/071236, filed Oct. 31, 2007, which claims the benefit of Japanese Application Serial No. JP 2006-297111, filed Oct. 31, 2006.

TECHNICAL FIELD

The present invention relates to a method for predicting an interaction between a protein and a chemical.

BACKGROUND ART

In order to predict interactions between proteins and chemicals, the methods, such as docking analysis, for modeling the three-dimensional structures of such proteins and chemicals to calculate binding energy have been mainly studied. Many commercially available software programs have been developed (H. J. Bohm, The computer program LUDI: A new method for the de novo design of enzyme inhibitors, *J. Comp. Aided. Mol. Des.*, Vol. 6, pp. 61-78, 1992; Y. Z. Chen and C. Y. Ung, Prediction of potential toxicity and side effect protein targets of a small molecule by a ligand-protein inverse docking approach, *J. Mol. Graph. Mod.*, Vol. 20, pp. 199-218, 2001; Y. Z. Chen and D. G. Zhi, Ligand-protein inverse docking and its potential use in computer search of putative protein targets of a small molecule, *Proteins*, Vol. 43, pp. 217-226, 2001; Y. Z. Chen and C. Y. Ung, Computer automated prediction of putative therapeutic and toxicity protein targets of bioactive compounds from chinese medical plants, *Am. J. Chin. Med.*, Vol. 30, pp. 139-154, 2002; Y. Z. Chen, Z. R. Li, and C. Y. Ung, Computational method for drug target search and application in drug discovery, *J. Theor. Comp. Chem.*, Vol. 1, pp. 213-224, 2002; R. L. Desjarlais, R. P. Sheridan an G. L. Seibel, J. S. Dixon, I. D. Kuntz, and R. Venkataraghavan, Using shape complementarity as an initial screen in designing ligands for a receptor-binding site of known three-dimensional structure, *J. Med. Chem.*, Vol. 31, pp. 722-729, 1988; T. E. Ferrin, G. S. Couch, C. C. Huang, E. F. Pellersen, and R. Langridge, An affordable approach to interactive desktop molecular modeling, *J. Mol. Graphics*, Vol. 9; J. Goodford, A computational procedure for determining energetically favorable binding sites on biologically important macromolecules, *J. Med. Chem.*, Vol. 28, pp. 849-857, 1985; G. Jones, P. WIllett, R. C. Glen, A. R. Leach, and R. Taylor, Development and calidation of a genetic algorithm for flexible dicking, *J. Mol. Biol.*, Vol. 267, pp. 727-748, 1997; A. R. Leach and I. D. Kuntz, Conformational analysis of flexible ligands in macromolecular receptors sites, *J. Comput. Chem.*, Vol. 13, pp. 730-748, 1992; A. Miranker and M. Karplus, Functionality maps of binding sites: A multicopy simultaneous search method, *Proteins*, Vol. 11, pp. 29-34, 1991; A. Miranker and M. Karplus, An automated method for dynamic ligand design, *Proteins*, Vol. 23, pp. 472-490, 1995; M. Y. Mizutani, N. Tomioka, and A. Itai, Rational automatic search method for stable docking models of protein and ligand, *J. Mol. Biol.*, Vol. 243, pp. 310-326, 1994; C. M. Oshiro, I. D. Kuntz, and J. S. Dixon, Flexible ligand docking using a genetic algorithm, J. Comp. Aided Mol. Des., Vol. 9, pp. 113-130, 1995; C. M. Oshiro and I. D. Kuntz, Characterization of receptors with a new negative image: Use in molecular docking and lead optimization, *Proteins*, Vol. 30, pp. 321-336, 1998; S. H. Rostein, M. A. Murcko, and A. GenStar, A method for de novo drug design, *J. Comp. Aided Mol. Des.*, Vol. 7, pp. 23-43, 1993; B. K. Shoichet, D. L. Bodian, and I. D. Kuntz, Molecular docking using shape descriptors, *J. Comput. Chem.*, Vol. 13, pp. 380-397, 1992; and M. Zacharias, B. A. Luty, M. E. Davis, and J. A. McCammon, Combined conformational search and finite-difference poisson-boltazmann approach for flexible docking, *J. Mol. Biol.*, Vol. 238, pp. 455-465, 1994). These methods are based on binding energy and therefore are highly reliable.

DISCLOSURE OF INVENTION

Problems to be Solved by the Invention

The character of the methods that they are based on three-dimensional structures is their disadvantage and gives them a limitation, because there are still many proteins with unknown structures although three-dimensional structures have been databased. The number of all biological proteins deposited in, for example, PDB (H. M. Berman, J. Westbrook, Z. Feng, G. Gillil and, T. N. Bhat, H. Weissig, I. N. Shindyalov, and P. E. Bourne, The protein data bank, *Nucleic Acids Res.*, Vol. 28, pp. 235-242, 2000) is only 14243 when proteins having sequences with a homology of 95% or more as determined using blast are regarded as the same. Despite advances in technology, there are many proteins which have not sufficiently analyzed for structure yet. Proteins with unknown structures can be analyzed for structure by a protein structure prediction method or a compound structure prediction method. However, these methods are incomplete yet.

The present invention has been made to provide a versatile method for predicting an unknown interaction between a protein and a chemical.

Means for Solving the Problems

In order to solve the above problems, the inventors have made intensive efforts to identify useful data and to develop a method for processing the data and have then obtained results below.

First, the inventors have investigated versatile and easily available data on proteins and chemicals.

Amino acid sequences are such data as is most available about proteins at present and as is first obtained when a novel protein is discovered.

Chemical formulas and structural formulas are the most satisfactory data on chemicals at present. Upon the discovery of a novel chemical, however, its structural formula needs to be determined by various methods, which is not necessarily easy. In the future, the comprehensive analysis of metabolites will become the most probable way to discover a novel chemical. Then, since comprehensive metabolite-profiling methods currently proposed are based on mass spectroscopy (MS) such as GC/MS (O. Fiehn, J. Kopka, P. Dormann, T. Altmann, R. Trethewey, and L. Willmitzer, Metabolite profiling for plant functional genomics, *Nature Biotechnology*, Vol. 18, pp. 1157-1161, 2000; and N. Glassbrook, C. Beecher, and J. Ryals, Metabolite profiling on the right path, *Nature Biotechnology*, Vol. 18, pp. 1142-1143, 2000) or CE/MS (P. Schmitt-Kopplin and M. Frommberger, Capillary electrophoresis—mass spectrometry: 15 years of developments and applications, *Electrophoresis*, Vol. 24, pp. 3837-3867, 2003; and A. C. Servais, J. Crommen, and M. Fillet, Capillary electrophoresis-mass spectrometry, an attractive tool for drug bioanalysis and biomarker discovery, *Electrophoresis*, Vol. 27, pp. 2616-2629, 2006), the mass spectra of chemicals are probably the most available data for identifying unknown chemicals. At present, there has already existed a database containing the mass spectrum data of about 160000 chemicals National Institute of Standards and Technology).

The inventors have thus investigated statistic processing methods using the above data. That is, the inventors sampled protein-chemical interactions such as protein-chemical couplings and agonistic or antagonistic functional interactions between proteins and chemicals, studied amino acid sequences of available proteins and the mass spectrum data of available chemicals, vectorized the frequency of specific amino acid sequences and the position and intensity of each peak in the mass spectrum data, and applied a support vector machine (SVM) to the vectors and configured a pattern recognizer by training the SVM with the interactions (V. Vapnik, *Statistical Learning Theory*, Wiley, New York, 1998). And the inventors have found that the classification used highly correlates with the classification of bonds or functional interactions. The inventors have completed a method for predicting an unknown interaction between a pair of a protein and a chemical.

The present specification contains at least 19 inventions below.

(1) A method for configuring a pattern recognizer discriminating between a class to which a first pair of a protein and a chemical having a first interaction belong and a class to which a second pair of a protein and a chemical having a second interaction belong includes a step of vectorizing at least one of parameters of mass spectrum data obtained from each chemical into one of vectors $a_1$ to $a_x$ (x is an integer of one or more) and a step of vectorizing each protein into vectors $b_1$ to $b_y$ (y is an integer of one or more). One of the vectors $a_1$ to $a_x$ derived from the chemical is combined with a vector $b_k$ (k is an integer of one to y) derived from the protein paired with the chemical. A support vector machine (SVM) is applied to the combined vectors and trained to learn them.

(2) In the method for configuring a pattern recognizer specified in Item (1), at least one of the mass spectrum data parameters is selected from four parameters that are the position of a peak, the position and intensity of the peak, the distance between two peaks, and the distance between two peaks and their intensities.

(3) In the method for configuring a pattern recognizer specified in Item (1) or (2), the vectors $b_1$ to $b_y$ contain elements of the frequency of a predetermined amino acid sequence appearing in the protein.

(4) In the method for configuring a pattern recognizer specified in any one of Items (1) to (3), one of the vectors derived from each chemical is a vector $F(c)$ given by the following equations:

$$F(c) = (\phi_c(m))_{m \in M} \quad (1)$$

$$\phi_c(m) = \begin{cases} I_c(m) & \text{if } m \in M(c) \\ 0 & \text{otherwise} \end{cases}$$

wherein M is the set of the m/z values of peaks observed from all of the chemicals, M(c) is the set of the m/z values of peaks observed from the chemical of the pair, and I(m) is the intensity of a peak observed from the chemical of the pair.

(5) In the method for configuring a pattern recognizer specified in any one of Items (1) to (3), one of the vectors derived from each chemical is a vector $F'(c)$ given by the following equations:

$$F'(c) = (\phi'_c(m))_{m \in M} \quad (2)$$

$$\phi'_c(m) = \begin{cases} 1 & \text{if } m \in M(c) \\ 0 & \text{otherwise} \end{cases}$$

wherein M is the set of the m/z values of peaks observed from all of the chemicals and M(c) is the set of the m/z values of peaks observed from the chemical of the pair.

(6) In the method for configuring a pattern recognizer specified in any one of Items (1) to (3), one of the vectors derived from each chemical is a vector $G^w_t(c)$ given by the following equations:

$$G^w_t(c) = (\xi_c(m))_{m \in M_g} \quad (3)$$

$$\xi_c(m) = \begin{cases} gap_c(m) & \text{if } m \in M_g(c) \\ 0 & \text{otherwise} \end{cases}$$

wherein Mg is the set of the difference between the m/z values of each two peaks observed from all of the chemicals to be classified, Mg(c) is the set of the difference j−i between the m/z values i and j of each two peaks observed from the chemical of the pair, $$gap_c(m) = \sum_{i; i+m \in M(c)} g_i(m) \quad (4)$$

wherein M(c) is the set of the m/z values of peaks observed from the chemical of the pair, $$\forall i, j; j - i \geq w, I_i, I_j \geq t, \quad (5)$$

$$g_i(j - i) = I_i \times \frac{\ln(I_j)}{\sum_{k; k > i, I_k \geq t} \ln(I_k)}$$

wherein Ii and Ij are the intensities of two peaks observed at m/z values i and j, respectively, t is the threshold of the intensity determined by taking a gap into account, and w is the threshold of the difference j−i between the m/z values of the two peaks observed at the m/z values i and j.

(7) In the method for configuring a pattern recognizer specified in any one of Items (1) to (3), one of the vectors derived from each chemical is a vector $G^{w'}_t(c)$ given by the following equations:

$$G^{w'}_t(c) = (\xi'_c(m))_{m \in M_g} \quad (6)$$

$$\xi'_c(m) = \begin{cases} 1 & \text{if } m \in M_g(c) \\ 0 & \text{otherwise} \end{cases}$$

wherein Mg is the set of the difference between the m/z values of each two peaks observed from all of the chemicals to be classified and Mg(c) is the set of the difference between the m/z values of each two peaks observed from a chemical of a third pair.

(8) In the method for configuring a pattern recognizer specified in any one of Items (1) to (7), the vectors derived from each chemical and the vectors derived from the protein paired with the chemical are combined into a vector $(a_1, b_k)$ or ($a_p$, $a_q$, $b_k$), where l, p, and q are one of 1 to x and k is one of 1 to y; and the support vector machine (SVM) is applied to this vector and trained to learn them.

(9) In the method for configuring a pattern recognizer specified in any one of Items (1) to (7), at least one selected from four parameters that are a physicochemical property, the chemical formula, the structural formula, and the three-dimensional structure of each chemical is vectorized into a vector D; the vectors derived from the chemical, the vectors derived from the protein paired with the chemical, and the vector D are combined into a vector ($a_1$, D, $b_k$) or ($a_p$, $a_q$, D, $b_k$), where l, p, and q are one of 1 to x and k is one of 1 to y; and the support vector machine (SVM) is applied to this vector and trained to learn them.

(10) the method for configuring a pattern recognizer specified in any one of Items (1) to (9), the discrimination function of the support vector machine is given by the following equation:

$$f(c, p) = \text{sign}\left(\sum_{(c_i, p_i) \in SV_s} \alpha_i y_i K(B_{c_i p_i}, B_{cp}) + b^*\right) \quad (7)$$

(11) In the method for configuring a pattern recognizer specified in Item (10), the following equation $K_{conc.}$ (8) is applied to Equation (7):

$$K_{conc.}(B_{a_1 b_1}, B_{a_2 b_2}) = K(a_1, a_2) \cdot K(b_1, b_2) \quad (8)$$

(12) In the method for configuring a pattern recognizer specified in Item (10), the following equation $K_{combi.}$ (9) is applied to Equation (7):

$$K_{combi}(B_{a'_1 b'_1}, B_{a'_2 b'_2}) = K_{aa}(a'_1, a'_2) \cdot K_{bb}(b'_1, b'_2) \cdot K_{ab}(a'_1, b'_2) \cdot K_{ab}(b'_1, a'_2) \quad (9)$$

(13) In the method for configuring a pattern recognizer specified in any one of Items (1) to (12), the support vector machine uses a linear kernel, a polynomial kernel, an RBF (radial basis function) kernel, or a sigmoid kernel.

(14) In the method for configuring a pattern recognizer specified in any one of Items (1) to (13), the interaction is that a protein and a chemical are physically bound to each other, the first interaction is that the protein and the chemical are bound to each other, the second interaction is that the protein and the chemical are not bound to each other, and the protein-chemical pair is classified on the basis of whether the protein and the chemical are bound to each other.

(15) In the method for configuring a pattern recognizer specified in any one of Items (1) to (13), the interaction is that a protein and a chemical are functionally coupled to each other, the first interaction is that the chemical acts as an agonist when being bound to the protein, the second interaction is that the chemical acts as an antagonist when being bound to the protein, and the protein-chemical pair is classified on the basis of whether the chemical acts as an agonist or an antagonist when being bound to the protein.

(16) A method for predicting an interaction between a protein and a chemical includes a step of, with use of a first pair of a protein and a chemical having a first interaction, and a second pair of a protein and a chemical having a second interaction, and a third pair of a protein and chemical to be subjected to prediction, configuring a pattern recognizer, discriminating between a class to which the first pair belong and a class to which the second pair belong, by the method for configuring a pattern recognizer specified in any one of Items (1) to (15); and a step of applying the pattern recognizer to a vector B created from the third pair to determine whether the third pair belong to which one of the two classes.

(17) A method for screening a chemical coupled to a specific protein from a chemical library includes a step of predicting an interaction between the protein and the chemical by applying the predicting method specified in Item (16) to chemicals contained in the chemical library.

(18) A method for screening a protein coupled to a specific chemical from a protein library includes a step of predicting an interaction between the chemical and the protein by applying the predicting method specified in Item (16) to proteins contained in the protein library.

(19) A method for configuring a pattern recognizer discriminating between a class to which a first pair of a protein and a chemical having a first interaction belong and a class to which a second pair of a protein and a chemical having a second interaction belong includes a step of vectorizing at least one of parameters of mass spectrum data obtained from each chemical into one of vectors $a_1$ to $a_x$ (x is an integer of one or more) and a step of training a support vector machine (SVM) with the vectors $a_1$ to $a_x$ derived from the chemical.

BRIEF DESCRIPTION OF DRAWINGS

FIGS. 1A-1M are a list of physicochemical properties of 237 amino acids selected by Venkatarajan et al.

FIG. 2 is a list of five-dimensional vectors expressing 20 types of amino acids expressed by Venkatarajan et al.

FIGS. 3A and 3B are a list of 89 types of clusters obtained by clustering 400 types of dipeptides in an embodiment of the present invention.

FIGS. 4A-4J are a list of 199 types of clusters obtained by clustering 4200 types of tripeptides in an embodiment of the present invention.

FIG. 5 is a table showing the homology between amino acid sequences of proteins belonging to a human AR family.

FIG. 6A is a table showing functional classifications of human AR family proteins and FIG. 6B is an illustration showing coupling schemes of chemicals, coupled to the human AR family proteins, to AR proteins.

FIG. 7 is a table showing the discriminating power of a pattern recognizer configured using different Kernel functions for the operation of an SVM in an embodiment of the present invention.

FIG. 8 is a table showing the discriminating power of a pattern recognizer configured by vectorizing a protein by different vectorization methods in an embodiment of the present invention.

FIG. 9 is a table showing the discriminating power of a pattern recognizer configured by vectorizing a chemical by different vectorization methods in an embodiment of the present invention.

FIG. 10 is a table showing the discriminating power of a pattern recognizer configured by combining a vector derived from a protein with a vector derived from a protein using different combining expressions in an embodiment of the present invention.

FIG. 11A is a table showing the discriminating power of a pattern recognizer configured by taking protein-derived information into account and FIG. 11B is a table showing the discriminating power of a pattern recognizer configured by taking no protein-derived information into account in an embodiment of the present invention.

FIGS. 12A-12W are tables showing features of 980 pairs of chemicals and proteins selected from drug-target protein pairs specified in DrugBank Approved Drug Target Protein Sequences, the mass spectrum data of the chemicals being present in NIST05.

FIG. 13 is a table showing the discriminating power of a pattern recognizer configured using data specified in Drug-Bank Approved Drug Target Protein Sequences in an embodiment of the present invention.

FIG. 14 is a table showing the discriminating power of a pattern recognizer configured by calculating a gap vector by different intensity calculation methods in an embodiment of the present invention.

FIG. 15 is a table showing the discriminating power of a pattern recognizer configured using an increased number of negative samples in an embodiment of the present invention.

FIG. 16 is a table showing the discriminating power of a pattern recognizer configured using a receptor-ligand pair selected from drug-target protein pairs specified in DrugBank Approved Drug Target Protein Sequences.

FIGS. 17A and 17B are tables showing the discriminating power of a pattern recognizer configured using features selected by PCA in an embodiment of the present invention.

BEST MODES FOR CARRYING OUT THE INVENTION

Methods for predicting protein-chemical interactions according to embodiments of the present invention will now be described in detail with reference to examples. The present invention is not limited to the embodiments and the examples.

Objects, features, advantages and ideas of the present invention are apparent for those skilled in the art from the description of the present specification. Those skilled in the art can readily implement the present invention from the description of the present specification. The embodiments and the examples, which are described below in detail, correspond to preferred modes of the present invention, are for illustrative purposes only, and should not be construed as limitative. It is apparent for those skilled in the art that various modifications can be made within the spirit and scope of the present invention on the basis of the description of the present specification.

==Vectorization of Proteins==

A method for vectorizing "y" proteins into vectors $b_1$ to $b_y$ (y is an integer of one or more) is as described below. The method for vectorizing the proteins is not particularly limited. For example, the entire amino acid sequences or partial sequences, such as binding sites, of each protein may be vectorized. Alternatively, the proteins may be vectorized on the basis of the charge of each amino acid residue in the proteins, their hydrophobicity, their surface tension, and/or their three-dimensional structure (J. R. Bock and D. A. Gough, Predicting protein-protein interactinos from primary structure, *Bioinformatics*, Vol. 17, No. 5, pp. 455-460, 2001; C. Yanover and T. Hertz, Predicting protein-peptide binding affinity by learning peptide-peptide distance functions, In RECOMB 2005, pp. 456-471, 2005). An exemplary method for creating a vector C(p) containing elements of the frequencies of features of specific amino acid sequences of the protein is described below using the following equation:

$$C(p) = (\rho_p(c))_{c \in C} \quad (10)$$

$$\rho_p(c) = \begin{cases} \dfrac{f_p(c)}{\sum_{i \in C(p)} f_p(i)} & \text{if } c \in C(p) \\ 0 & \text{otherwise} \end{cases}$$

wherein, C is the set of features c that appear at least once in the proteins to be vectorized and fp(c) is the frequency of a feature c that appears in a protein p.

A usable feature of the amino acid sequences may be the frequency of all combinations of sequences of amino acids of which the number is n (n is a natural number) or may be the frequency of each group obtained by grouping partial sequences on the basis of physicochemical properties. The usable number of amino acids in the amino acid sequences is not particularly limited and partial sequences with two or three amino acids are preferably used because of the number of elements of a vector.

A typical way to select amino acid sequences and a method for creating a vector a are described below. It should be noted that usable features of the amino acid sequences are not limited thereto.

(1) Use of Dipeptides (Sequences of Two Amino Acids)

The following vector is created as a vector C: a vector $C_{od}$ elements of the frequencies of all combinations of sequences of two amino acids (M. Bhasin and G. P. S. Raghava, GPCR pred. and SVM-based method for prediction of families and subfamilies of g-protein coupled receptors, *Nucleic Acids Res.*, Vol. 32, pp. 383-389, 2004). Since there are 20 kinds of amino acids in nature, this vector contains $20^2$ elements, that is, 400 elements.

(2) Use of Tripeptides (Sequences of Three Amino Acids)

The following vector may be created as a vector C: a vector $C_{ot}$ elements of the frequencies of all combinations of sequences of three amino acids. Since there are 20 kinds of amino acids in nature, this vector contains $20^3$ elements, that is, 8000 elements and thus is 8000-dimensional.

Alternatively, a vector containing elements of the frequencies of combinations of sequences of three amino acids may be created without distinguishing the terminal amino acids of each sequence from each other as reported by Martin et al. (S. Martin, D. Roe, and J. L. Faulon, Predicting protein-protein interactions using signature products, *Bioinformatics*, Vol. 21, No. 2, pp. 218-226, 2005). This vector contains 4200 elements as determined from the expression (8000−400)/2+400, and thus is 4200-dimensional.

(3) Use of Diclusts

The following vector may be created as a vector C: a vector $C_{id}$ containing elements of the frequencies of groups obtained by grouping combinations of sequences of two amino acids on the basis of physicochemical properties.

For example, Venkatarajan et al. have determined a five-dimensional vector from 237 physicochemical properties (FIG. 1) of 20 amino acids as described below (M. S. Venkatarajan and W. Braun, New quantitative descriptors of amino acids based on multidimensional scaling of a large number of physical-chemical properties, Journal of Molecular Modeling, Vol. 7, pp. 445-453, 2001).

A value $S_\alpha(i)$ given by the following equation was determined by scaling a parameter $P_\alpha(i)$ of a feature α of an amino acid i with the average $\overline{P}_\alpha$ and standard deviate $\sigma_{P_\alpha}$ of $P_\alpha$ of the 20 amino acids:

$$S_\alpha(i) = \frac{P_\alpha(i) - \overline{P}_\alpha}{\sigma_{P_\alpha}} \quad (11)$$

$$\sigma_{P_\alpha} = \sqrt{\frac{20 \sum_{i=1}^{20} P_\alpha(i)^2 - \left(\sum_{i=1}^{20} P_\alpha(i)\right)^2}{400}}$$

A matrix Q representing the similarity of amino acids was created using $S_\alpha$. The degree $Q_{ij}$ of similarity between the amino acid i and an amino acid j was given by the following equation:

$$Q_{ij} = \sum_{\alpha=1}^{237} S_\alpha(i) \cdot S_\alpha(j) \qquad (12)$$

An eigenvalue λ was then determined such that the following equation held for Q determined as described above and a unit matrix E:

$$QE = \lambda E \qquad (13)$$

Since Q represented a 20-by-20 matrix, 20 λs were determined. $Q_{ij}$, an element of Q, was determined from the eigenvector $E^\mu_i$ of the amino acid i corresponding to an eigenvalue $\lambda_\mu$ and an eigenvector $E^\mu_j$ corresponding to the amino acid j using the following equation:

$$Q_{ij} = \sum_{\mu=1}^{20} \lambda_\mu E^\mu_i E^\mu_j \qquad (14)$$

$Q_{ij}$ was approximated by the following equation using numerical top five eigenvalues λ:

$$Q_{ij} \approx \sum_{\mu=1}^{5} \lambda_\mu E^\mu_i E^\mu_j \qquad (15)$$

Venkatarajan et al. finally expressed the amino acid i with a five-dimensional vector α(i) below using the five eigenvalues and the eigenvectors. The five eigenvalues and the eigenvector of each amino acid are shown in FIG. 2.

$$\alpha(i) = (\sqrt{\lambda_{\mu=1}} E^{\mu=1}_i, \sqrt{\lambda_{\mu=2}} E^{\mu=2}_i, \ldots, \sqrt{\lambda_{\mu=5}} E^{\mu=5}_i) \qquad (16)$$

A physicochemical feature vector $\alpha_d(i, j)$ expressing a dipeptide (i, j) consisting of the amino acid i and the amino acid j is defined by the following equation using the five-dimensional vector obtained above:

$$\alpha_d(ij) = \frac{\alpha(i) + \alpha(j)}{2} \qquad (17)$$

$\alpha_d(i, j)$, which corresponds to 400 types of dipeptides, is clustered by variational Bayesian mixture modelling, whereby 89 types of clusters are obtained. Each of the clusters is used as a feature c contained in C in Equation (10). In an example below, the following package was used: the vabayelMix package (A. E. Teschendorff, Y. Wang, N. L. Barbosa-Morais, J. D. Brenton, and C. Caldas, A variational Bayesian mixture modelling framework for cluster analysis of gene-expression data, *Bioinformatics*, Vol. 21, No. 13, pp. 3025-3033, 2005) of the statistical analysis software R.

In particular, the 89 types of clusters are obtained in such a manner that 400 five-dimensional vectors corresponding to the 400 types of dipeptides are clustered in two stages. In the first stage, the 400 vectors are divided into 25 clusters. In the second stage, vectors belonging to each cluster are clustered, whereby 89 clusters can be obtained from the 25 clusters. Dipeptides contained in the 89 clusters are shown in FIG. 3.

(4) Use of Triclusts

The following vector may be created as a vector C: a vector $C_{lt}$ containing elements of the frequencies of groups obtained by grouping combinations of sequences of three amino acids on the basis of physicochemical properties.

For example, such a three-amino acid sequence $\alpha_s(a_{01}, a_{11}, a_{12})$ as described in Item (2) is defined by the following equation using the five-dimensional vector a(i) described in Item (3):

$$\alpha_s(a_{01}, a_{11}, a_{12}) = \alpha(a_{01}) + \frac{1}{2}\left(\frac{\alpha(a_{11}) + \alpha(a_{12})}{2}\right) \qquad (18)$$

$\alpha_s(a_{01}, a_{11}, a_{12})$, which corresponds to 4200 types of tripeptides, is clustered by variational Bayesian mixture modelling, whereby 199 types of clusters are obtained. Each of the clusters is used as a feature c contained in C in Equation (10). In an example below, the following package was used: the vabayelMix package (A. E. Teschendorff, Y. Wang, N. L. Barbosa-Morais, J. D. Brenton, and C. Caldas, A variational Bayesian mixture modelling framework for cluster analysis of gene-expression data, *Bioinformatics*, Vol. 21, No. 13, pp. 3025-3033, 2005) of the statistical analysis software R.

In particular, the 199 types of clusters are obtained in such a manner that 4200 five-dimensional vectors corresponding to the 4200 types of dipeptides are clustered in two stages. In the first stage, the 4200 vectors are divided into 34 clusters. In the second stage, vectors belonging to each cluster are clustered, whereby 199 clusters can be obtained from the 34 clusters. Dipeptides contained in the 199 clusters are shown in FIG. 4.

==Vectorization of Chemical==

A chemical is vectorized using the mass spectrum of the chemical. That is, at least one of parameters (the number thereof is herein x) of the mass spectrum data is vectorized, whereby vectors $a_1$ to $a_x$ (x is an integer of one or more) may be obtained. It is not limited which parameter is selected. For example, in a mass spectrum, information about the position and intensity of a peak observed may be digitized into a fragment vector (F) and information about the distance between peaks observed and the intensity of each peak may be digitized into a gap vector (G).

(1) Creation of Fragment Vector

For example, a vector F(c) corresponding to the mass spectrum of a chemical c is given by the following equations when both the position and intensity of an observed peak are taken into account:

$$F(c) = (\phi_c(m))_{m \in M} \qquad (19)$$

$$\phi_c(m) = \begin{cases} I_c(m) & \text{if } m \in M(c) \\ 0 & \text{otherwise} \end{cases}$$

A vector F'(c) is given by the following equations when the intensity of the peak is not taken into account but only its position is taken into account:

$$F'(c) = (\phi'_c(m))_{m \in M} \qquad (20)$$

$$\phi'_c(m) = \begin{cases} 1 & \text{if } m \in M(c) \\ 0 & \text{otherwise} \end{cases}$$

In these equations, M is the set of the m/z values of peaks observed from all chemical, M(c) is the set of the m/z values of peaks observed from the chemical, and I(m) is the intensity of a peak observed from the chemical at an m/z value.

(2) Creation of Gap Vector

For example, the intensity $g_i(j-i)$ corresponding to the distance between two mass spectrum peaks, observed at an m/z value i or j (j>i), having an intensity $I_i$ or $I_j$ is defined by formulas below.

The intensity $I_k$ of a mass spectrum belongs to the set (0, 1000) unless otherwise specified hereinafter.

$$\forall i, j; j - i \geq w, I_i, I_j \geq t,$$
$$g_i(j-i) = I_i \times \frac{\ln(I_j)}{\sum_{k;k>i,I_k \geq t} \ln(I_k)}$$
(21)

wherein t is the threshold of the intensity determined by taking a gap into account and w is the threshold of the difference between the m/z values of the two peaks. It should be noted that t is its threshold determined by taking the presence of noise into account and w is its threshold determined by taking the presence of a radioactive isotope into account.

Since $g_i(j-i)$ has a value determined by setting the goal line i of desorption and a large number of portions having the same m/z value, that is, j−i may be present in a single chemical, the intensity corresponding to a gap m over a single chemical c is given by the following equation:

$$gap_c(m) = \sum_{i; i+m \in M(c)} g_i(m)$$
(22)

wherein M(c) is the set of m/z values observed from the chemical c.

A gap vector corresponding to the mass spectrum of the chemical c is finally given by the following equations when the thresholds t and w in Formulas (21) are determined:

$$G_t^w(c) = (\xi_c(m))_{m \in M_g}$$
(23)
$$\xi_c(m) = \begin{cases} gap_c(m) & \text{if } m \in M_g(c) \\ 0 & \text{otherwise} \end{cases}$$

When the intensity of a peak is not taken into account but only its position is taken into account, a vector G'(c) is given by the following equations:

$$G_t^{w\prime}(c) = (\xi_c'(m))_{m \in M_g}$$
(24)
$$\xi_c'(m) = \begin{cases} 1 & \text{if } m \in M_g(c) \\ 0 & \text{otherwise} \end{cases}$$

In these equations, Mg is the set of gaps that are at least once observed in all chemicals to be vectorized and Mg(c) is the set of gaps that are observed in a chemical c.

Equations (25) below may be used to calculate $g_i(j-i)$ instead of Formulas (21). However, Formulas (21) are preferably used because the accuracy of discrimination is high.

1. $g_i(j-i) = \frac{I_i + I_j}{2}$ (25)

2. $g_i(j-i) = I_i \times \frac{1/I_j}{\sum_{k;k>i,I_k \geq t} 1/I_k}$

3. $g_i(j-i) = I_i \times \frac{I_j}{\sum_{k;k>i,I_k \geq t} I_k}$

4*. $g_i(j-i) = I_i \times \frac{-\ln(I_j)}{\sum_{k;k>i,I_k \geq t} -\ln(I_k)}$

5. $g_i(j-i) = I_i \times \frac{\ln(I_j)}{\sum_{k;k>i,I_k \geq t} \ln(I_k)}$

6*. $g_i(j-i) = I_i \times \frac{\exp(I_j)}{\sum_{k;k>i,I_k \geq t} \exp(I_k)}$

*$I_k \in (0, 1)$ (3) Conventional Vectorization Methods

Zernov et al. have vectorized chemicals using physicochemical properties in order to discriminate between drugs and non-drugs and in order to discriminate between agrichemicals and non-agrochemicals, (V. V. Zernov, K. V. Balakin, A. A. Ivaschenko, N. P. Savchuk, and I. V. Pletnev, Drug discovery using support vector machines, the case studies of drug-likeness, agrochemical-likeness, and enzyme inhibition predictions, *J. Chem. Inf. Comput. Sci.*, Vol. 43, pp. 2048-2056, 2003). Swamidass et al. have developed the following methods in order to vectorize chemicals for the purpose of discriminating between the mutageneticity and toxicity of the chemicals: (1) a method using a SMILES string derived from a chemical formula, (2) a method for extracting a path from the structural formula of a chemical, and (3) a method for calculating the distance between atoms from the three-dimensional structure of a chemical (S. J. Swamidass, J. Chen, J. Bruand, P. Phung, L. Ralaivola, and P. Baldi, Kernels for small molecules and the prediction of mutagenicity, toxicity and anti-cancer actibity, *Bioinformatics*, Vol. 21, No. Supple 1, pp. 359-368, 2005).

==Bonding Expression of Protein-Chemical Pair==

A vector a which is created using at least one of vectors $a_1$ to $a_x$ derived from the mass spectrum data of a chemical and which corresponds to the chemical is combined with a vector b which is created using a vector $b_k$ (k is an integer of one to y) derived from an amino acid sequence of a protein and which corresponds to the protein. A method for combining the vectors is not particularly limited.

(1) Concatenation Expression

The simplest way of combination is, for example, to combine the vectors (J. R. Bock and D. A. Gough, Predicting protein-protein interactions from primary structure, *Bioinformatics*, Vol. 17, No. 5, pp. 455-460, 2001 and S. M. Gomez, W. S. Noble, and A. Rzhetsky, Learning to predict protein-protein interactions, *Bioinformatics*, Vol. 19, pp. 1875-1881, 2003) and is expressed as follows:

$$B_{ab} = (a, b)$$ (26)

wherein a=(F, G) or (G) and b=(Clt(b)) or (Cot(b)).

In this case, the discriminant function of a SVM is given by the following equation:

$$f(c, p) = \text{sign}\left(\sum_{(c_i,p_i)\in SV_s} \alpha_i y_i K(B_{c_i p_i}, B_{cp}) + b^*\right) \quad (27)$$

In the case where RBF Kernel is used for a Kernel function, the following calculation is performed in this equation:

$$K_{conc.}(B_{a_1 b_1}, B_{a_2 b_2}) = K(a_1, a_2) \cdot K(b_1, b_2) \quad (28)$$

(2) Combination Expression

In "(1) Concatenation expression", chemical-chemical relationships or protein-protein relationships are focused and it is attempted to describe features of interactions in the form of the products of relationships. However, there can be a protein-chemical relationship characteristic of a protein and chemical interacting with each other. In order to evaluate the correlation, the following calculation is performed for combination expression instead of Equation (28):

$$K_{combi}(B_{a'_1 b'_1}, B_{a'_2 b'_2}) = K_{aa}(a'_1, a'_2) \cdot K_{bb}(b'_1, b'_2) \cdot K_{ab}(a'_1, b'_2) \cdot K_{ab}(b'_1, a'_2) \quad (29)$$

In the calculation, different Kernel functions may be used for Kaa, Kbb, and Kab. Furthermore, different parameters may be used. The adjustment of the parameters allows the relationships to be arbitrarily weighted.

In the calculation, the inner product of $a_1'$ and $b_2'$ needs to be determined. But when a and b have different vector lengths, the calculation is difficult; hence, a and b are processed such that $a_1'$ and $b_2'$ have the same vector length. This exerts an effect of eliminating the weight caused by a difference in vector length implicit in concatenation expression.

Specifically, when a=(F, G) and b represent a chemical and a protein, respectively, in Formula (29), the following Kernel function is calculated for each of protein-chemical pairs $B_1 = (a_1, b_1) = (F_1, G_1, C_1)$ and $B_{12} = (a_2, b_2) = (F_2, G_2, C_2)$:

$$K_{combi}(B_1, B_2) \equiv \prod_{I,J\in(F,G,C)} K_{IJ(=JI)}(I_1, J_2) \quad (30)$$

In this method, any one of the following four Kernel functions is used as Kij(x, y):

$$K_{IJ(=JI)}(x, y) = \begin{cases} 1. & (\gamma_{IJ} x^t y + 1)^3 \\ 2. & \exp(-\gamma_{IJ} \|x - y\|^2) \\ 3. & \tanh(\gamma_{IJ} x^t y + 1) \\ 4. & 1 \end{cases} \quad (31)$$

Herein, a vector derived from the protein and a vector derived from the protein may be adjusted in dimension number to each other such that these vectors have a constant length. The dimension number of the chemical-derived vector varies depending on the mass spectrum dataset or parameters of the chemical; however, the dimension number of the protein-derived vector does not depend on its mass spectrum dataset. Therefore, the dimension number of the protein-derived vector is preferably used. In this case, vectors having the same dimension number need to be created in such a manner that elements of which the number is equal to the dimension number of vectors used are extracted from the chemical-derived vector.

A method for selecting the elements is not particularly limited. The elements may be selected at random, but, for example, features that are probably most important in classifying the protein-chemical pair may be selected from among elements of the chemical-derived vector.

In the case where KFG(F1, G1) and the like in Formula (30) are calculated using one of Functions (31), the calculation results vary depending on the order of features of the vectors; hence, the order of the features may be determined in accordance with a standard below. If the number of the features needs to be reduced, the features are ranked in order of priority and a necessary number of the top features may be selected.

As for a fragment vector F corresponding to the chemical and a vector C corresponding to the protein, the features are ranked in descending order of MSE defined by the following equations for each feature i:

$$MSE_i^F = \sum_{c\in\mathfrak{C}} (F_i(c) - \overline{F}_i)^2 \quad (32)$$

$$\overline{F}_i = \frac{\sum_{c\in\mathfrak{C}} F_i(c)}{|\mathfrak{C}|}$$

wherein $\mathfrak{C}$ is the set of all chemicals listed in a dataset used. When $MSE^G_i$ for the protein vector C is calculated, $\mathfrak{P}$ that is the set of all proteins listed in the dataset is used instead of $\mathfrak{C}$.

A gap vector G is defined by the following equations:

$$MSE_i^G = \sum_{c\in\mathfrak{C}} \sum_{j; i+j\in M(c)} (g_j^c(i) - \overline{g}(i))^2 \quad (33)$$

$$\overline{g}(i) = \frac{\sum_{c\in\mathfrak{C}} \sum_{j; i+j\in M(c)} g_j^c(i)}{\sum_{c\in\mathfrak{C}} \sum_{j; i+j\in M(c)} 1}$$

wherein $\mathfrak{C}$ is the set of all chemicals listed in a dataset used, g(i) is the intensity corresponding to the calculated gap between a peak with an m/z value j and a peak with an m/z value i+j observed from a chemical c (see Formulas (21)), and M(c) is the set of m/z values observed from the chemical c.

In the case where the order of the features is determined, the features that appear frequently in the chemical or the protein and that vary significantly as calculated from Equation (32) or (33) are preferably ranked high. This is because these features probably have the highest expression power for discrimination. When the features are extracted for the purpose of reducing the dimension number of each vector, different vectors are analyzed for relationships between expressive features and whereby relationships between different vectors with higher expression power for discrimination are preferably extracted.

(3) Use of Vector Created by Vectorizing Chemical or Protein by Other Methods

In the case where a vector derived from a chemical is combined with a vector derived from a protein, the combined vector may include a vector derived from the mass spectrum data of the chemical. In another embodiment, the chemical-derived vector may be combined with a protein-derived vector created by vectorizing information other than information on the amino acid sequence or may be combined with multiple types of vectors such as chemical-derived vectors created by vectorizing information on physicochemical properties, chemical formulas, structural formulas, and/or three-dimensional structures. A method for combining the vectors is not particularly limited. The vectors may be combined by the above-mentioned method.

==Application to SVM==

As for a SVM, a commonly available program may be used. For example, LIBSVM, which is available on the web, may be used (C. C. Chang and C. J. Lin, LIBSVM: a library for support vector machines, 2001. In LIBSVM, operations such as C-support vector classification (C-SVC), v-support vector classification (v-SVC), one-class SVM, and v-support vector classification (v-SVC) are available. In an example below, C-support vector classification (C-SVC) was used.

LIBSVM recommends that scaling is used for each dimension of input data. Specifically, a value $s(x_{ij})$ obtained by scaling the jth dimension value $x_{ij}$ of an sample i is given by the following equation:

$$s(x_{ij}) = \begin{cases} l + (h-l) \times \dfrac{x_{ij} - \min_k x_{kj}}{\max_x x_{kj} - \min_k x_{kj}} & \text{if } \max_k x_{kj} \neq \min_k x_{kj} \\ 0 & \text{otherwise} \end{cases} \quad (34)$$

wherein l and h are a minimum and maximum, respectively, defined by a user. In examples below, scaling was used for input data unless otherwise specified.

In LIBSVM, a SVM is extended for probability estimation. In the present invention, probability estimation may be used to predict large-scale combinations such as "combinations of drug groups and large-scale sequence groups". This is because when many candidates of interactions are obtained by large-scale prediction, estimated probabilities can be indexes effective in ranking the candidates in order of priority.

==Method for Configuring Pattern Recognizer==

Using two classes of pairs of proteins and chemicals (a first pair and a second pair), which have different interactions (a first interaction and a second interaction), at least one selected from four parameters is vectorized, the four parameters being the position of a peak in mass spectrum data obtained from each chemical, the position and intensity of the peak, the distance between two peaks, and the distance between two peaks and their corresponding intensities; the amino acid sequence of each protein is vectorized; the vectors are combined; and a SVM is applied to the combined vectors and trained to learn them. Thus a pattern recognizer discriminating the classes can be configured.

Although the pattern recognizer is configured on the basis of the mass spectrum data of the chemicals and the amino acid data of the proteins, the pattern recognizer can highly correspond to the class of interactions by being trained on the basis of how they interact.

The Interaction described herein is not particularly limited as long as it occurs between a protein and a chemical, and may be a structural binding that bind them physically, a functional binding that exerts some effect on them, or the like. An embodiment in which they do not interact in a specific way, such as a mode having no bond, is included in the interaction.

As for a first pair and second pair, used for learning, having a first interaction and a second interaction, respectively, the first and second interactions need not relate to each other and the second interaction is preferably the action that they do not have the second interaction. A pair that has not been analyzed for interaction and has not been proven to have the first interaction can be actually regarded as a pair having no first interaction. Therefore, in this specification, such a pair that has not been analyzed for interaction and has not been proven to have the first interaction can be included in the pair having the second interaction.

==Method for Predicting Interaction Between Protein and Chemical==

By vectorizing a third pair of a chemical and a protein having an unknown interaction therewith are vectorized in the same manner as that described above and applying it to the pattern recognizer, it can be shown that the third pair belongs to which one of the two classes and that the third pair has which one of the first and second interactions.

EXAMPLES

Example 1

Coupling Between AR (Adrenergic Receptor) and Chemical

In this example, the following proteins and chemicals were used: nine types of human AR-family proteins (FIG. 5) having similar structures and 48 chemicals (FIG. 6) which were specified in ARDB (adrenergic receptor database) as agonists or antagonists and of which the mass spectrum data was specified in NIST05 (NIST/EPA/NIH mass spectral library). The protein-chemical pairs were classified by a classification method according to the present invention and were analyzed for interaction. Coupling schemes between the chemicals and AR were shown in FIG. 6b. As for whether the proteins were coupled to the chemicals, pairs (142 pairs) of the chemicals and the proteins that were targets were specified to be positive and pairs (290 pairs) of the chemicals and the proteins that were not any targets were specified to be negative.

(1) Discriminating Power Obtained Using Different Kernel Functions

The coupling of each AR-chemical pair was expressed with a vector $(F, G, C_{lt})$ in concatenation expression and discriminating power obtained using different Kernel functions was evaluated on the basis of sensitivity (sens.), precision (prec.), and accuracy (acc.) in 10-fold cross validation. In particular, each sample was divided into "n" equal parts, whereby "n" groups of datasets were prepared. One of the datasets was used as a test set. A model was trained to learn the other "n−1" groups of the datasets. The test set was evaluated with the resulting model. This procedure was repeated "n" times, whereby each of the "n" groups of the datasets was evaluated once. The datasets were evaluated for sens., prec., and acc. which were each defined by a corresponding one of Equations (35) below. Formulas (21) were used to calculate gap intensity.

$$sens. = \frac{TP}{TP + FN}, \quad prec. = \frac{TP}{TP + FP}, \quad (35)$$
$$acc. = \frac{TP + TN}{TP + FP + TN + FN}$$

In these equations, TP represents the number of true positives ($p_i=o_i=1$), FP represents the number of false positives ($p_i=1$, $o_i=1$), TN represents the number of true negatives ($p_i=o_i=-1$), and FN represents the number of false negatives ($p_i=-1$, $o_i=-1$) when two classes that are positive 1 and negative −1 are present in each pair, where $o_i$, represents the measurement result of each pair and $p_i$ represents the predicted result thereof by a prediction method. Obtained results were shown in FIG. 7.

As shown in this table, linear using no Kernel function, or giving no high-dimensional map, is inferior in every evaluation standard to the use of the Kernel functions. This shows that a protein-chemical interaction prediction issue can be solved with a non-linear SVM. According to all evaluation standards, RBF Kernel is most excellent in discrimination power among the Kernel functions.

(2) Discriminating Power Obtained Using Different Vectorizing Methods for Protein Discriminating power obtained in such a manner that each protein was vectorized by different vectorizing methods and binding was expressed by concatenation was shown in FIG. 8. Discriminating power was evaluated in the same manner as that described in Item (1).

As shown in this table, $C_{lt}$ and triclust have the highest accuracy, with the number of dimensions reduced. This shows the effectiveness of a method for linking partial character sequences to physicochemical properties. $C_{ld}$ and diclust, which are based on the same concept, have low accuracy. This is probably because features important in discrimination are mixed together in the case of 89 dimensions and therefore the discrimination ability thereof is lost. In comparison between $C_{od}$ and $C_{ot}$, $C_{od}$ has higher accuracy. In contrast, $C_{od}$, which has 4200 dimensions, has higher sequence-expressing ability as compared to $C_{od}$, which has 400 dimensions. The difference in accuracy between $C_{od}$ and $C_{ot}$ shows that there is no direct correlation between complexity in expression and accuracy.

The fact that the accuracy of $C_{id}$ (89 dimensions) or $C_{ot}$ (4200 dimensions) is not higher than the accuracy of $C_{lt}$ (199 dimensions) or $C_{od}$ (400 dimensions) suggests the presence of appropriate dimensions.

(3) Discriminating Power Obtained Using Different Vectorizing Methods for Chemical In this example, in order to compare effects of two vectors, a fragment vector F and a gap vector G, discriminating power obtained using F and G, shown in FIG. 9, for methods for vectorizing a chemical was calculated in such a manner that a method for vectorizing a protein was fixed to $C_{lt}$. Discriminating power was evaluated in the same manner as that described in Item (1).

As shown in this table, accuracy obtained by the use of F or G is not higher than accuracy obtained by the use of both F and G. Therefore, the fragment vector F and the gap vector G are preferably both taken into account. As for the role of each vector, F has higher accuracy and sens. as compared to G; hence, F well expresses features of the chemical and therefore is probably a base for discrimination. On the other hand, G has higher prec. as compared to F and (F, G) has higher prec. as compared to G; hence, G has an auxiliary function of increasing prec.

As shown in this table, the accuracy of vectorization by the use of the intensity of a peak in mass spectrum data is higher than that of vectorization by the nonuse of the peak intensity in most cases (FIG. 9). In particular, the use of F' instead of F causes a significant reduction in accuracy. Therefore, intensity is preferably used to express features of the chemical.

(4) Discriminating Power Obtained Using Different Bonding Expressions

Discriminating power obtained using each of bonding expressions such as concatenation expression and combination expression was calculated.

When vectors were combined together, the discriminating power of a pattern recognizer prepared by combining chemical-derived vectors created by a method below was also calculated for comparison. A 2D vector corresponding to a chemical c used to determine thresholds 1 and h involved in depth using paths was defined by the following equations:

$$D_l^h(c) = (\psi_c(p))_{p \in P_l^h} \quad (36)$$

$$\psi_c(p) = \begin{cases} \dfrac{f_c(p)}{\sum_{i \in P_l^h(c)} f_c(i)} & \text{if } p \in P_l^h(c) \\ 0 & \text{otherwise} \end{cases}$$

wherein $P^h_l$ is the set of paths from depth 1 to depth h appearing at least once in the structural formula of every chemical to be vectorized, $P^h_l(c)$ is the set of paths appearing in the structural formula of a chemical c, and fc(p) is the number of times a path p appears in the structural formula of the chemical c.

A 2D vector that was created in such a manner that the number of times a path appears was not taken into account but only the presence of the path was taken into account was defined by the following equations:

$$D_l^{h'}(c) = (\psi_c'(p))_{p \in P_l^h} \quad (37)$$

$$\psi_c'(p) = \begin{cases} 1 & \text{if } p \in P_l^h(c) \\ 0 & \text{otherwise} \end{cases}$$

In each case, discriminating power was evaluated in the same manner as that described in Item (1). The evaluation results were shown in FIG. 10.

As shown in this table, accuracy obtained using combination expression is higher than accuracy obtained using concatenation expression in this example. The use of 2D vectors D together results in an increase in accuracy.

Example 2

Functional Interactions Between ARs (Adrenergic Receptors) and Chemicals

In this example, chemicals were classified on the basis of whether the chemicals act as agonists or antagonists when being coupled to ARs. Data shown in FIG. 6 was used and results (FIG. 6a) obtained by taking no information $C_{lt}$ about proteins into account were compared to results (FIG. 6b) obtained by taking information $C_{lt}$ into account. The chemicals acting as agonists were specified to be negative and those acting as antagonists were specified to be positive. As for the types of AR proteins, α1 has three types of A, B, and D and α2 has three types of A, B, and C. Therefore, 26 pairs are positive when no information $C_{lt}$ is taken into account (FIG. 6a), 69 pairs are positive when information $C_{lt}$ is taken into account (FIG. 6b), 22 pairs are negative when no information $C_{lt}$ is taken into account (FIG. 6a), and 73 pairs are negative when information $C_{lt}$ is taken into account (FIG. 6b). The classification results are shown in FIG. 11. The discriminating power of a pattern recognizer prepared in this example was evaluated in the same manner as that described in Item (1) of Example 1.

Results (FIG. 11A) obtained by taking protein information into account using any vector are extremely high in accuracy and are higher in accuracy than results (FIG. 11B) obtained by taking no protein information into account.

Example 3

Use of Data Stored in Drugbank (D. S. Wishart, C. Knox, A. C. Guo, S. Shrivastava, M. Hassanali, P. Stothard, Z. Chang, and J. Woolsey, DrugBank: a comprehensive resource for in silico drug discover and exploration, *Nucleic Acids Res.*, Vol. 34 (Database issue), pp. D668-D672, 2006)

In this example, 980 pairs (FIG. 12) of proteins and chemicals having mass spectrum data specified in NIST05 were sampled among drug-target protein pairs specified in Drug-Bank Approved Drug Target Protein Sequences and were then used to verify a classification method according to the present invention. Pairs specified to be coupled were used as positive samples. Pairs not specified to be coupled were selected at random and were then used as negative samples. The discriminating power of a pattern recognizer prepared in this example was evaluated in the same manner as that described in Item (1) of Example 1. The evaluation results are shown in FIG. 13.

As shown in this table, the drug-target protein pairs were classified with high accuracy using the samples in this example. The use of $C_{lt}$ or $C_{od}$, which is a method for vectorizing a protein, tends to provide high accuracy under conditions of this example. In contrast to Example 1, the use of $C_{od}$ provides higher accuracy. In this example as well as Example 1, the use of combination expression for a method for combining vectors provides high accuracy.

Discriminating power was calculated for G by different intensity calculation methods. As shown in FIG. 14, the use of Calculation Formulas 3, 5, and 6 provides high accuracy.

The influence of the number of the negative samples on final accuracy was investigated. This showed that an increase in the number of the negative samples hardly changed prec., reduced sens., and increased acc. (FIG. 15).

Pattern recognizers with recording process are obtained with high accuracy under every condition. Optimum conditions vary slightly depending on datasets used.

Example 4

Use of Receptors in Data Stored in Drugbank

In this example, pairs of proteins and chemicals acting as receptors and ligands, respectively, were selected from data stored in DrugBank, classified, and then used to evaluate discriminating power.

As shown in FIG. 16, this example provides accuracy higher than that obtained in Example 3 in which accuracy involved in interaction, that is, bonding was evaluated. Therefore, a pattern recognizer is preferably trained to learn protein-chemical interactions depending on specific modes.

Example 5

Advantages in Selecting Features by PCA

In this example, a matrix $Q_F$, a matrix $Q_G$, and a matrix $Q_C$ were applied to a fragment vector F, a gap vector G, and a protein vector C, respectively. For example, the matrix $Q_F$ is as follows ($Q_G$ and $Q_C$ are as well as $Q_F$ and F is exemplified below):

$$Q_F = \begin{pmatrix} F_1 \\ F_2 \\ \vdots \\ F_{|\mathfrak{C}|} \end{pmatrix} \quad (38)$$

wherein $\mathfrak{C}$ is the set of all chemicals appearing in a dataset used (for $Q_C$, $\mathfrak{C}$ is the set of all proteins appearing in a dataset used).

The matrix Q was subjected to principal component analysis, whereby a principal component score matrix S was obtained. The statistical analysis software Rprcomp was used for principal component analysis. A fragment vector F"(c) created by extracting "n" features from a chemical c was defined by the following equation:

$$F''(c) = (S_{c1}, S_{c2}, \ldots, S_{cn}) \quad (39)$$

In this example, no scaling was performed.

FIG. 17 shows discriminating power that was obtained in such a manner that features were selected and sequences were determined by applying PCA to the data of AR described in Example 1 and data specified in DrugBank described in Example 3.

As shown in this table, protein-chemical interactions can be predicted by selecting appropriate features. Elements showing discriminating power are improved depending on conditions.

Example 6

Prediction of Chemicals Binding to Proteins

In this example, an SVM model trained to learn a Drug-Bank dataset was used as a pattern recognizer to check proteins binding to Cytochrome P450 2El (UniProt P05181) and Monoamine Oxidase A (UniProt ID: P1397) for 519 chemicals in the DrugBank dataset. The accuracy of predicting the chemicals binding to Cytochrome P450 2El and that of predicting the chemicals binding to Monoamine Oxidase A were 92.29% and 94.61%, respectively. This shows that binding chemicals can be selected from chemical libraries.

INDUSTRIAL APPLICABILITY

According to the present invention, the following methods can be provided: a comprehensive method for classifying a pair of a protein and a chemical using versatile, readily available data and a method for predicting an unknown interaction between pairs using the classifying method.

The invention claimed is:

1. A method for configuring a pattern recognizer discriminating between a class to which a first pair of a protein and a chemical having a first interaction belong and a class to which a second pair of a protein and a chemical having a second interaction belong, comprising:
    a step of vectorizing at least one of parameters of mass spectrum data obtained from each chemical into vectors $a_1$ to $a_x$ (x is an integer of one or more); and
    a step of vectorizing each protein into vectors $b_1$ to $b_y$ (y is an integer of one or more),
    wherein one of the vectors $a_1$ to $a_x$ derived from the chemical is combined with a vector $b_k$ (k is an integer of one to y) derived from the protein paired with the chemical and a support vector machine (SVM) running on a computer is applied to the combined vectors and trained to learn the same.

2. The method for configuring a pattern recognizer according to claim 1, wherein at least one of the mass spectrum data parameters is selected from four parameters that are the position of a peak, the position and intensity of the peak, the distance between two peaks, and the distance between two peaks and intensities thereof.

3. The method for configuring a pattern recognizer according to claim 1, wherein the vectors $b_1$ to $b_y$ have elements of the frequency of a predetermined amino acid sequence appearing in the protein.

4. The method for configuring a pattern recognizer according to claim 1, wherein one of the vectors derived from each chemical is a vector $F(c)$ given by the following equations:

$$F(c) = (\phi_c(m))_{m \in M} \qquad (1)$$

$$\phi_c(m) = \begin{cases} I_c(m) & \text{if } m \in M(c) \\ 0 & \text{otherwise} \end{cases}$$

wherein M is the set of the m/z values of peaks observed from all of the chemicals, M(c) is the set of the m/z values of peaks observed from the chemical of the pair, and I(m) is the intensity of a peak observed from the chemical of the pair.

5. The method for configuring a pattern recognizer according to claim 1, wherein one of the vectors derived from each chemical is a vector $F'(c)$ given by the following equations:

$$F'(c) = (\phi'_c(m))_{m \in M} \qquad (2)$$

$$\phi'_c(m) = \begin{cases} 1 & \text{if } m \in M(c) \\ 0 & \text{otherwise} \end{cases}$$

wherein M is the set of the m/z values of peaks observed from all of the chemicals and M(c) is the set of the m/z values of peaks observed from the chemical of the pair.

6. The method for configuring a pattern recognizer according to claim 1, wherein one of the vectors derived from each chemical is a vector $G^w_t(c)$ given by the following equations:

$$G^w_t(c)(\xi_c(m))_{m \in M_g} \qquad (3)$$

$$\xi_c(m) = \begin{cases} gap_c(m) & \text{if } m \in M_g(c) \\ 0 & \text{otherwise} \end{cases}$$

wherein Mg is the set of the difference between the m/z values of each two peaks observed from all of the chemicals to be classified, Mg(c) is the set of the difference j−i between the m/z values i and j of each two peaks observed from the chemical of the pair, $$gap_c(m) = \sum_{i; i+m \in M(c)} g_i(m) \qquad (4)$$

wherein M(c) is the set of the m/z values of peaks observed from the chemical of the pair, $$\forall i, j; j - i \geq w, I_i, I_j \geq t, \qquad (5)$$

$$g_i(j - i) = I_i \times \frac{\ln(I_j)}{\sum_{k; k > i, I_k \geq t} \ln(I_k)}$$

wherein Ii and Ij are the intensities of two peaks observed at m/z values i and j, respectively, t is the threshold of the intensity determined by taking a gap into account, and w is the threshold of the difference j−i between the m/z values of the two peaks observed at the m/z values i and j.

7. The method for configuring a pattern recognizer according to claim 1, wherein one of the vectors derived from each chemical is a vector $G^{w'}_t(c)$ given by the following equations:

$$G^{w'}_t(c) = (\xi'_c(m))_{m \in M_g} \qquad (6)$$

$$\xi'_c(m) = \begin{cases} 1 & \text{if } m \in M_g(c) \\ 0 & \text{otherwise} \end{cases}$$

wherein Mg is the set of the difference between the m/z values of each two peaks observed from all of the chemicals to be classified and Mg(c) is the set of the difference between the m/z values of each two peaks observed from a chemical of a third pair.

8. The method for configuring a pattern recognizer according to claim 1, wherein the vectors derived from each chemical and the vectors derived from the protein paired with the chemical are combined into a vector $(a_l, b_k)$ or $(a_p, a_q, b_k)$, wherein l, p, and q are one of 1 to x and k is one of 1 to y; and the support vector machine (SVM) is applied to this vector and trained to learn the same.

9. The method for configuring a pattern recognizer according to claim 1, wherein at least one selected from four parameters that are a physicochemical property, the chemical formula, the structural formula, and the three-dimensional structure of each chemical is vectorized into a vector D; the vectors derived from the chemical, the vectors derived from the protein paired with the chemical, and the vector D are combined into a vector $(a_l, D, b_k)$ or $(a_p, a_q, D, b_k)$, wherein l, p, and q are one of 1 to x and k is one of 1 to y; and the support vector machine (SVM) is applied to this vector and trained to learn the same.

10. The method for configuring a pattern recognizer according to claim 1, wherein the discrimination function of the support vector machine is given by the following equation:

$$f(c, p) = \text{sign}\left(\sum_{(c_i, p_i) \in SVs} \alpha_i y_i K(B_{c_i p_i}, B_{cp}) + b^*\right). \qquad (7)$$

11. The method for configuring a pattern recognizer according to claim 10, wherein the following equation $K_{conc.}$ (8) is applied to Equation (7):

$$K_{conc.}(B_{a_1 b_1}, B_{a_2 b_2}) = K(a_1, a_2) \cdot K(b_1, b_2). \qquad (8)$$

12. The method for configuring a pattern recognizer according to claim 10, wherein the following equation $K_{combi.}$ (9) is applied to Equation (7):

$$K_{combi}(B_{a'_1 b'_1}, B_{a'_2 b'_2}) = K_{aa}(a'_1, a'_2) \cdot K_{bb}(b'_1, b'_2) \cdot K_{ab}(a'_1, b'_2) \cdot K_{ab}(b'_1, a'_2). \qquad (9)$$

13. The method for configuring a pattern recognizer according to claim 1, wherein the support vector machine uses a linear kernel, a polynomial kernel, an RBF (radial basis function) kernel, or a sigmoid kernel.

14. The method for configuring a pattern recognizer according to claim 1, wherein the first interaction is that the protein and the chemical are bound to each other, the second interaction is that the protein and the chemical are not bound to each other, and the protein-chemical pair is classified on the basis of whether the protein and the chemical are bound to each other.

15. The method for configuring a pattern recognizer according to claim 1, wherein the interaction is that a protein and a chemical are functionally coupled to each other, the first interaction is that the chemical acts as an agonist when being bound to the protein, the second interaction is that the chemical acts as an antagonist when being bound to the protein, and the protein-chemical pair is classified on the basis of whether the chemical acts as an agonist or an antagonist when being coupled to the protein.

16. A method for predicting an interaction between a protein and a chemical, comprising:

a step of, with use of a first pair of a protein and a chemical having a first interaction, and a second pair of a protein and a chemical having a second interaction, and a third pair of a protein and chemical to be subjected to prediction, configuring a pattern recognizer discriminating between a class to which the first pair belong and a class to which the second pair belong, by the method for configuring a pattern recognizer according to claim 1; and a step of applying the pattern recognizer to a vector B created from the third pair to determine whether the third pair belongs to which one of the two classes.

17. A method for screening a chemical binding to a specific protein from a chemical library, comprising a step of predicting an interaction between the protein and the chemical by applying the predicting method according to claim 16 to chemicals contained in the chemical library.

18. A method for screening a protein binding to a specific chemical from a protein library, comprising a step of predicting an interaction between the chemical and the protein by applying the predicting method according to claim 16 to proteins contained in the protein library.

19. A method for configuring a pattern recognizer discriminating between a class to which a first pair of a protein and a chemical having a first interaction belongs and a class to which a second pair of a protein and a chemical having a second interaction belongs, comprising:

a step of vectorizing at least one of parameters of mass spectrum data obtained from each chemical into one of vectors $a_1$ to $a_x$ (x is an integer of one or more); and a step of training a support vector machine (SVM) running on a computer with the vectors $a_1$ to $a_x$ derived from the chemical.

* * * * *

UNITED STATES PATENT AND TRADEMARK OFFICE
CERTIFICATE OF CORRECTION

| | | |
|---|---|---|
| PATENT NO. | : 8,185,321 B2 | Page 1 of 1 |
| APPLICATION NO. | : 12/447814 | |
| DATED | : May 22, 2012 | |
| INVENTOR(S) | : Yasubumi Sakakibara et al. | |

It is certified that error appears in the above-identified patent and that said Letters Patent is hereby corrected as shown below:

In the Claims

Column 22, Claim 7, Line 8, replace "vector $G^{w'}_{tt}(c)$" with --vector $G^{w'}_{t}(c)$--.

Signed and Sealed this
Seventh Day of July, 2015

Michelle K. Lee
*Director of the United States Patent and Trademark Office*